(12) United States Patent
Stansbury

(10) Patent No.: US 9,138,383 B1
(45) Date of Patent: Sep. 22, 2015

(54) NANOGEL MATERIALS AND METHODS OF USE THEREOF

(75) Inventor: Jeffrey W. Stansbury, Centennial, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 852 days.

(21) Appl. No.: 12/328,089

(22) Filed: Dec. 4, 2008

Related U.S. Application Data

(63) Continuation-in-part of application No. 11/117,957, filed on Apr. 28, 2005, now abandoned.

(60) Provisional application No. 60/566,467, filed on Apr. 28, 2004.

(51) Int. Cl.
*A61K 6/083* (2006.01)
*A61K 6/00* (2006.01)

(52) U.S. Cl.
CPC ............... *A61K 6/083* (2013.01); *A61K 6/0047* (2013.01); *A61K 6/0008* (2013.01)

(58) Field of Classification Search
CPC .... A61K 6/083; A61K 6/0008; A61K 6/0047
USPC ........................................................ 523/116
See application file for complete search history.

(56) References Cited

U.S. PATENT DOCUMENTS

| | | | |
|---|---|---|---|
| 3,066,112 A | 11/1962 | Bowen | |
| 3,179,623 A | 4/1965 | Bowen | |
| 3,194,784 A | 7/1965 | Bowen | |
| 3,751,399 A | 8/1973 | Lee, Jr. et al. | |
| 3,926,906 A | 12/1975 | Lee et al. | |
| 5,252,428 A * | 10/1993 | Kawamoto et al. | 430/271.1 |
| 5,276,068 A | 1/1994 | Waknine | |
| 5,318,999 A * | 6/1994 | Mitra et al. | 522/57 |
| 5,866,047 A * | 2/1999 | Nagino et al. | 264/1.27 |
| 5,874,511 A | 2/1999 | Rizzardo et al. | |
| 5,969,000 A | 10/1999 | Yang et al. | |
| 6,402,315 B1 * | 6/2002 | Kato | 347/100 |
| 6,579,914 B1 * | 6/2003 | Gantt et al. | 522/92 |
| 6,624,261 B1 | 9/2003 | Moad et al. | |
| 6,713,584 B1 | 3/2004 | Chisholm et al. | |
| 2002/0177522 A1 | 11/2002 | Alexander et al. | |
| 2002/0193521 A1 | 12/2002 | Cruz et al. | |
| 2003/0232914 A1 | 12/2003 | Devonport et al. | |
| 2004/0029044 A1 * | 2/2004 | Severance et al. | 430/281.1 |
| 2004/0059019 A1 * | 3/2004 | Nakano et al. | 523/160 |
| 2004/0063867 A1 | 4/2004 | Cruz | |
| 2004/0213928 A1 * | 10/2004 | Sebastian et al. | 428/32.17 |
| 2004/0236050 A1 | 11/2004 | Lundquist et al. | |

(Continued)

OTHER PUBLICATIONS

Fixe, F.; Dufva, M.; Telleman, P.; Christensen, C. B. V. Nucleic Acids Res. 2004, 32, e9. Oxford University Press; 2004.*

(Continued)

*Primary Examiner* — Michael Pepitone
(74) *Attorney, Agent, or Firm* — Thompson Coburn LLP; Steven M. Ritchey

(57) ABSTRACT

The present invention provides soluble nanogel polymers produced by polymerization of a monomer mixture comprising a monovinyl monomer, multivinyl monomer, and an iniferter. The disclosure also provides a reactive nanogel with pendant reactive groups such as oxirane or (meth)acrylate groups.

31 Claims, 22 Drawing Sheets

(56) References Cited

U.S. PATENT DOCUMENTS

2006/0074186 A1     4/2006   Barron et al.
2011/0021347 A1*   1/2011   Ugajin et al. ................ 502/402

OTHER PUBLICATIONS

BASF Technical Information Guide (Mar. 2008) "Lucirin® grades: photo initiators for pigmented UV-curable coatings and printing inks as well as for UV-stabilized topcoats for outdoor use", EVP 0030405 e.

Berchtold et al. (2001) "Using Changes in Initiation and Chain Transfer Rates to Probe the Kinetics of Cross-linking Photopolymerications: Effects of Chain Length Dependent Termination" Macromolecules 34: 5103-5111.

Chang et al. (1995) "Monitoring Polymerization Reactions by Near-IR Spectroscopy" Multidimensional Spectroscopy of Polymer (American Chemical Society), Chapter 9, pp. 149-165.

Chiu and Lee (1995) "Microgel Formation in the Free Radical Crosslinking Polymerization of Ethylene Glycol Dimethacrylate (EGDMA). 1. Experimental" J. of Polymer Science: Part A: Polymer Chemistry 33: 257-267.

Ciba Specialty Chemicals Inc. (undated) "Photoinitiators for UV Curing".

Costello et al. (2002) "Branched methacrylate copolymers from multifunctional monomers: chemical composition and physical architecture distributions" Polymer 42: 245-254.

Downey et al. (2001) "Poly(divinylbenzene) Microspheres as an Intermediate Morphology between Microgel, Macrogel, and Coagulum in Cross-Linking Precipitation Polymerization" Macromolecules 34: 4534-4541.

Dušek (1993) "Special Features of Network Formation by Chain Crosslinking Copolymerization" Collect. Czech. Chem. Commun. 58: 2245-2265.

Graham et al. (1995) "Microgels 1: Solution polymerization using vinyl monomers" Macromolecular Symposia 93:293-300.

Hacioğlu et al. (2002) "Polymerication kinetics of HEMA/DEGDMA: using changes in initiation and chain transfer rates to explore the effects of chain-length-dependent termination" Biomaterials 23: 4057-4064.

Hutchison et al. (2000) "Microgel formation in Highly Crosslinked Polymers: Simulated and Experimental Results" Polymer Preprints 41(2): 1326-1327.

Isaure et al. (2003) "Facile synthesis of branched poly(methyl methacrylate)s" J. Mater. Chem. 13: 2701-2710.

Kim et al. (1999) "Preparation and Characterization of Poly(methylmethacrylate-co-ethylene glycol dimethacrylate) Microgels" J. of Industrial and Engineering Chemistry 5(4): 285-289.

Matsumoto et al. (1987) "Gelation in the copolymerization of methyl methacrylate with oligoglycol dimethacrylates" Makromolekulare Chemie-Rapid Communications 8: 373-375.

Naghash et al. (1997) "Gel formation by chain-crosslinking photopolymerization of methyl methacrylate and ethylene glycol dimethacrylate" Polymer 38(5): 1187-1196.

O'Brien et al. (2000) "Facile, versatile and cost effective route to branched vinyl polymers" Polymer 41: 6027-6031.

Otsu (2000) "Iniferter concept and living radical polymerization" J Polym Sci A: Polym Chem 38: 2121-2136.

Qin et al. (2000) "Radical polymerization of styrene initiate with a new multifunctional iniferter" Polymer Bull. 44: 123-128.

Slark et al. (2003) "Branched methacrylate copolymers from multifunctional comonomers: the effect of multifunctional monomer functionality on polymer architecture and properties" J. Mater. Chem. 13: 2711-2720.

Stansbury et al. (2001) "Determination of double bond conversion in dental resins by near infrared spectroscopy" Dental Materials 17: 71-79.

Stansbury et al. (2001) "Monitoring Vinyl Copolymerizations with Near-Infrared Spectroscopy Polymer Preprints" 42(1): 308-309.

* cited by examiner

US 9,138,383 B1

NANOGEL MATERIALS AND METHODS OF USE THEREOF

RELATED APPLICATIONS

This application is a continuation-in-part of U.S. application Ser. No. 11/117,957, filed Apr. 28, 2005, now abandoned, which claims the benefit of U.S. Provisional Application Ser. No. 60/566,467, filed Apr. 28, 2004, each of which is hereby incorporated herein by reference.

STATEMENT REGARDING FEDERALLY SPONSORED RESEARCH OR DEVELOPMENT

This invention was made with government support under Grant No. R21DE018354 awarded by the National Institutes of Health. The government has certain rights to this invention.

FIELD OF THE INVENTION

The present invention relates to a polymer composition, in particular to a nanogel composition and a method of preparation therefor.

BACKGROUND OF THE INVENTION

Branched polymers are branched polymer molecules of finite size which differ from crosslinked polymer networks. The latter tend towards an infinite size having interconnected molecules and are generally insoluble. Branched polymers are typically soluble in solvents which dissolve analogous linear polymers but have the advantage that branched polymers solutions are generally less viscous than similarly concentrated solutions of the corresponding linear polymer. Therefore, branched polymers solutions are easier to handle particularly at high solids content, requiring less solvent than linear polymers solutions. Branched polymers typically have a lower melt viscosity than analogous linear polymers and are useful for improving melt processability in injection moulding, compression moulding, extrusion moulding or powder coatings.

SUMMARY OF THE INVENTION

The present invention provides soluble nanogel polymers produced by polymerization of a monomer mixture comprising a monovinyl monomer, multivinyl monomer, and an iniferter. The disclosure also provides a reactive nanogel with pendant reactive groups such as oxirane or (meth)acrylate groups.

In one embodiment, the disclosure provides a soluble polymer particulate which is derived from a monomer mixture comprising at least one monovinyl monomer, at least one divinyl monomer, and an iniferter.

In one aspect, the soluble polymer particulate is derived from a monomer mixture comprising at least one monovinyl monomer, at least one divinyl monomer, an iniferter, and a chain transfer agent. In one aspect, the chain transfer agent is selected from among monovinyl thiols, divinyl thiols, difunctional thiols, trifunctional thiols, tetrafunctional thiols, pentafunctional thiols, hexafunctional thiols, octafunctional thiols, and bis(borondifluorodimethylglyoximate) cobaltate (II). In a certain aspect, the chain transfer agent is selected from propyl mercaptan, butyl mercaptan, hexyl mercaptan, octyl mercaptan, dodecanethiol, thioglycolic acid, methylbenzenethiol, dodecanethiol, mercaptopropionic acid, 2-ethyl hexyl thioglycolate, octylthioglycolate, mercaptoethanol, mercaptoundecanoic acid, thiolactic acid, thiobutyric acid, trimethylol propane tris(3-mercaptopropionate), pentaerythritol tetra(3-mercaptopropionate), pentaerythritol tetrathioglycolate, pentaerythritol tetrathiolactate, pentaerythritol tetrathiobutyrate; dipentaerythritol hexa(3-mercaptopropionate), dipentaerythritol hexathioglycolate; tripentaerythritol octa(3-mercaptopropionate), and tripentaerythritol octathioglycolate. In a specific aspect, the chain transfer agent is selected from 1-dodecanethiol and mercaptoethanol.

In another aspect, the soluble polymer particulate is derived from a monomer mixture comprising at least one monovinyl monomer, at least one divinyl monomer, an iniferter, and a thermal initiator.

In a further aspect, the soluble polymer particulate is derived from a monomer mixture comprising at least one monovinyl monomer, at least one divinyl monomer, an iniferter, and a photoinitiator.

In one aspect, the soluble particle particulate derived from a monomer mixture comprising at least one monovinyl monomer, at least one divinyl monomer, and an iniferter exhibits an equivalent diameter of from about 1 nm to about 200 nanometers; more particularly of from about 10 nm to about 60 nanometers.

In another aspect, the soluble polymer particulate derived from a monomer mixture comprising at least one monovinyl monomer, at least one divinyl monomer, and an iniferter; the monomer mixture contains at least about 5 mol % divinyl monomer; at least about 25 mol % divinyl monomer; at least about 50 mol % divinyl monomer; or at least about 75 mol % divinyl monomer based on the total moles of the monomer mixture.

In a further aspect, the soluble polymer particulate derived from a monomer mixture comprising at least one monovinyl monomer, at least one divinyl monomer, and an iniferter, the monovinyl monomer is selected from a $C_1$-$C_{20}$ alkyl(meth)acrylate, an aromatic (meth)acrylate or (meth)acrylic acid. In one specific aspect, the monovinyl monomer $C_1$-$C_{20}$ alkyl (meth)acrylate is ethyl(meth)acrylate or isobornyl(meth)acrylate. In another specific aspect, the monovinyl monomer aromatic (meth)acrylate is 2-phenoxyethyl(meth)acrylate, benzoyl(meth)acrylate, or phenyl(meth)acrylate.

In a further aspect, the soluble polymer particulate derived from a monomer mixture comprising at least one monovinyl monomer, at least one divinyl monomer, and an iniferter, the divinyl monomer is selected from one or more of ethylene glycol di(meth)acrylate, hexanediol di(meth)acrylate, tripropylene glycol di(meth)acrylate, butanediol di(meth)acrylate, neopentyl glycol di(meth)acrylate, diethylene glycol di(meth)acrylate, triethylene glycol di(meth)acrylate, dipropylene glycol di(meth)acrylate, allyl(meth)acrylate, urethane di(meth)acrylate, 2,2'-bis[4-(3-methacryloxy-2-hydroxy propoxy)-phenyl]propane (bis-GMA), ethoxylated bisphenol-A-di(meth)acrylate and divinyl benzene. In a specific aspect, the divinyl monomer is ethylene glycol di(meth)acrylate or urethane di(meth)acrylate.

In one aspect, the soluble polymer particulate derived from a monomer mixture comprising at least one monovinyl monomer, at least one divinyl monomer, and an iniferter, the iniferter is selected from a photoiniferter or a thermal iniferter. In one aspect, the photoiniferter is selected from diphenyldisulfide, benzyl N,N-diethyldithiocarbamate, tetraetylthiuram disulfide, phenyltriphenylazomethane, isopropylxanthic disulfide, p-xylylene bis-N,N-diethyldithiocarbamate, and benzyl dithiocarbamate.

In another aspect, the thermal iniferter is selected from N-bromosuccinimide (NBS), diethyl-2,3-dicyano-2,3-di(p- tolyl)succinate (DCDTS), phenylazotriphenyl methane (APT), and diethyl 2,3-dicyano-2,3-di(p-N,N-diethyldithiocarbamylmethyl)phenyl-succinate (DDDCS).

In another embodiment, the disclosure provides a method of making a nanogel comprising combining a monomer mixture comprising a monovinyl monomer, a divinyl monomer, an initiator, a chain transfer agent, and an iniferter; and initiating polymerization of the monomer mixture. One aspect involves dissolving the monomer mixture in a solvent and optionally recovering the nanogel polymer from the solvent after polymerization.

In a further embodiment, the disclosure provides a method of preparing a surface-derivitized nanogel, the method comprising combining a monomer mixture comprising a monovinyl monomer, a divinyl monomer, an initiator, a chain transfer agent, and an iniferter; initiating polymerization of the monomer mixture to form a living nanogel; adding an additional monomer without additional initiator to the living nanogel to create a nanogel monomer mixture; and polymerizing the nanogel monomer mixture to form a surface-derivitized nanogel.

In another embodiment, the disclosure provides a reactive nanogel with pendant reactive surface groups produced by a process comprising combining a monomer mixture comprising at least one functional monomer, at least one divinyl monomer, and a chain transfer agent; initiating polymerization of the monomer mixture to form a living nanogel; adding an additional monomer without additional initiator to the living nanogel to create a nanogel monomer mixture; and polymerizing the nanogel monomer mixture to form a reactive nanogel with pendant reactive surface groups. In one aspect, the additional monomer is selected from a multi-vinyl monomer, a divinyl monomer, or a functional monomer. In another aspect, the functional monomer is selected from hydroxy alkylacrylates, hydroxy alkyl(meth)acrylates, oxirane(meth)acrylates, dialkyl aminoalkyl(meth)acrylates, and norbornyl(meth)acrylate. In a further aspect, the monomer mixture further comprises a chain transfer agent. In another aspect, the monomer mixture further comprises an initiator.

In a further embodiment, the disclosure provides a reactive nanogel with pendant olefinic groups produced by a process comprising combining a monomer mixture comprising at least one functional monomer, at least one divinyl monomer, a difunctional chain transfer agent, and an initiator; polymerizing said mixture to form a functionalized nanogel; and reacting the functionalized nanogel with a reactive olefinic compound to form a reactive nanogel with pendant olefinic groups. In one aspect, the pendant olefinic groups are selected from styryl, allyl, vinyl ether, and (meth)acrylate groups. In another aspect, the reactive olefinic compound is selected from (meth)acryloyl chloride, (meth)acrylic anhydride, (meth)acrylic acid, isocyanatoalkyl(meth)acrylate, isocyanatoethyl(meth)acrylate vinylbenzene chloride, chloroethyl vinyl ether, allyl chloride and isocyanatomethyl(meth)acrylate. In a further aspect, the difunctional chain transfer agent is selected from mercaptoethanol, mercaptopropanol, 3-mercapto-2-butanol, 2-mercapto-3-butanol, 3-mercapto-2-methyl-butan-1-ol, 3-mercapto-3-methyl-hexan-1-ol and 3-mercaptohexanol.

DETAILED DESCRIPTION OF THE INVENTION

Figure 1:
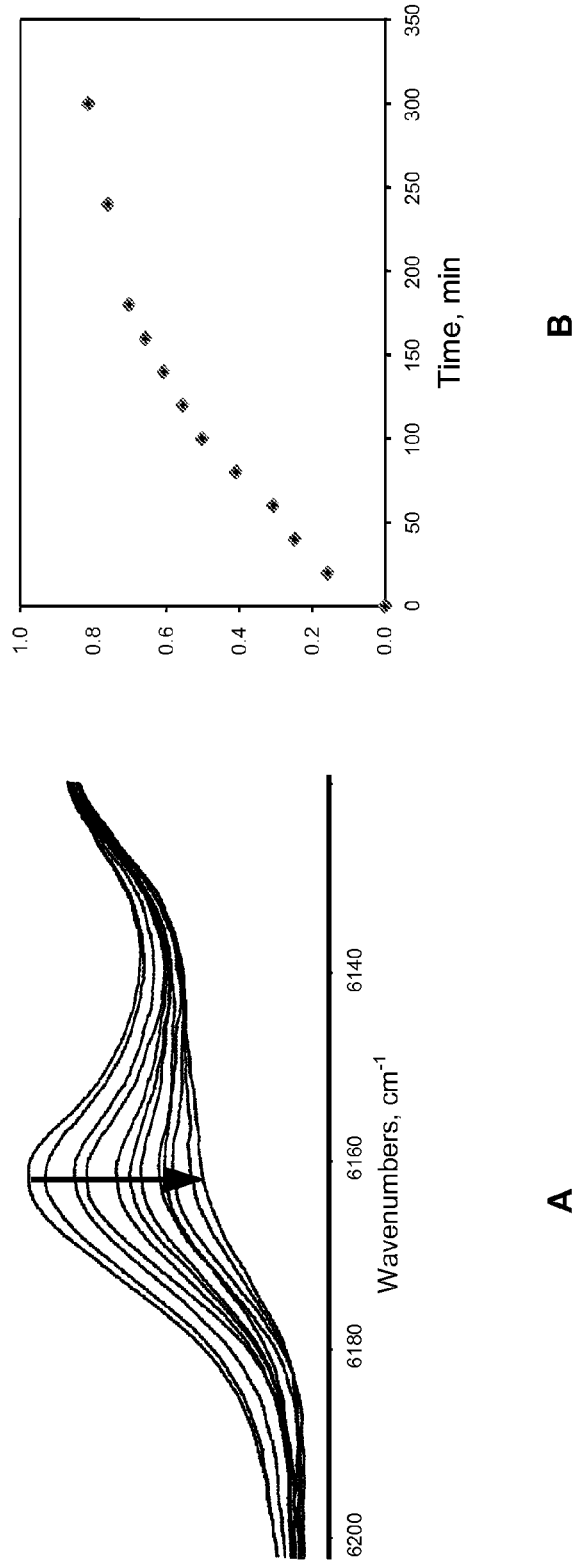
FIGS. 1(A) and 1(B) show a partial near infrared (NIR) spectral series (FIG. 1(A)) in toluene of ethyl(meth)acrylate/tetraethylene glycol di(meth)acrylate thermal polymerization in the presence of dodecanethiol. Plot of conversion vs. time (FIG. 1(B)) based on peak area of the (meth)acrylate=C—H absorption at 6163 cm$^{-1}$.

Traditionally, the term "nanogel" means a polymer gel particle having any shape with an equivalent diameter of approximately a few to 100 nm. "Nanogel" describes the interconnected localized network structures as well as appropriately describing the physical dimensions of the polymer gel particle. Nanogels are typically soluble in the solvent in which they are made and nanogels may be further made to be soluble in various liquids as necessary depending on the monomers used in their manufacture. However, nanogels can also be prepared in the absence of solvent (in bulk) and subsequently dissolved in an appropriate solvent or monomer composition.

As used herein, the term "nanogel", that is a soluble polymer particulate, is defined as a soluble, porous polymer gel particle having any shape with an equivalent diameter of about 1 to 200 nm, or greater, so long as the particle remains soluble in a target solvent or a monomer composition with which the nanogel is intended to be used. A nanogel is soluble in that it is uniformly dispersible in the target solvent or monomer composition. In one aspect, the nanogel of the present invention has an equivalent diameter of about 10 nm to about 60 nm. In another aspect, the diameter of the nanogel is such that it can be visualized by atomic force microscopy.

The term "macrogel" was developed initially to describe the precursor micro-structures that eventually connect to create the infinite crosslinked polymeric networks ("macrogel"). A "macrogel" is an insoluble polymer gel microparticle having any shape with an equivalent diameter of approximately 0.1 to 100 μm. A polymer gel particle is a particle composed of a polymer gel and having any shape. A polymer gel is a gel based on a polymer network.

A "polymer" is a substance composed of macromolecules. A polymer macromolecule is a molecule of high relative molecular mass, the structure of which comprises the multiple repetition of units derived from molecules of low relative molecular mass.

A "branched polymer" is a polymer that includes side chains of repeat units connecting onto the main chain of repeat units (different from side chains already present in the monomers). A branched polymer refers to a non-linear polymer structure, but typically, not a network structure. Therefore, a trace forward from the branch point would not bridge back to the original main chain; i.e. minimal to no backbone crosslinking is present. A branched polymer would generally be soluble in an appropriate solvent.

A "crosslinked polymer" is a polymer that includes interconnections between chains, either formed during polymerization (by choice of monomer) or after polymerization (by addition of a specific reagent). In a crosslinked polymer network, with the crosslinks serving as branch points, it is possible to trace a continuous loop back to the backbone. The crosslinked network would be insoluble in all solvents.

A "network polymer" is a crosslinked polymer that includes two or more connections, on average, between chains such that the entire sample is, or could be, a single molecule. Limited crosslink connections per chain would be considered lightly crosslinked while numerous crosslinks would be considered highly (or heavily) crosslinked.

A "copolymer" is a material created by polymerizing a mixture of two, or more, starting compounds. The resultant polymer molecules contain the monomers in a proportion which is related both to the mole fraction of the monomers in the starting mixture and to the reaction mechanism.

A "chain transfer agent" is an intentionally added compound that terminates the growth of one polymer chain and then reinitiates polymerization to create a new chain. A chain transfer agent is used as a way to limit chain length.

"Gelation time" is the time to reach the gel point (the point a which a continuous crosslinked network initially develops) during a polymerization.

A "filler" is a solid extender which may be added to a polymer to modify mechanical, optical, electrical, thermal, flammable properties, or simply to act as an extender. The filler can be reactive or inert in the polymerization.

An "extender" is a substance added to a polymer to increase its volume without substantially altering the desirable properties of the polymer.

The term "alkyl", "aliphatic" or "aliphatic group" as used herein means a straight-chain or branched $C_{1-20}$ hydrocarbon chain that is completely saturated or that contains one or more units of unsaturation, or a monocyclic $C_{3-8}$ hydrocarbon or bicyclic $C_{8-12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable alkyl groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkoxy," "hydroxyalkyl," "alkoxyalkyl" and "alkoxycarbonyl," used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The term "heteroatom" means nitrogen, oxygen, or sulfur and includes any oxidized form of nitrogen and sulfur, and the quaternized form of any basic nitrogen.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring". The term "aralkyl" refers to an alkyl group substituted by an aryl. The term "aralkoxy" refers to an alkoxy group substituted by an aryl.

A vinyl, or "-ene," functional group suitable for embodiments of the present invention includes any monomer having one or more vinyl functional groups, i.e., reacting "—C═C—" groups. Synonyms for a vinyl functional group include the terms olefinic group, alkenyl group, and ethylenic group.

As used herein, a "monovinyl monomer" is a monomer having one polymerizable double bond per molecule. The monovinyl monomer may comprise any monomer which can be polymerized by a free-radical mechanism such as (meth)acrylates and acrylates, styrene and derivatives thereof (styrenics), vinyl acetate, maleic anhydride, itaconic acid, N-alkyl (aryl) maleimides and N-vinyl pyrrolidone, vinyl pyridine, acrylamide, methacrylamide, N,N-dialkylmethacrylamides and acrylonitrile. Vinyl monomers, such as styrenics, acrylates and (meth)acrylates, (meth)acrylamides and acrylonitrile are preferred monomers. Mixtures of more than one monovinyl monomer may be used.

Examples of suitable acrylate monomers include alkyl acrylates such as methyl acrylate and ethylacrylate (EA). Examples of suitable monovinyl(meth)acrylate monomers include $C_1$-$C_{20}$ alkyl(meth)acrylates, preferably $C_1$-$C_8$, and more preferably $C_1$-$C_4$, such as, for example, methyl(meth)acrylate, ethyl(meth)acrylate (EMA), propyl(meth)acrylate, n-butyl(meth)acrylate, iso-butyl(meth)acrylate, t-butyl(meth)acrylate, 2-ethylhexyl(meth)acrylate octyl(meth)acrylate and dodecyl(meth)acrylate. Examples also include (meth)acrylamide monovinyl monomers. Other suitable monovinyl monomers include aromatic (meth)acrylates. These include, but are not limited to, 2-phenoxyethyl(meth)acrylate, phenyl(meth)acrylate, p-t-butylphenyl(meth)acrylate, p-methoxyphenyl(meth)acrylate, p-tolyl(meth)acrylate, p-cyclohexylphenyl(meth)acrylate, p-nitophenyl(meth)acrylate, and benzoyl(meth)acrylate. Also suitable are polycyclicaromatic (meth)acrylates such as 2-napthyl(meth)acrylate. In addition, (meth)acrylic acid is a suitable monovinyl monomer.

As used herein, a "functional monomer" is a monomer having one or more additional reactive groups available for further polymerization or reaction of the nanogel particles. Such monomers include methacrylic acid and acrylic acid or other —COOH containing monomers (these embodiments are particularly suited for use with dental adhesives, sealants, and other dental materials); hydroxy alkyl acrylates such as hydroxy ethylacrylate (HEA); hydroxy alkyl(meth)acrylates such as hydroxyethyl(meth)acrylate (HEMA), hydroxypropyl(meth)acrylate and hydroxybutyl(meth)acrylate; oxirane containing (meth)acrylates (epoxy(meth)acrylates) such as glycidyl(meth)acrylate, and dialkyl aminoalkyl(meth)acrylates such as dimethylaminoethyl(meth)acrylate, diethylaminoethyl(meth)acrylate, dimethyl aminopropyl(meth)acrylate and diethylaminopropyl(meth)acrylate; and norbornyl(meth)acrylate.

As used herein, a reactive olefinic compound contains at least one olefinic group and at least one additional reactive functional group such as a halogen, isocyanato or anhydride group. Exemplary reactive olefinic compounds include, but are not limited to, (meth)acryloyl chloride, (meth)acrylic anhydride, (meth)acrylic acid, isocyanatoalkyl(meth)acrylate, isocyanatoethyl(meth)acrylate vinylbenzene chloride, chloroethyl vinyl ether, allyl chloride and isocyanatomethyl(meth)acrylate.

Unless otherwise specified or implied, the term "(meth)acrylate" includes both the (meth)acrylate ($CH_2$═$C(CH_3)C$(═$O$)—) and the analogous acrylate ($CH_2$═$CHC$(═$O$)—).

As used herein, a "divinyl monomer" is a monomer having two polymerizable double bonds per molecule. Examples of suitable divinyl monomers include: ethylene glycoldi(meth)acrylate, tetraethyleneglycoldi(meth)acrylate (TEGDMA), the condensation product of bisphenol A and glycidyl(meth)acrylate, 2,2'-bis[4-(3-methacryloxy-2-hydroxy propoxy)phenyl]propane (bis-GMA), ethoxylated bisphenol-A-di(meth)acrylate, hexanediol di(meth)acrylate, tripropylene glycol di(meth)acrylate, butanediol di(meth)acrylate, neopentyl glycol di(meth)acrylate, diethylene glycol di(meth)acrylate, triethylene glycol di(meth)acrylate, dipropylene glycol di(meth)acrylate, allyl(meth)acrylate, divinyl benzene and derivatives thereof. A bis(meth)acrylamide, such as N,N-methylene bisacrylamide, could also be used as the divinyl component. Optionally, the divinyl monomer may comprise a mixture of more than one divinyl compound.

The branched polymer may also be formed using a reactive oligomer or reactive polymer or pre-polymer having at least two double bonds per molecule which are polymerizable via a free-radical mechanism as the, or one of the, divinyl monomers. Typical reactive oligomers include, but are not limited to, epoxy-(meth)acrylates, polyether(meth)acrylates, polyester-(meth)acrylates and urethane-(meth)acrylates. Typical reactive polymers include addition or condensation polymers such as a styrene or acrylic copolymers containing pendant polymerizable (meth)acrylate groups or unsaturated polyesters. The molecular weight range of the oligomer or reactive polymer may vary from 500-500,000 g/mole or more preferably from about 5,000 to 10,000 MW. In addition, trivinyl monomer successfully has been used as the crosslinker (trimethylolpropane tri(meth)acrylate). It is anticipated that tri-, tetra, and multi-(meth)acrylates are suitable in embodiments of the present invention. However, the avoidance of macrogelation is anticipated to be more of a problem with these compounds.

The divinyl or multivinyl monomer component can be selected such that the crosslinks formed within the nanogel can be intentionally reversible. By incorporation of a hydrolytically labile linkage or linkages that connect the polymerizable groups in the crosslinking monomer, the initially formed covalent crosslinks in the resultant polymer subsequently can be cleaved in a controllable manner by exposure of the nanogel particle to moisture. The outcome is that the crosslinked nanogel particle can be degraded to individual linear polymeric chains with molecular weight controlled based primarily on the chain transfer agent used in the nanogel synthesis. Other than the hydrolytic degradation mechanism, alternate degradable crosslinkers could be designed to degrade in response to temperature, pH, light, enzyme or other approaches.

Synthetic polymers have a distribution of molecular weights (MW, grams/mole). Polydispersity describes a polymer consisting of molecules with a variety of chain lengths and molecular weights. The width of a polymer's molecular weight distribution is estimated by calculating its polydispersity, Mw/Mn. The closer this approaches a value of 1, the narrower is the polymer's molecular weight distribution.

The weight-average molecular weight (Mw) is the average molecular weight of a polydisperse polymer sample, averaged to give higher statistical weight to larger molecules; calculated as Mw=SUM($Mi^2$ Ni)/SUM(Mi Ni). One technique used to measure molecular weights of polymers is light scattering. A light shining through a very dilute solution of a polymer is scattered by the polymer molecules. The scattering intensity at any given angle is a function of the second power of the molecular weight. Consequently, because of this "square" function, large molecules will contribute much more to the molecular weight that we calculate than small molecules.

Figure 21:
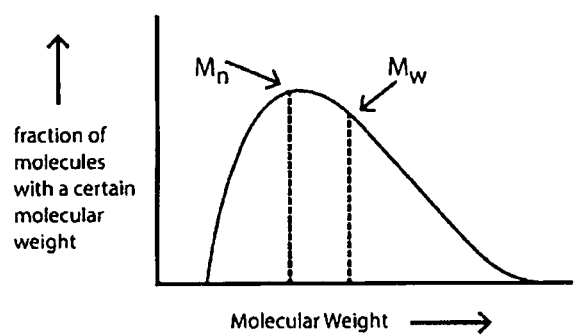
FIG. 21 is a graph depicting the fraction of molecules having a certain molecular weight as a function of molecular weight.

The number-average molecular weight (Mn) is the average molecular weight of a polydispersed polymer sample, averaged to give equal statistical weight to each molecule; calculated as Mn=SUM(Mi Ni)/SUM(Ni) (see FIG. 21).

The hydrodynamic radius is the radius of a particle or polymer molecule in solution that is determined from a measurement of mobility or diffusion, for example in viscosity or dynamic light scattering experiments. The diffusion coefficient, D is related to the viscosity $\eta$ and the hydrodynamic radius, $R_H$ by: $D=k_B T/6\pi\eta R_H$; where $k_B$ is the Boltzmann constant and T is the absolute temperature.

A. Nanogel Compositions

The copolymerization of monovinyl and multivinyl monomers typically leads to macroscopically crosslinked polymeric networks, which are often referred to as macrogels. At a very early stage of these crosslinking polymerizations, the continuous network structure is formed and the polymer becomes insoluble in all solvents. Embodiments of the present invention provide methods for controlling the polymerization process through use of chain transfer agents to yield shorter polymer chains that either delay macrogelation significantly or avoid it altogether, even at high degrees of monomer conversion. In one aspect, the molecular weight of the nanogel increases as the amount of chain transfer agent decreases. The resulting nanogel, which has internal cyclized and crosslinked structure but lacks macroscopic connectivity between the discrete particles, is soluble in appropriate solvents.

Figure 5:
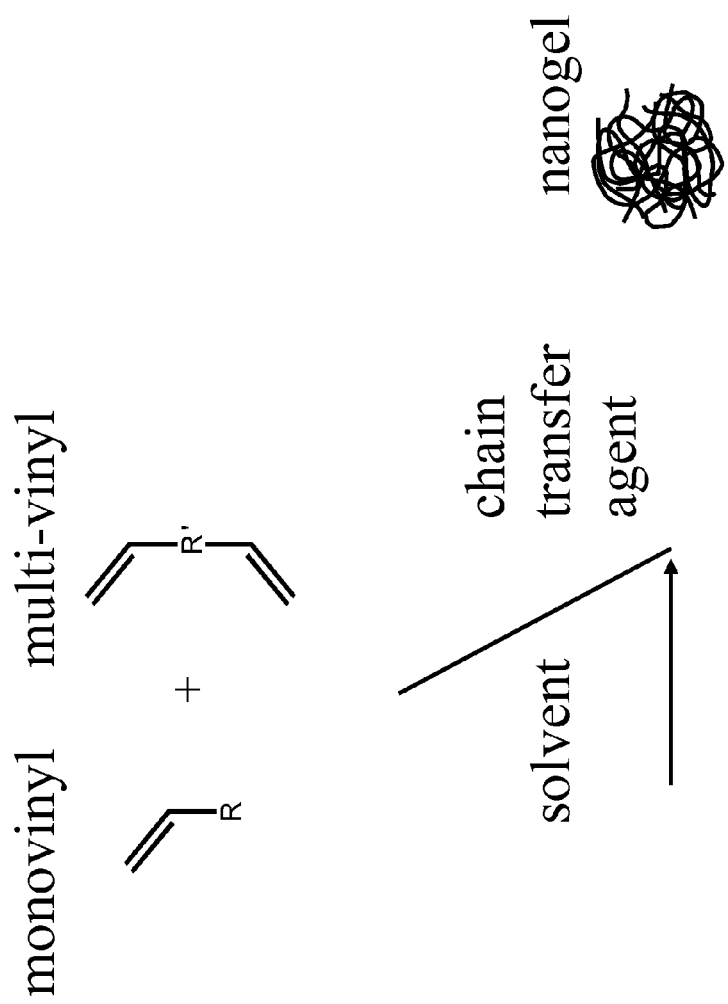
FIG. 5 shows a reaction diagram of the basic nanogel formation reaction.

FIG. 5 illustrates a reaction of a monovinyl monomer and multivinyl monomer using a chain transfer agent to yield a soluble nanogel. This reaction may either be carried out in solution or in bulk. In the figure, R is a monovinyl and R' is a multivinyl.

Nanogels can be approximated as dendritic or hyperbranched polymers since they can have continuously branching, connected structures. In network forming free radical chain polymerizations, the transient nanogel stage, which precedes macrogelation, is indicative of heterogeneous polymerization processes involving cyclization reactions and differential reactivities of free and pendant vinyl groups. Nanogels arise in di- or multi-vinyl polymerizations or in copolymerizations of these multifunctional monomers with monovinyl monomers. The incorporation of divinyl monomers in a polymerization generally results in crosslinked polymer formation. Crosslinked or macrogel polymers are by definition infinite molecular weight structures that are insoluble in any solvent. Macrogel polymers exist when the average number of crosslinks per chain exceeds two. In monovinyl/divinyl copolymerizations, the critical conversion (pc) at which gelation occurs can be predicted. In practice, the observed gel points are usually higher than the theoretical calculations because of cyclization reactions that decrease the productive crosslink density. A chain transfer agent is required to controllably limit the length of the propagating chain such that bridging between growing nanogel regions is eliminated and the resulting high molecular weight polymeric nanogels are soluble.

According to the present invention, higher concentrations of the divinyl monomer can be used—up to the limit of exclusively using a divinyl monomer in the nanogel synthesis. This provides a unique method to use conventional free radical polymerization chemistry and conventional (meth) acrylate monomers to produce hyperbranched polymeric structures.

The polymerization of the monomer mixture may be performed using any free-radical polymerization method, e.g. solution, suspension, emulsion and bulk polymerization methods may all be used. For many applications of the branched polymers of the invention, the material is required in solid form. For these applications, polymers made by solution polymerization require the solvent to be removed before use. This increases the cost and it is difficult to remove all of the solvent providing deficiencies in utilization of the polymer. Alternatively when the polymer is required for use in solution form, it is necessary to conduct the polymerization in the solvent which is to be present in the end-use application if the step of isolating the polymer is to be avoided. Therefore it may be advantageous to produce the branched polymer by a non-solution method, e.g. suspension or bulk polymerization.

The chain transfer agent may be chosen from a range of thiol compounds including monofunctional and multifunctional thiols. Monofunctional thiols include, but are not limited to, propyl mercaptan, butyl mercaptan, hexyl mercaptan, octyl mercaptan, dodecyl mercaptan (docecanethiol, DDT), thioglycolic acid, methylbenzenethiol, dodecanethiol, mercaptopropionic acid, alkyl thioglycolates e.g. 2-ethyl hexyl thioglycolate or octylthioglycolate, mercaptoethanol, mercaptoundecanoic acid, thiolactic acid, thiobutyric acid. Multifunctional thiols include trifunctional compounds such as trimethylol propane tris(3-mercaptopropionate), tetrafunctional compounds such as pentaerythritol tetra(3-mercaptopropionate), pentaerythritol tetrathioglycolate, pentaerythritol tetrathiolactate, pentaerythritol tetrathiobutyrate; hexafunctional compounds such as dipentaerythritol hexa(3-mercaptopropionate), dipentaerythritol hexathioglycolate; octafunctional thiols such as tripentaerythritol octa(3-mercaptopropionate), tripentaerythritol octathioglycolate. The use of multifunctional thiols is a useful way to increase the degree of branching in the polymer. A difunctional chain transfer agent contains at least one thiol and at least one hydroxyl group. Examples of difunctional chain transfer agents include mercaptoethanol, mercaptopropanol, 3-mercapto-2-butanol, 2-mercapto-3-butanol, 3-mercapto-2-methyl-butan-1-ol, 3-mercapto-3-methyl-hexan-1-ol and 3-mercaptohexanol. Optionally, the chain transfer agent may comprise a mixture of more than one type of compound.

The amount of chain transfer agent present may be up to 50 wt % of the total initial monomer concentration. In a first embodiment, the amount of chain transfer agent present is 0.1-20% w/w, e.g. 0.5-10% w/w based on total monomer in the monomer mixture. The branched polymer is made using an appropriate amount of chain transfer agent to prevent the formation of a substantial amount of insoluble cross-linked polymer. The majority of the polymer produced is soluble, even at high conversion of monomer to polymer. A small amount of cross-linked polymer may be formed but the reaction conditions and level of chain transfer agent should preferably be chosen such that the amount of cross-linked polymer formed is at most about <10% (w/w), more preferably about <5% (w/w), more preferably about <2.5% (w/w) and optimally about 0% (w/w). For certain polymerization systems, the use of secondary mercaptan chain transfer agents may be preferred. Chain transfer agents comprising secondary mercaptans are particularly preferred when the polymerization is carried out in bulk or suspension polymerization processes.

Alternative chain transfer agents may be any species known to reduce molecular weight in the conventional free-radical polymerization of vinyl monomers. Examples include sulphides, disulphides, halogen-containing species. Also, catalytic chain transfer agents such as cobalt complexes, e.g. cobalt (II) chelates such as cobalt porphyrin compounds are useful chain transfer agents for the invention. Suitable cobalt chelates are known in the art and are described in WO 98/04603. A particularly suitable compound is bis(borondifluorodimethylglyoximate) cobaltate (II) also known as CoBF. Catalytic chain transfer agents may be used in relatively low concentrations compared to conventional thiol chain transfer agents, e.g. <0.5% preferably <0.1% by weight (on monovinyl monomer), since they are generally highly effective at low concentrations.

The polymerization of the monomers may be initiated by any suitable method of generating free-radicals such as by thermally induced decomposition of a thermal initiator such as an azo compound, peroxide or peroxyester. Alternatively, redox initiation or photo-initiation can be used to generate the reactive free radicals. Therefore the polymerization mixture also preferably contains a polymerization initiator which may be any of those known and conventionally used in free-radical polymerization reactions, e.g. azo initiators such as azobis (isobutyronitrile) (AIBN), azobis(2-methylbutyronitrile), azobis(2,4-dimethylvaleronitrile), azobis(4-cyanovaleric acid), peroxides such as dilauroyl peroxide, tert-butyl peroxyneodecanoate, dibenzoyl peroxide, cumyl peroxide, tert-butyl peroxy-2-ethyl hexanoate, tert-butyl peroxy diethyl acetate and tert-butyl peroxy benzoate. In a specific aspect, the thermal initiator is AIBN.

In another aspect, the initiator is a redox (reduction-oxidation) pair of initiators. Redox initiator systems use both a primary initiator and a chemical reducing agent. Several types of redox initiator pairs are known such as persulfite-bisulfite, persulfate-thiosulfate, persulfate-formaldehyde sulfoxylate, peroxide-formaldehyde sulfoxylate, peroxide-metallic ion (reduced), persulfate-metallic ion (reduced), benzoyl peroxide-benzene phosphinic acid, and benzoyl peroxide-amine wherein the amine acts as the reducing agent. The redox pair may be selected from any known redox pair such as a combination of benzoyl peroxide and dimethyl-p-toluidine, AMPS (ammonium persulfate) and TEMED (tetramethyl ethylene diamine), sulfur dioxide and ter-butyl hydroperoxide, potassium persulfate and acetone sodium bisulfite. In a specific aspect, the redox initiator pair is 1 wt % benzoyl peroxide with 1.5 wt % dimethyl-p-toluidine amine coinitiator.

In a one aspect, the initiator is a photoinitiator. The photoinitiator can be selected from one or more known photoinitiators. For example, the initiator can be selected from one or more of an alpha-hydroxyketone, an acyl phosphine oxide, a benzoyl peroxide with or without an amine co-initiator. Any known photoinitiator, or combination of one or more photoinitiators can be employed. For example, the photoinitiator can be selected from one or more acyl phosphine oxides such as BAPO (bis-acylphosphine oxide), phenyl-bis(2,4,6-trimethylbenzoyl)phosphine oxide, TPO (2,4,6-trimethylbenzolyldiphenylphosphine oxide), bis-trimethoxybenzoyl-phenylphosphine oxide, TPO-L (2,4,6-trimethylbenzoylphenyl phosphinate), or MAPO (tris[1-(2-methyl)aziridinyl]phosphine oxide. Other photoinitiators may be employed alone or in combination including, but not limited to, DMPA (2,2-dimethoxy-2-phenylacetophenone), BDK (benzil dimethylketal), CPK (cyclohexylphenylketone), HDMAP (2-hydroxy-2-methyl-1-phenyl propanone), ITX (isopropylthioxanthrone), HMPP (hydroxyethyl-substituted alpha-hydroxyketone), MMMP (2-methyl-4'-(methylthio)-2-morpholinopropiophenone), BDMB (2-benzil-2-dimethylamino-1-(4-morpholinophenyl)-butanone-1), BP (Benzophenone), TPMK (methylthiophenyl-morpholinoketone), 4-Methylbenzophenone, 2-Methylbenzophenone, 1-Hydroxy cyclohexyl phenyl ketone, 2-Benzyl-2-(dimethylamino)-1-[4-(4-morpholinyl)phenyl]-1-butanone, Diphenyl Iodonium Hexafluorophosphate, Bis (p-tolyl) iodonium hexafluorophosphate, 2-Methyl-1-[4-(methylthio)phenyl]-2-morpholinopropanone-1,2-Hydroxy-2-methyl-phenyl-propan-1-one, 1,7-bis(9-acridinyl)heptane, 2-Hydroxy-4'-hydroxyethoxy-2-methylpropiophenone, 2,2'-Bis(O-chlorophenyl-4,4',5,'-tetraphenyl-1,2'-diimidazole, 9-Phenylacridine, N-phenylglycine, 2-(4-methoxyphenyl-4, 6-bis(trichloromethyl)-1,3,5-triazine, P-toluene sulfonylamine, Tris-(4-dimethylaminophenyl)methane, Tribromo methyl phenyl sulfone, 2,4-Bis(trichloromethyl)-6-(p-methoxy)styryl-s-triazine, 2,4-Bis(trichloromethyl)-6-(3,4-dimethoxy)styryl-s-triazine, 4-(2-aminoethoxyl)methyl benzophenone, 4-(2-hydroxyethoxyl)methyl benzophenone, 2-Isopropylthioxanthone, 4-Isopropylthioxanthone, 4-Hydroxy benzophenone, 4-Methyl acetophenone, 4-(4-Methylphenylthiophenyl)-phenylmethanone, dimethoxyphenylacetophenone, camphorquinone, 1-Chloro-4-propoxythioxanthone, 2-Chlorothioxanthone, 2,2-Diethoxyacetophenone, 2,4-Diethylthioxanthone, 2-Dimethyl-aminoethylbenzoate, 2-Ethylhexyl-4-dimethylaminobenzoate, Ethyl-4-(dimethylamino)benzoate, 2-Isopropylthioxanthone, Methyl o-benzoyl benzoate, Methyl phenyl glyoxylate, 4,4'-Bis(diethylamino)benzophenone, 4-Phenylbenzophenone, 2,4,6- and Ethyl (2,4,6-trimethylbenzoyl)phenylphosphinate.

The polymerization photoinitiators are used in amounts effective to initiate polymerization in the presence of the curing radiation, typically about 0.01 to about 10 wt %, and more specifically about 0.05 to about 7 wt %, and more specifically, about 0.1 to about 5 wt %, based on the total weight of the composition.

The photoinitiator composition can optionally further contain a coinitiator for example, EHA (2-ethyl hexylacrylate) or an amine coinitiator such as, for example, ethyl-4-(dimethylamino)benzoate, 2-ethylhexyl dimethylaminobenzoate, dimethylaminoethyl(meth)acrylate, or the like. Reactive amine polymerization coinitiators can be used, such as the coinitiator CN386 (a reactive amine adduct of tripropylene glycol diacrylate), commercially available from Sartomer, Darocure EHA, or commercially available from Ciba, and the like. The coinitiator can be present in the composition in an amount of about 0.25 to about 20 wt %, specifically about 1 to about 10 wt %, and more specifically about 1 to about 5 wt %, based on the total weight of the composition. In a specific aspect the initiator is BAPO bis-acyl phosphine oxide commercially available, for example, as Irgacure from Ciba.

In one embodiment, the disclosure provides a soluble nanogel polymer produced by polymerization of a monomer mixture comprising a monovinyl monomer, a multivinyl monomer, and an iniferter. Iniferters are initiators that induce radical polymerization that proceeds via initiation, propagation, primary radical termination, and transfer to initiator. Because bimolecular termination and other transfer reactions are negligible, these polymerizations are performed by the insertion of the monomer molecules into the iniferter bond, leading to polymers with two iniferter fragments at the chain ends. The use of well-designed iniferters would give polymers or oligomers bearing controlled end groups. If the end groups of the polymers obtained by a suitable iniferter serve further as a polymeric iniferter, these polymerizations proceed by a living radical polymerization mechanism in a homogeneous system. For example, the iniferters (e.g., C—S bond) are considered a dormant species of the initiating and propagating radicals. From the viewpoint of controlled polymer synthesis, iniferters can be classified into several types: thermal iniferters or photoiniferters; monomeric, polymeric, or gel iniferters; monofunctional, difunctional, trifunctional, or polyfunctional iniferters; monomer or macromonomer iniferters; and so forth. These lead to the synthesis of various monofunctional, telechelic, block, graft, star, and crosslinked polymers. Otsu, "Iniferter concept and living radical polymerization" J Polym Sci A: Polym Chem 38: 2121-2136, 2000.

Photoiniferters include, but are not limited to, diphenyldisulfide, benzyl N,N-diethyldithiocarbamate, tetraethylthiuram disulfide, phenyltriphenylazomethane, isopropylxanthic disulfide, p-xylylene bis-N,N-diethyldithiocarbamate, and benzyl dithiocarbamate.

Thermal iniferters include, but are not limited to, N-bromosuccinimide (NBS), diethyl-2,3-dicyano-2,3-di(p-tolyl) succinate (DCDTS), and phenylazotriphenyl methane (APT). Some compounds such as diethyl 2,3-dicyano-2,3-di(p-N,N-diethyldithiocarbamylmethyl)phenyl-succinate (DDDCS) can act as both a photoiniferter as well as a thermal iniferter. Qin et al., "Radical polymerization of styrene initiate with a new multifunctional iniferter" Polymer Bull. 44, 123-128, 2000.

Conventional free radical photoinitiators, such as benzophenone and dimethoxyphenylacetophenone, which are active in the UV wavelength range, or bis(trimethylbenzoyl) phenylphosphine oxide and camphorquinone/amine, which function within the visible light region, typically interact with monomer only at the initiation stage.

Free radical formation must be maintained throughout the photopolymerization process to provide a continuous source of initiating radicals to replenish the efficient consumption of radicals associated with the biradical termination process, which deactivates growing polymer chains. This means that radical photopolymerizations are irradiated until all the reactive monomer groups are consumed or that limiting polymer conversion is achieved. The typical lifetime of a radical is only on the order of 0.1-10 seconds during which time, hundreds or thousands of monomer propagation events occur prior to termination. Thus, high molecular weight polymer chains rapidly form, grow and die with high turnover as the initiation, propagation and termination processes all occur simultaneously during active polymerization. If exposure to the light source is interrupted, new radical formation is eliminated from the equation and additional propagation ends quickly due to quick depletion of active radical chains based on termination. If the photopolymerization is interrupted without complete consumption of both the initiator and the monomer, the polymerization can be restarted but with new chains being formed.

A photoiniferter behaves differently than a conventional free radical photoinitiator where the concentration of active radical centers is restricted by an equilibrium between the active free radical and the dormant state based on a photoreversible termination involving the thiyl radical. In the presence of a photoiniferter, chain growth continues without significant irreversible termination while irradiation continues. The dormant state predominates in the absence of light and the polymerization process can be reactivated by re-exposure where the pre-existing polymer chains are able to continue to grow rather than new chains starting.

Photoiniferters are considered examples of living or controlled radical polymerization since polymer chains grow during irradiation, reversibly terminate in the dark and can be reactivated upon re-exposure. However, the process is clearly dependent on continuous or sequential light exposure and dark cure is extremely limited, just as in conventional photoinitiated radical systems.

Advantages to the use of an iniferter in nanogel production methods include the ability to more precisely tailor the size of the nanogel; and enhanced uniformity of size, or equivalent diameter, of the nanogel.

In one aspect, an iniferter is used to restrict active radicals to the nanogel surface, such that only monomer can be added to the nanogel surface.

In another aspect, an iniferter is used to prepare a reactive nanogel with pendant (meth)acrylate groups at the nanogel surface in a single reaction step. In this aspect, the reactive nanogel is prepared by combining a monomer mixture comprising at least one monovinyl monomer, at least one divinyl monomer, a chain transfer agent, an iniferter, and an initiator and polymerizing to form a reactive nanogel with pendant (meth)acrylate groups at the nanogel surface. In one aspect, a stoichiometric excess of the divinyl monomer is utilized in the monomer mixture as compared to the monovinyl monomer.

In a further aspect, an iniferter is used to prepare a living nanogel, which may be derivitized at its surface by secondary addition of a monomer without further initiator.

In one aspect, one or more iniferters can be used alone or in combination with one or more other initiators. Iniferters for use in the present invention include, but are not limited to, diphenyldisulfide, benzyl N,N-diethyldithiocarbamate, tetraethylthiuram disulfide, phenyltriphenylazomethane, and methacryloyl-O-ethyl xanthate. In a specific aspect, the iniferter tetraethylthiuram disulfide (TED) is used in combination with the photoinitiator DMPA.

In the preparation of the nanogels of the invention, one or more monovinyl monomers may be mixed with a divinyl monomer, for example, ethylacrylate (EA) may be mixed with tetraethyleneglycol di(meth)acrylate (TEGDMA). The molar ratio of monovinyl monomer to divinyl monomer may vary from about 100:0 to about 0:100. It is preferred that the molar ratio of monovinyl monomer to divinyl monomer be from about 100:10 to about 100:100. The molar ratio of nonfunctional monovinyl monomer to functional monovinyl monomer may vary from 100:0 to 0:100. In a preferred embodiment, the monovinyl monomer is a mixture of nonfunctional monovinyl monomer and functional monovinyl monomer. For example, 5 mole % HEMA was mixed with 95 mole % EMA with 2% TEGDMA to make the monomer mixture, and 2% $C_{12}SH$, and 1% AIBN in toluene added.

In embodiments, the amount of multivinyl used is at least about 5 mol %, more preferably about 10 mol %, more preferably about 15 mol %, more preferably about 25 mol %, more preferably about 50 mol %, more preferably about 75 mol %, more preferably about 100 mol %, i.e. the monomer mixture contains only multivinyl monomers and no monovinyl monomers. In one aspect, the molecular weight of the nanogel increases with the level of multivinyl monomer used in the nanogel synthesis.

A suitable chain transfer reagent, for example dodecane thiol ($C_{12}SH$), can be added to the reaction at about 1 to about 2 mole percent with respect to the monovinyl monomer. A suitable free radical initiator may also be added, for example 2,2'-azobisisobutyronitrile (AIBN) may be added to the reaction mixture in a ratio of from about 0.5 to 2 mole percent with respect to the monovinyl monomer.

The nanogels can be prepared in the presence or absence of a solvent. It is advantageous to use a substantially inert solvent, i.e. one that does not participate in the reaction. Suitable solvents are all solvents which dissolve the monomers used, for example, water, alcohols such as lower alkanols like ethanol or methanol, carboxamides such as dimethylformamide, dipolar aprotic solvents such as dimethyl sulfoxide or methyl ethyl ketone, ketones such as acetone, 2-butanone, or cyclohexanone, hydrocarbons such as toluene and xylene, ethers such as THF, dimethoxyethane or dioxane, halogenated hydrocarbons such as trichloroethane, and mixtures of suitable solvents such as mixtures of water and an alcohol, for example, a water/ethanol or water/methanol mixture. In one aspect, nanogel molecular weight increases with decreasing solvent concentration. In another aspect, a particular nanogel preparation can be more efficient in one solvent system than another, even at the same solvent concentration, as shown in Table 16.

The reaction temperature can be, for example, from −60° C. to 150° C., preferably from 65° C. to 90° C. The reaction times are in the range from about 15 minutes to 7 days, preferably in the region of about 2 to 48 hours. If necessary, the reaction is carried out under argon or nitrogen as protective gas.

By way of general example, the monomers, crosslinking agent, initiator and solvent are introduced into a suitable mixing vessel. The solution is degassed by passing nitrogen gas through the solution. The solution is then heated at about 85° C. for approximately 4 to 24 hours. The solvent is then removed under vacuum to obtain the nanogel product which is then purified by change of solvent such as $CH_2Cl_2$ and/or hexane.

B. Functionalized Nanogels

The present invention further provides functionalized nanogels whereby a portion or all of the monovinyl monomer is replaced with a functional monomer. The functionality can be used to covalently attach other functional groups to the polymer. This effectively turns the nanogel into an oligomer that can be copolymerized with other comonomers. Thus, reactive groups on the comonomer can be used, for example, to yield an insoluble, fully crosslinked network.

The functionality should survive the initial polymerization such that it can either be utilized directly in a controlled second-stage polymerization or be utilized as a means to introduce new reactive groups that can then take part in a secondary polymerization reaction. For example: 1) the hydroxyl functionality in HEMA or HEA can be used with di- or (multi-)isocyanate to form final polymer in a second stage polymerization; 2) norbornyl(meth)acrylate can undergo secondary polymerization; 3) vinyl or allyl ether functionality also could be used directly in a secondary cationic polymerization; 4) glycidyl(meth)acrylate, and other oxirane derivitized (meth)acrylates, are capable of ring-opening polymerization based on a cationic or amine-based reaction scheme.

In the example of hydroxyl group functionalized nanogels, this functionality can be used in a second reaction to introduce new (meth)acrylate reactive groups by a reactive (meth)acryloyl compound selected from (meth)acryloyl chloride, (meth)acrylic anhydride, (meth)acrylic acid or an isocyanatoalkyl (meth)acrylate. The isocyanato alkyl(meth)acrylate can be selected from, for example, isocyanatoethyl(meth)acrylate or isocyanatomethyl(meth)acrylate. In this manner, all or any portion of the available hydroxyl functional groups can be converted to polymerizable (meth)acrylate groups to yield a nanogel macromonomer.

Functional monomers include hydroxyl-containing materials which can be any organic material having hydroxyl functionality of at least 1, and preferably at least 2. Preferably the hydroxyl-containing material contains two or more primary or secondary aliphatic hydroxyl groups (i.e., the hydroxyl group is bonded directly to a non-aromatic carbon atom). The hydroxyl groups can be terminally situated based on hydroxyl-containing thiols (2-mercaptoethanol), or they can be pendent from a polymer or copolymer based on hydroxyl-substituted monomers such as HEMA or Bis-GMA. The molecular weight of the hydroxyl-containing organic material can vary from very low (e.g., 32) to very high (e.g., one million or more). Suitable hydroxyl-containing materials can have low molecular weights, i.e., from about 32 to 200 g/mol, intermediate molecular weight, i.e., from about 200 to 10,000, or high molecular weight, i.e., above about 10,000. As used herein, all molecular weights are weight average molecular weights.

Suitable hydroxyl group and/or carboxyl group-containing acrylic polymers can be prepared from polymerizable ethylenically unsaturated monomers and are typically copolymers of (meth)acrylic acid and/or hydroxylalkyl esters of (meth)acrylic acid with one or more other polymerizable ethylenically unsaturated monomers such as alkyl esters of (meth)acrylic acid including methyl(meth)acrylate, ethyl(meth)acrylate, butyl(meth)acrylate and 2-ethyl hexylacrylate, and vinyl aromatic compounds such as styrene, alpha-methyl styrene, and vinyl toluene.

The hydroxyl-containing material can optionally contain other functionalities, such as nonaromatic and aromatic functionalities. The hydroxyl-containing material can optionally contain heteroatoms in the backbone of the molecule, such as nitrogen, oxygen, sulfur, and the like. The hydroxyl-containing material can, for example, be selected from naturally occurring or synthetically prepared cellulosic materials. Useful hydroxyl-containing materials are described, for example, in U.S. Pat. No. 5,856,373, which is incorporated herein by reference.

Blends of various hydroxyl-containing materials may also be used. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

The nanogel structure can also be altered through surface modification of nanogel structures or by forming compositional gradients within the nanogel. For example, the surface of a hydrophobic nanogel can be modified by introduction of a hydrophilic monomer in the final stages of nanogel synthesis. A nanogel prepared with ethyl(meth)acrylate and tetraethylene glycol di(meth)acrylate is relatively hydrophobic. This material will separate out of water. However, if the same nanogel is further modified by a second stage reaction with poly(ethylene glycol) mono(meth)acrylate and tetraethylene glycol di(meth)acrylate, a stable aqueous suspension of the nanogel can be prepared. This provides a means to dramatically improve water solubility of the nanogel, which has implications for the use of nanogels in tissue engineering or drug delivery applications. The nanogels can also be constructed with rigid core and more flexible, less highly crosslinked surface boundaries. In a similar approach as the previous example, the nanogels can be prepared in stages or even as gradient materials. Since the nanogel particles form early and then grow throughout the synthesis, the nanogels can be started with one composition which is then changed in a step-wise or continuous gradient fashion as the synthesis proceeds. This allows a different surface composition compared with the core. Thus, by using more crosslinker (divinyl) or a more rigid monovinyl monomer initially, a nanogel with a higher modulus core could be created.

To illustrate, the nanogel preparation comprising ethyl (meth)acrylate, tetraethylene glycol di(meth)acrylate and a chain transfer agent was modified by the substitution of a small amount of 2-hydroxyethyl(meth)acrylate (HEMA, 5 mol %) for a portion of the monovinyl component. The resulting random incorporation of HEMA into the polymeric nanogel, which could be verified by IR and NMR analyses, provides access to hydroxy-appended nanogels that can then be used to covalently attach other functional groups to the polymer. In one example, the polyol functionalized nanogel was reacted with methacryloyl chloride to reintroduce polymerizable (meth)acrylate groups and thus create a macromonomer (macromer). Just as the synthesis of the nanogels can be controlled to yield particles of a given size, molecular weight and structural architecture, the degree of post-polymerization derivatization can also be readily manipulated to alter the density of reactive groups introduced in the macromer. The soluble macromer can then be further polymerized to yield an insoluble, fully cross-linked infinite network based on the second polymerization step involving only the added reactive groups.

The approach of using nanogel additives to modify the properties of a secondary monomer or resin is attractive for its potential to increase strength and toughness or to reduce polymerization shrinkage and stress development. There are additional advantages to the use of nanogel modifiers. There are a wide variety of monomers that present practical problems for general use. For example, in dental material applications, acrylates are avoided since they present cytotoxic response when used in applications where free monomer is in direct contact with cells and tissues. Another problem is encountered when volatile monomers are used in open environments. In this case, the high vapor pressure monomers, such as methyl(meth)acrylate, acrylic acid or styrene, can be efficiently incorporated into the nanogel structure in whatever composition is preferred. In the prepolymerized nanogel, the volatility as well as toxicity issues are circumvented and the properties associated with the particular target monomer can be introduced into the secondary monomer matrix with control of the nanogel composition and concentration as simple adjustable parameters. While we have considered the use of nanogels to convey radioopacity to secondary polymers, the addition of nanogel can also effectively be used to alter the refractive index of the secondary monomer as well as its polymer.

C. Use of Nanogels as Dental Fillers

One exemplary embodiment of the nanogels of the present invention is a dental filler that can take the place of typical dental fillers in dental restorative compositions. Nanogels can also be used to take the place of dental resin, and thus proportionately require less dental resin than is typically necessary in a resin-filler dental restorative composition. In dentistry, dental restorative compositions typically include silanized filler compounds such as barium, strontium, zirconia silicate and/or amorphous silica to match the color and opacity to a particular use or tooth and also to increase the volume of the restorative composition. Organic dental fillers are also common.

In embodiments of the present invention, dental composites are formulated by mixing the nanogel fillers with other dental monomers and necessary additives. Dental composites may be fabricated and characterized in order to improve mechanical properties, wear-resistance, water hydrolytic stability and reduced polymerization shrinkage and stress. Embodiment of the present invention further provides dental resins comprising functionalized and non-functionalized nanogels as dental fillers. The dental fillers of the present invention yield substantially reduced polymerization shrinkage. The nanogels are readily dissolvable in the resins and do not materially affect viscosity of the resulting product mixture. As noted above, embodiments of nanogels derived from monomers, such as methacrylic acid or other —COOH containing monomers, are particularly suited for use with dental adhesives, sealants and other dental materials.

Preferably the dental fillers comprise 10-50% wt/wt of the nanogels. More preferably, 15% to 40%, and most preferably 15% to 30%.

The polymeric matrix portion of the dental composite is selected from those known in the art of dental materials, including but not being limited to expandable monomers, liquid crystal monomers, ring-opening monomers, polyamides, acrylates, polyesters, polyolefins, polyimides, polyarylates, polyurethanes, vinyl esters or epoxy-based materials. Other polymeric matrices include styrenes, styrene acrylonitriles, ABS polymers, polysulfones, polyacetals, polycarbonates, polyphenylene sulfides, and the like. These polymeric matrices are derived from curing polymeric matrix precursor compositions. Such precursor compositions are well-known in the art, and may be formulated as one-part, two-part, or other compositions, depending on the components.

Preferred materials include those based on acrylic and methacrylic monomers, for example those disclosed in U.S. Pat. Nos. 3,066,112, 3,179,623, and U.S. Pat. No. 3,194,784 to Bowen; U.S. Pat. Nos. 3,751,399 and 3,926,906 to Lee et al.; and commonly assigned U.S. Pat. No. 5,276,068 to Waknine and U.S. Pat. No. 5,969,000 to Yang, all of which are herein incorporated by reference. Especially preferred di(meth)acrylate monomers include bis-GMA, the condensation product of bisphenol A and glycidyl(meth)acrylate, ethoxylated bisphenol A di(meth)acrylate (EBPA-DMA), and the condensation product of 2 parts hydroxyethyl(meth) acrylate and 1 part triethylene glycol bis(chloroformate) (PCDMA). Urethane di(meth)acrylate (UDMA) is also a commonly-used principal di(meth)acrylate monomer suitable for use in the present invention.

The polymeric matrix precursor composition may further comprise a co-polymerizable diluent monomer. Such monomers are generally used to adjust the viscosity of the polymerizable composition, which affects wettability of the composition. Suitable diluent monomers include, without limitation, hydroxyalkyl(meth)acrylates, such as 2-hydroxyethyl(meth)acrylate, 1,6-hexanediol di(meth)acrylate, and 2-hydroxypropyl methacrtylate; glyceryl di(meth)acrylate; ethyleneglycol(meth)acrylates, including ethyleneglycol (meth)acrylate, diethyleneglycol di(meth)acrylate, triethyleneglycol di(meth)acrylate and tetraethyleneglycol di(meth) acrylate; or diisocyanates, such as 1,6-hexamethylene diisocyanate. Triethyleneglycol di(meth)acrylate (TEGDMA) is particularly preferred for use in the present invention.

The polymeric matrix precursor composition typically includes polymerization initiators, polymerization accelerators, ultra-violet light absorbers, anti-oxidants, fluorescent whitening agents, and other additives well known in the art. The polymer matrices may be visible light curing, self-curing, dual curing, and vacuum-, heat-, and pressure-curable compositions as well as any combination thereof. Visible light curable compositions employ light sensitive compounds such as benzil diketones, and in particular, dl-camphoquinone in amounts ranging from about 0.05 to 0.5 weight percent. UV absorbers are particularly desirable in the visible light curable compositions in order to avoid discoloration of the resin form any incident ultraviolet light. Suitable UV absorbers are the various benzophenones, particularly UV-9 and UV-5411 available from American Cyanamid company, and benzotriazoles known in the art, particularly 2-(2'-hydroxy- 5'-methylphenyl)-benzotriazole, sold under the trademark TINUVIN P by Ciba-Geigy Corporation, Ardsley, N.Y. in amounts ranging from about 0.05 to about 5.0 weight percent.

In the self-curing compositions, a polymerization accelerator may be included in the polymerizable monomer composition. The polymerization accelerators suitable for use include the various organic tertiary amines well known in the art, generally aromatic tertiary amines, such as dimethyl-p-toluidine, dihydroxyethyl-p-toluidine and the like, in amounts ranging from about 0.05 to about 4.0 weight percent, and generally acrylate derivatives such as dimethylaminoethyl(meth)acrylate and particularly, diethylaminoethyl(meth)acrylate in amounts ranging from about 0.05 to 0.5 weight percent.

The heat and pressure curable compositions include, in addition to the monomeric components, a heat cure initiator such as benzoyl peroxide, 1,1'-azobis(cyclohexanecarbonitrile), or other suitable free radical initiators. Particularly suitable free radical initiators are lauroyl peroxide, tributyl hydroperoxide, 2,2'-azobisisobutyronitrile ("AIBN") and, more particularly benzoyl peroxide or 1,1'-azobis(cyclohexanecarbonitrile).

The dental materials of the present invention may optionally comprise additional adjuvants suitable for use in the oral environment, including colorants, flavorants, anti-microbials, fragrance, stabilizers, viscosity modifiers and fluoride releasing materials. For example, a fluoride releasing glass may be added to the materials of the invention to provide the benefit of long-term release of fluoride in use, for example in the oral cavity. Fluoroaluminosilicate glasses are particularly preferred. Particularly preferred are silanol treated fluoroaluminosilicate glass fillers, as described in U.S. Pat. No. 5,332,429, the disclosure of which is expressly incorporated by reference herein. Other suitable adjuvants include agents that impart fluorescence and/or opalescence.

In a preferred method of using the dental material of the invention, comprising a hardenable resin and fillers of the invention, the material is placed near or on a tooth surface, followed by a manipulation by the practitioner or laboratory to change the topography of the material, then hardening the resin. These steps can be followed sequentially or in a different order. For example, in a preferred embodiment where the dental material is a mill blank or prosthesis, the hardening step is generally completed prior to changing the topography of the material. Changing the topography of the material can be accomplished in various ways, such as carving or manual manipulation using hand held instruments, or by machine or computer aided apparatus, such as a CAD/CAM milling machine in the case of prostheses and mill blanks. Optionally, a finishing step can be performed to polish, finish, or apply a coating on the dental material.

The following examples are given to illustrate, but not limit, the scope of this invention. Unless otherwise indicated, all parts and percentages are by weight. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

EXAMPLES

Polymer flexural strength and modulus were calculated using a 3-point flexural test, carried out with a hydraulic universal test system (858 Mini Bionix, MTS Systems Corporation, Eden Prairie, Minn., USA) using a span width of 10 mm and a crosshead speed of 1 mm/min. The flexural strength (FS, $\sigma$) and flexural modulus (modulus, $E_f$) in MegaPascals (MPa) were calculated using the following equations:

$$\sigma = \frac{3Fl}{2bh^2} \qquad \text{(Equation 1)}$$

$$E_f = \frac{F_1 l^3}{4bh^3 d} \qquad \text{(Equation 2)}$$

where F is the peak load (in N), l is the span length (in mm), b is the specimen width (in mm), h is the specimen thickness (in mm); and d is the deflection (in mm) at load $F_1$ (in N) during the straight line portion of the trace (ISO/DIS 4049, 1987). ISO/DIS 4049 is the international standard for "Dentistry—Polymer-based filling, restorative and luting materials". Flexural strength test is one of the tests specified in this standard for the polymer-based filling, restorative and luting materials. Mechanical strength was tested on approximately eight specimens per sample (approximately 25 mm×2 mm×2 mm) and all samples were stored in water for 24 hours prior to flexural strength measurement.

Unless otherwise specified, photopolymerization was carried out using a VIP curing light (BISCO) at 500 mW/cm² for 40×3 seconds irradiation each side.

Near-Infrared spectroscopy (NIR) was performed on a Nicolet Nexus 670 to analyze degree of conversion during or following thermal polymerization.

Proton Nuclear Magnetic Resonance ($^1$H-NMR) was used to integrate, thus quantify, protons of interest in the nanogel polymers (Varian 300 MHz; performed in CDCl$_3$). For example, the CH$_2$ protons in EA, CH$_2$OCH$_2$ protons in TEGDMA, and CH$_3$ protons in dodecanethiol (C$_{12}$SH) at $\delta$ 1.92, 3.75-60, and 0.89 ppm chemical shifts, respectively, were integrated.

Gel permeation chromatography (GPC) using a Viscotek triple array detector system (refractive index, viscosity and light scattering detectors) was used to characterize the nanogels of the present invention in terms of $M_w$, polydispersity, and hydrodynamic radius. This data then verified that the composition did indeed form nanogels.

Atomic force microscopy (AFM) was used to study structural differences between nanogel particles. Topography of certain nanogels was evaluated with an AFM (SPI300; Seiko Instruments Inc., Chiba, Japan) using tapping mode with a spring constant of 15 N/m.

Example 1

Copolymerization of Ethyl Acrylate and TEGDMA

Generally, ethyl acrylate, TEGDMA, C$_{12}$SH, AIBN and toluene (see Table 1) were introduced into a small round bottomed flask. The solution was degassed passing N$_2$ through the solution of a few minutes and then heated at 85° C. for 24 hours. The solvent was removed under vacuum to obtain a viscous colorless material. The product was purified by change of solvent using CH$_2$Cl$_2$ and hexane.

In Table 1, samples MT-44, MT-46, MT-47, MT-57 resulted in undesirable macrogel formation. The other samples were verified to form nanogels based on the GPC results.

TABLE 1

Copolymerization of EA and TEGDMA.

| | EA mol % | TEGDMA mol % | $C_{12}SH$ mol % | AIBN wt % | Toluene wt % |
|---|---|---|---|---|---|
| MT-19 | 98 | 1 | 1 | 1 | 90 |
| MT-20 | 97 | 2 | 1 | 1 | 90 |
| MT-22 | 97.5 | 2 | 0.5 | 1 | 90 |
| MT-23 | 97.9 | 2 | 0.1 | 1 | 90 |
| MT-27 | 98 | 2 | 2 | 1 | 90 |
| MT-33 | 96 | 2 | 2 | 1 | 85 |
| MT-34 | 96 | 2 | 2 | 0.5 | 90 |
| MT-35 | 94 | 2 | 4 | 1 | 90 |
| MT-27# | 96 | 2 | 2 | 1 | 90 |
| MT-38 | 96 | 2 | 2 | 1 | 90 |
| MT-39 | 98 | 2 | 0 | 1 | 90 |
| MT-40 | 96 | 4 | 0 | 1 | 90 |
| MT-43 | 100 | 0 | 0 | 1 | 90 |
| MT-44 | 98 | 2 | 0 | 1 | — |
| MT-45 | 88 | 2 | 10 | 1 | — |
| MT-46 | 83 | 2 | 5 | 1 | — |
| MT-47 | 96 | 2 | 2 | 1 | — |
| MT-56 | 86 | 4 | 10 | 1 | — |
| MT-57 | 84 | 6 | 10 | 1 | — |
| MT-89 | 96 | 2 | 2 | 1 | 90 |
| MT-90 | 83 | 2 | 5 | 1 | 90 |
| MT-91 | 94 | 4 | 2 | 1 | 90 |
| MT-92 | 96 | 2 | 2 | 2 | 90 |
| MT-93 | 96 | 2 | 2 | 1 | 95 |
| MT-94 | 88 | 10 | 2 | 1 | 90 |
| MT-95 | 96 | 2 | 2 | 1 | 90 |
| MT-167 | 96 | 2 | 2 | 1 | 50 |

Example 2

Copolymerization of HEA and TEGDMA

Generally, HEA, TEGDMA, $C_{12}SH$ and AIBN (see Table 2) were dissolved in toluene in a round bottom flask. Toluene was observed to be a poor solvent for HEA. The reaction mixture was purged with nitrogen and then heated at 85° C. For MT-59, -60, -61 and -64, gel formation was observed within a few minutes of heating. For MT-65 and -66, the mixtures were heated for 24 hours.

TABLE 2

Copolymerization of HEA and TEGDMA.

| | HEA mol % | TEGDMA mol % | $C_{12}SH$ mol % | AIBN wt % | Toluene wt % |
|---|---|---|---|---|---|
| MT-59 | 88 | 2 | 10 | 1 | — |
| MT-60 | 88 | 2 | 10 | 1 | 80 |
| MT-61 | 100 | 0 | 0 | 1 | 85 |
| MT-64 | 100 | 0 | 0 | 1 | — |
| MT-65 | 100 | 0 | 0 | 1 | 90 |
| MT-66 | 100 | 0 | 0 | 1 | 95 |

Example 3

Homopolymerization of Hydroxytetrahydrofufuryl(meth)acrylate

Following the same procedures, Hydroxytetrahydrofufuryl(meth)acrylate (HTFMA) was polymerized with AIBN as shown in Table 1. Sample MT-67 did not react and samples MT-79, MT-80, and MT-81, while some polymer product was obtained, resulted in the creation of an insoluble macrogel.

TABLE 3

Homopolymerization of Hydroxytetrahydrofufuryl(meth)acrylate.

| | HTFMA mol % | Crosslinker mol % | $C_{12}SH$ mol % | AIBN wt % | Toluene wt % |
|---|---|---|---|---|---|
| MT-67 | 100 | 0 | 0% | 1 | — |
| MT-79 | 100 | 0 | 0% | 1 | — |
| MT-80 | 100 | 0 | 0% | 1 | 95 |
| MT-81 | 100 | 0 | 0% | 1 | 80 |

Example 4

Copolymerization of HEMA and Tetraethyleneglycoldi(meth)acrylate Using Methylbenzenethiol as Transfer Agent The reagents (see Table 4) were introduced into a small round bottomed flask. The solution was degassed by passing $N_2$ through the solution for a few minutes and then heated at 85° C. for 24 hours. Solution MT-136 was added in alcohol observing precipitation of polymer. The transfer agent in sample MT-136 (*) was methylbenzenethiol rather than C12SH. MT-136 resulted in an insoluble macrogel. The polymer was separated by decantation. MT-138 was precipitated in hexane and found to be soluble in $CH_2Cl_2$.

TABLE 4

Copolymerization of HEMA and TEGDMA.

| | HEMA mol % | TEGDMA mol % | $C_{12}SH$ mol % | AIBN wt % | Solvent wt % | EMA mol % |
|---|---|---|---|---|---|---|
| MT-136 | 95 | — | 5 | 1 | 90 DMSO | — |
| MT-138 | 5 | 2 | 2 | 1 | 90 Toluene | 91 |
| MT-289 | 5 | 2 | 2 | 1 | 90 Toluene | 91 |

Example 5

Copolymerization of EMA and Tetraethyleneglycoldi(meth)acrylate

Generally, ingredients (Table 5) were heated at 85° C. for 24 hours under nitrogen atmosphere. In the procedure, the procedural variables included varying the temperature between 65 to 85° C. and varying the heating time between 20 to 24 hours. The solvent was removed and the product dissolved in $CH_2Cl_2$ and purified by precipitation with hexane. For MT-116, methylbenzenethiol was used as the transfer agent.

TABLE 5

Copolymerization of EMA and TEGDMA.

| | EMA mol % | TEGDMA mol % | $C_{12}SH$ mol % | AIBN wt % | Toluene wt % |
|---|---|---|---|---|---|
| MT-106 | 96 | 2 | 2 | 1 | 90 |
| MT-108 | 94 | 4 | 2 | 1 | 90 |
| MT-109 | 88 | 10 | 2 | 1 | 90 |

TABLE 5-continued

Copolymerization of EMA and TEGDMA.

| | EMA mol % | TEGDMA mol % | $C_{12}SH$ mol % | AIBN wt % | Toluene wt % |
|---|---|---|---|---|---|
| MT-110 | 93q | 2 | 5 | 1 | 90 |
| MT-113 | 83q | 15 | 2 | 1 | 85 |
| MT-114 | 78q | 20 | 2 | 1 | 80 |
| MT-115 | 68q | 30 | 2 | 1 | 70 |
| MT-116 | 68 | 30 | 2 | 1 | 70 |
| MT-138 | EMA/HEMA 91/5 | 2 | 2 | 1 | 90 |
| MT-158 | 96 | 2 | 2 | 1 | 90 |
| MT-159 | 65 | 30 | 5 | 1 | 90 |
| MT-166 | 68 | 30 | 2 | 1 | 90 |
| MT-168 | 60 | 35 | 5 | 1 | 90 |
| MT-169 | 96 | 2 | 2 | 1 | 90 |
| MT-255 | 83 | 15 | 2 | 1 | 85 |
| MT-256 | 84 | 15 | 1 | 1 | 85 |
| MT-257 | 84.4 | 15 | 0.6 | 1 | 85 |
| MT-258 | 84.7 | 15 | 0.3 | 1 | 85 |
| MT-259 | 89 | 10 | 1 | 1 | 90 |
| MT-260 | 94 | 5 | 1 | 1 | 90 |
| MT-262 | 89.5 | 10 | 0.5 | 1 | 90 |
| MT-263 | 94.5 | 5 | 0.5 | 1 | 90 |
| MT-270 | 89.8 | 10 | 0.2 | 1 | 90 |
| MT-271 | 95 | 3 | 2 | 1 | 90 |
| MT-272 | 96 | 3 | 1 | 1 | 90 |
| MT-273 | 94.9 | 5 | 0.1 | 1 | 90 |
| MT-277 | 100 | 0 | — | 1 | 90 |
| MT-278 | 98 | 0 | 2 | 1 | 90 |
| MT-280 | 99 | 0 | 1 | 1 | 90 |
| MT-289 | EMA/HEMA 91/5 | 2 | 2 | 1 | 90 |
| MT-290 | 96 | 2 | $C_2H_4SH$ 2 | 1 | 90 |

Example 6

Copolymerization of EA and Biodegradable Crosslinker

Reagents (Table 6) were dissolved in toluene. A stream of nitrogen was passed through the solution and then heated at 85° C. for 24 hours.

TABLE 6

Copolymerization of EA and Biodegradable Crosslinker

| | EA mol % | Crosslinker MT-37 mol % | $C_{12}SH$ mol % | AIBN wt % | Toluene wt % |
|---|---|---|---|---|---|
| MT-70 | 96 | 2 | 2 | 1 | 90 |
| MT-71 | 93 | 2 | 5 | 1 | 90 |
| MT-73 | 94 | 4 | 2 | 1 | 90 |

An example of a bio-degradable, or simply degradable, crosslinker is MT-37. MT-37 was created by suspending 12.77 g (0.0463 moles) of silver carbonate in a solution of triethylene glycol (0.71 g or 0.043 moles) in dry DMF (10 ml). The cooled (−15 degrees Celsius) suspension was stirred and chloromethylene-oxy-(meth)acrylate (6 g; 0.0337 moles) was added dropwise under argon gas and the exclusion of light. After completion of the addition, stirring was continued for 1 hour. Approximately 20 ml of cold acetone was added and the mixture was allowed to warm to ambient temperature. The reaction mixture was then filtered over a short column packed with silica gel. Ethylacetate was used as the eluent. The volatiles were removed from the filtrate and the residue was taken up in toluene. This organic phase was washed with brine and dried ($Na_2SO_4$). After filtration and concentration, the crude product was obtained that was purified by column chromatography using dichloromethane/ethyl acetate (70-30) as the eluent resulting in 0.5 g of product. The SDMF was distilled over calcium hydride and stored over 3 angstrom molecular sieves two days before used in this experiment.

Figure 4:
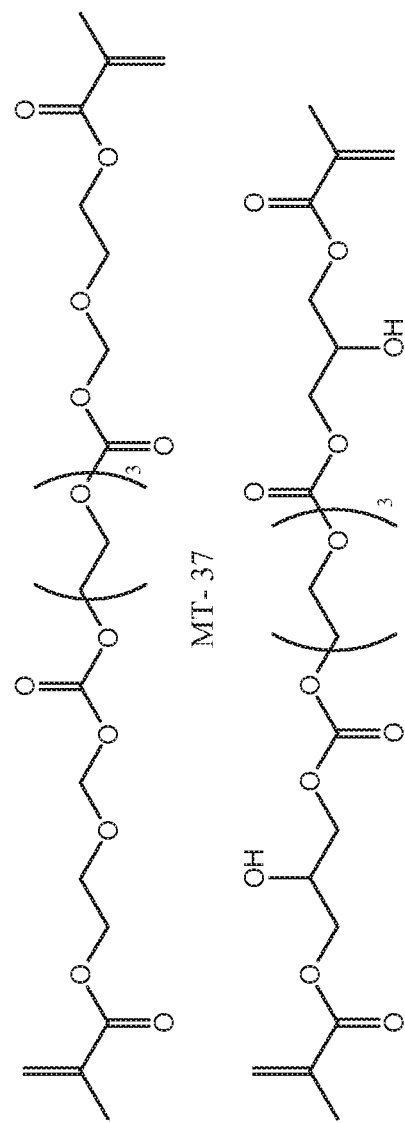
FIG. 4 shows exemplary structures of several degradable chain transfer agents.

MT-37 and other examples of the molecular structure of degradable crosslinkers are provided in FIG. 4.

Example 7

Nanogel Conversion Characterization

Initial studies were directed at identifying synthetic conditions that would provide soluble nanogel particles while defining the influence of various control parameters. Thus, factors such as mono- to di-vinyl monomer ratio, concentration of chain transfer agent and concentration of solvent were evaluated. Other factors including free radical initiator concentration and polymerization reaction temperature were also examined. The thermally initiated polymerization of the mono(meth)acrylate and di(meth)acrylate monomers was monitored by a NIR technique. The reaction mixture consisting of the comonomers, chain transfer agent, thermal initiator and solvent was prepared in a screw-capped vial, which was heated with magnetic stirring. The glass vial could be placed directly into the sample chamber of the NIR instrument and the contents analyzed directly in transmission mode. Disappearance of the (meth)acrylate vinyl (=C—H overtone at 1663 $cm^{-1}$) was followed as the reaction progressed. As shown in FIG. 1, the decrease in the NIR peak area provides a convenient method to monitor polymerization conversion in the dilute toluene solution. After precipitation from hexane, virtually no residual vinyl groups were left in the nanogel. This NIR approach provides a general analytical technique that can be used not only to characterize conversion in the nanogel polymers but also to determine how factors like solvent concentration, initiator concentration and polymerization temperature affect the rate of polymerization, which consequently can alter nanogel polymer morphology. In one case, MT-158, a final conversion of 81.3% (data shown in FIG. 1) was reached.

Example 8

Effect of Monomer Concentration

Figure 2:
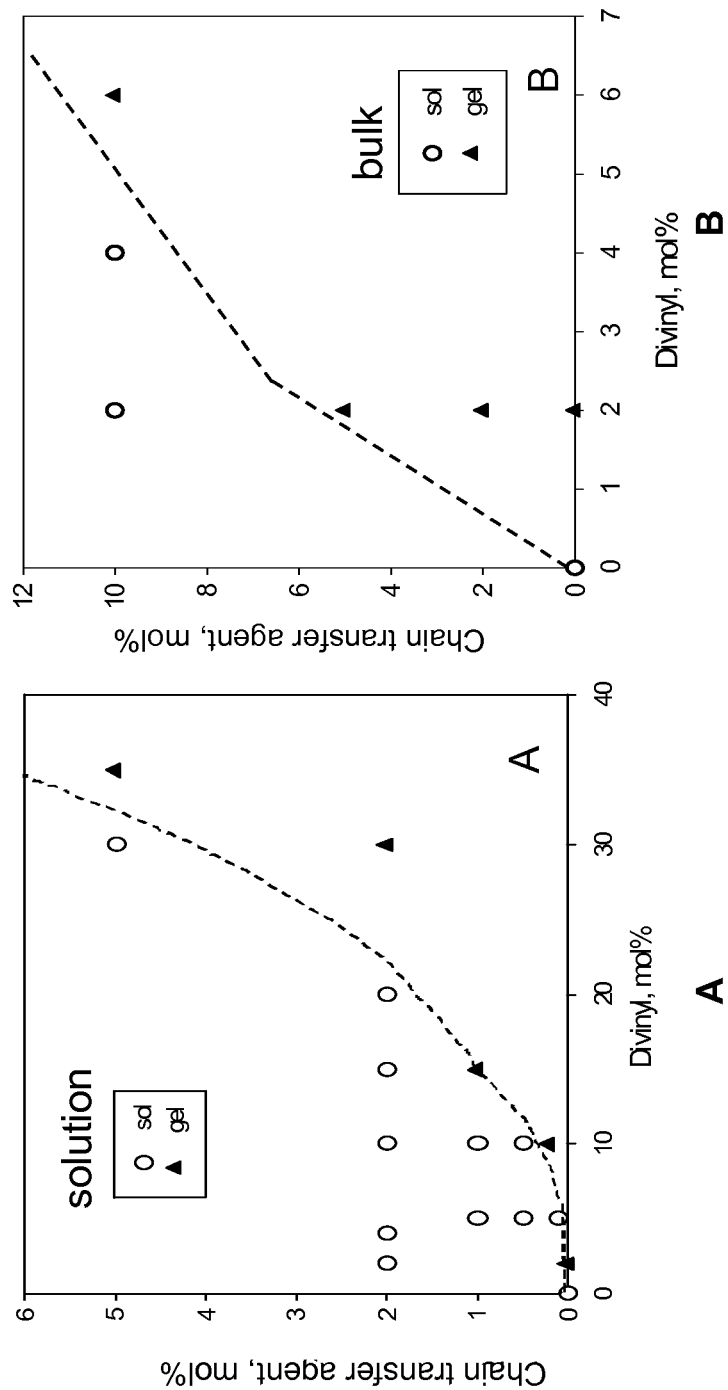
FIGS. 2(A) and 2(B) delineates compositions and synthetic conditions that yield soluble nanogel polymers (sol) or partially macrogelled polymers (gel) for solution (2(A)) and bulk (2(B)) polymerizations.

A range of monovinyl/divinyl/chain transfer agent compositions based on ethyl(meth)acrylate (EMA), tetraethylene glycol di(meth)acrylate (TEGDMA) and dodecanethiol (DD), respectively, were screened to determine what combinations can be expected to provide completely soluble polymers at high degrees of conversion. The standardized polymerization reaction conditions include 1 wt % azobisisobutyronitrile (AIBN) as the thermal initiator, 80% (vol/wt) toluene as solvent and reaction conditions of 65° C. for 6 hours. At the end of this time the sample was visually evaluated to establish whether the polymeric product was completely homogeneous and soluble or whether some gel fraction remained. In cases where some gel was observed, the insoluble polymer component was removed by filtration and dried to quantify the gel fraction obtained. FIG. 2A demonstrates the two-dimensional response surface obtained as the divinyl and chain transfer agent concentrations were varied. Polymers with any perceptible macrogel formation were considered gels regardless of the magnitude of the gel fraction obtained. From the analogous plot in FIG. 2B, it is evident that bulk polymerization conditions require significantly greater chain transfer agent to divinyl ratios to produce completely soluble polymers. However, it is noteworthy that soluble polymers can be obtained at all under these conditions. It is apparent that in addition to the concentration of divinyl monomer and chain transfer agent used, the solvent concentration can be an effective method to provide control over gelation. Significant structural variations in the polymeric nanogels obtained are expected as a result of the specific combination of the synthetic control parameters.

Example 9

Gel Permeation Chromatography Characterization

Unlike macrogelled polymers, the solubility of the nanogels described here allows a variety of characterization tools to be applied to their study. One of the most informative techniques available for the characterization of soluble polymers is gel permeation chromatography (GPC). Nanogel specimens obtained from EMA/TEGDMA copolymerizations with 2 mol % dodecanethiol and 1 wt % AIBN were analyzed in tetrahydrofuran with GPC using a Viscotek triple array detector system (refractive index, viscosity and light scattering). The specimens contained either 4, 10 or 15 mol % TEGDMA in the original comonomer feed. Characterization of the nanogels included the following results:

TABLE 7

GPC characterization of nanogel particles.

| TEGDMA mol % | $M_W$ | Polydispersity | Hydrodynamic radius, nm |
|---|---|---|---|
| 4 (MT-108) | 19,700 | 1.83 | 3.0 |
| 10 (MT-109) | 52,900 | 3.45 | 4.4 |
| 15 (MT-113) | 254,500 | 10.52 | 7.8 |

The data demonstrate the significant structural and dimensional differences that can be obtained as a function of nanogel composition. It is apparent that molecular weight increases rapidly with the divinyl content in the nanogel. Substantial increases in molecular weight and particle size can be expected as the chain transfer agent or solvent concentration is reduced and the discrete nanogel polymers tend toward the macrogel boundary.

Example 10

NMR Characterization

Since the individual nanogel particles proposed here are completely soluble in common organic solvents, in addition to GPC, nuclear magnetic resonance (NMR) spectroscopy can be applied to assist in the characterization of the polymers. As shown in Table 8, excellent agreement has been obtained between the comonomer/chain transfer agent feed composition and the final copolymer composition as determined by integrated solution state $^1$H NMR analyses. These results were obtained on nanogel samples that were purified by precipitation prior to analysis. However, samples can be analyzed at any stage of the polymerization process, with results obtained at low conversion being of particular interest in determinations of kinetic constants, such as experimentally derived rather than estimated values of the chain transfer constant. This demonstrates that a convenient technique exists to verify the incorporation of the various starting material ingredients into the copolymer nanogels. In addition, it has been observed that the individual monovinyl and divinyl monomers can be adequately resolved in the NMR and therefore, comonomer reactivities can be evaluated along with observations of the degree of branching as a function of conversion during nanogel synthesis. In Table 8, the numbers in parentheses represent composition based on integrated NMR data; numbers not in parentheses refer to the actual feed composition of monomers used.

TABLE 8

1H NMR analysis of nanogel composition.

| | Feed composition vs. NMR analysis, mol %* | | | |
|---|---|---|---|---|
| Reactants | MT-89 | MT-90 | MT-91 | MT-94 |
| EA | 98 (97) | 98 (97) | 96 (95) | 90 (88) |
| TEGDMA | 2 (3) | 2 (3) | 4 (5) | 10 (12) |
| $C_{12}SH$ | 2 (1) | 5 (2) | 2 (2) | 2 (3) |

*Copolymerization of ethyl acrylate (EA) and tetraethylene glycol di(meth)acrylate (TetEGDMA) with dodecanethiol ($C_{12}SH$) in toluene at 65° C.

Example 11

Use of Functionalized Nanogels as Dental Fillers

This study evaluated nanogels as prepolymerized organic fillers in an effort to improve mechanical properties and reduce polymerization shrinkage stress in dental restorative materials. The nanogel synthesis was based on the chain-transfer agent controlled copolymerization of mono(meth)acrylate and di(meth)acrylate monomers. The use of HEMA as part of the mono(meth)acrylate component allowed preparation of hydroxy-functionalized nanogel 1, which can be reactivated for subsequent polymerization by reaction with either methacryloyl chloride or isocyanatoethyl(meth)acrylate to yield the reactive nanogels 2 or 3, respectively. The nanogel materials were isolated by precipitation but then remained as discrete polymeric particles that could redissolve in dental monomers to produce transparent resin formulations. Experimental dental resins composed of BisGMA/ TEGMA (7/3 wt) and 10 wt % of nanogel 1, 2 or 3 were prepared. Following visible light polymerization of the experimental materials as well as the unfilled control, modulus and flexural strength (FS) were determined in 3-point bending mode (n=8) and polymerization stress was monitored with a tensometer device.

The results (Table 9) show that nanogel structures can be altered readily to introduce secondary polymerizable groups and these materials can be well characterized. Addition of 10 wt % nanogel does not significantly increase resin viscosity while final polymeric mechanical properties were improved significantly with the polymerizable nanogels (ANOVA; significantly different groups in table). It was also found that the addition of 10 wt % of nanogel reduced polymerization stress by up to 15%, which implicates an active role of the nanogel since modulus was not reduced. Thus, nanogels are highly versatile organic fillers that can be simply applied to increase mechanical properties and reduce polymerization shrinkage stress in dental restorative materials.

As an example, nanogel 1 (Table 9) was prepared by the combination of isobornyl(meth)acrylate (70 mol %), 2-hydroxyethyl(meth)acrylate (10 mol %) and urethane di(meth)acrylate (20 mol %) along with 2-mercaptoethanol (10 mol %) and AIBN initiator (1 wt %) in 2-butanone (80 wt %). The mixture was heated for 4 h at 65° C. The resulting completely soluble nanogel polymer was isolated by precipitation from hexane. Residual traces of solvent were removed under reduced pressure. To convert nanogel 1 to reactive macromonomers (or macromers), the hydroxyl groups were reacted with either methacryloyl chloride and triethylamine or isocyanatoethyl(meth)acrylate and triethylamine in dichloromethane to yield nanogel 2 and 3, respectively.

TABLE 9

Use of Nanogels as Dental Fillers.

|  | Modulus (MPa) | FS (MPa) |
| --- | --- | --- |
| unfilled resin | 2218 ± 91$^a$ | 92.8 ± 5.4$^a$ |
| +nanogel 1 | 2322 ± 55$^a$ | 91.2 ± 1.5$^a$ |
| +nanogel 2 | 2467 ± 81$^b$ | 95.9 ± 3.6$^a$ |
| +nanogel 3 | 2704 ± 131$^c$ | 108.6 ± 3.1$^b$ |

The following Table 10 provides modulus and flexural strength of Bis-GMA/TEGDMA dental resins modified with 10 wt % of nanogel. The nanogel materials were prepared from: isobornyl(meth)acrylate (70 mol %) HEMA (10 mol %) and mercaptoethanol as chain transfer agent. The crosslinker (10 mol %) used in the nanogel synthesis was either urethane di(meth)acrylate (nanogel A), tetraethylene glycol di(meth)acrylate (nanogel B), or Bis-GMA (nanogel C). These three nanogels were then further derivatized (functionalized) by reaction with isocyanatoethyl(meth)acrylate (IEM) to introduce new polymerizable groups on the nanogels (designated with an asterisk "*"). These results demonstrate that the identity of the crosslinker within the nanogels has little impact on properties of the final filled resin polymer, but the presence of polymerizable groups on the nanogel (macromonomer approach) does significantly improve the mechanical properties of the final polymers.

TABLE 10

Comparison of Dental Resins with Nanogel Fillers.

| Samples | Modulus (MPa) | FS (MPa) |
| --- | --- | --- |
| Unfilled control | 2218 ± 91 | 92.8 ± 5.4 |
| Nanogel A | 2460 ± 110 | 94.9 ± 3.0 |
| Nanogel B | 2390 ± 90 | 91.1 ± 4.4 |
| Nanogel C | 2420 ± 130 | 98.0 ± 3.5 |
| Nanogel A* | 2680 ± 120 | 107.7 ± 3.6 |
| Nanogel B* | 2550 ± 100 | 105.6 ± 4.0 |
| Nanogel C* | 2760 ± 110 | 111.5 ± 3.2 |

Example 12

Use of Non-Functionalized Nanogels as Dental Fillers

Figure 3:
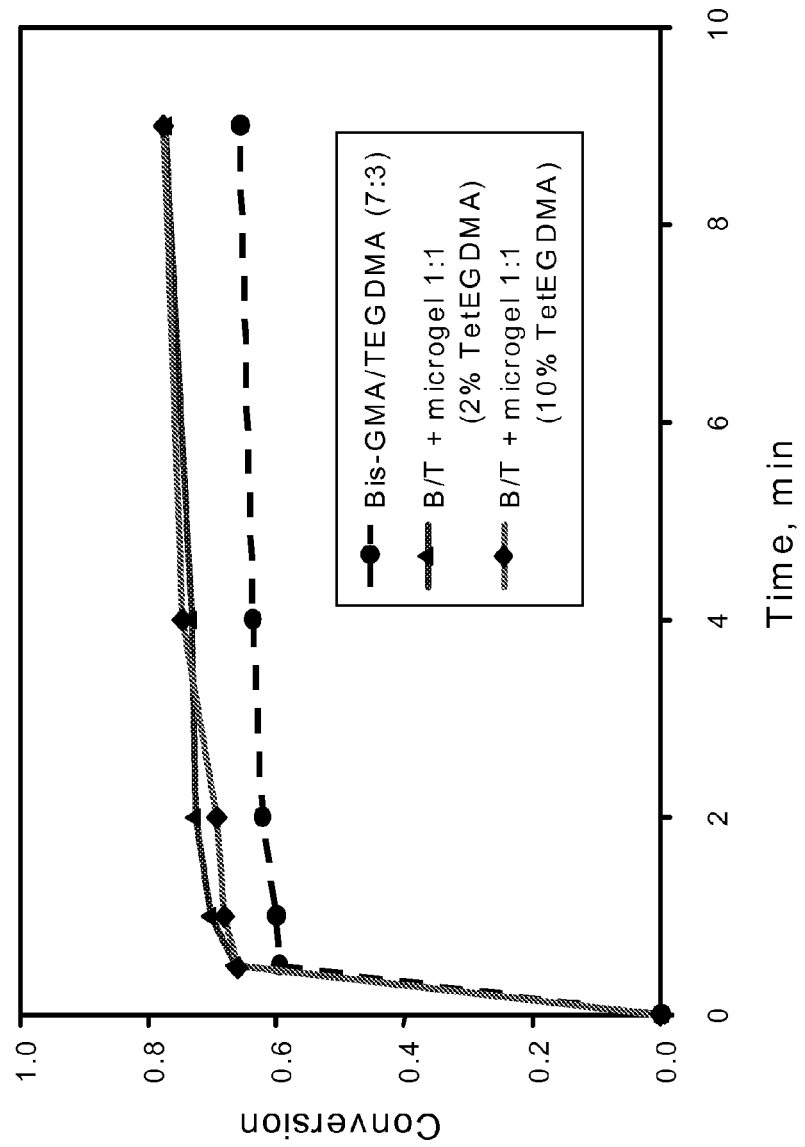
FIG. 3 shows photopolymerization conversion of a Bis-GMA/TEGDMA resin as a function of irradiation time. Solid lines indicate the nanogel-filled materials.

Instead of deploying the functionalized nanogels as reactive macromers, the nonfunctionalized nanogels can be considered as nano-scale inert fillers, which can be added to a variety of monomer systems. These were added in varying proportions (10-50 wt %) to a comonomer mixture composed of Bis-GMA and triethylene glycol di(meth)acrylate. The relatively high proportions of the nanogel materials could be uniformly dissolved in the (meth)acrylate resin without significantly increasing the viscosity. The addition of the nanogel filler should yield substantially reduced polymerization shrinkage through the simple dilution of the reactive group concentration. As shown in FIG. 3, the inclusion of 50 wt % nanogels (at two different branching densities) with the Bis-GMA/TEGDMA resin provided significantly higher (meth) acrylate vinyl conversion that that achieved with the unfilled control monomers. Preliminary evaluation of the mechanical properties of the nano-filled systems shows a modest decrease in fracture strength despite the overall increase in conversion achieved.

The shrinkage data shown in FIG. 3 are based on the Bis-GMA/TEGDMA resin modified with 50 wt % of either MT-106 or MT-109. The mechanical property results shown in Table 9 demonstrate that nanogel-modified dental resins can produced enhanced strength properties.

Example 13

Synthesis of Highly Crosslinked Nanogels

Nanogels with high degrees of branching based on internal crosslinking were prepared from divinyl monomers and chain transfer agent. In these examples, no monovinyl monomer was utilized. The divinyl monomers, either Bis-GMA, urethane di(meth)acrylate (UDMA) or triethylene glycol di(meth)acrylate (TEGDMA), were combined with dodecyl mercaptan (20 mol %) and 1 wt % AIBN as thermal free radical initiator. The polymerization reactions were conducted in dimethylformamide as solvent (80 wt %) at 60° C. In the initial reaction, the time required for macrogelation in each polymerization was noted. For the Bis-GMA, UDMA and TEGDMA reactions, the time to gelation under these conditions was 16, 21 and 35 minutes, respectively. This order of macrogel formation potential is consistent expectations of cyclization reaction potential for the individual monomers. At the first indication of macrogel formation, the soluble portion of the reaction mixture was poured into cold methanol containing 2,6-di-tert-butyl-4-methylphenol as inhibitor to halt further polymerization and to precipitate the nanogel polymer formed. This approach yielded nanogel that could be redissolved in appropriate solvents such as dichloromethane, chloroform or tetrahydrofuran. The point at which macrogelation occurs could be delayed or eliminated entirely by use of larger quantities of solvent in the initial polymerization reaction step. The reactions could also be stopped in advance of the predetermined macrogel point and at this stage, only nanogel and reactants were present in the reaction mixture.

Example 14

Initiation Mode in Nanogel Preparation

Nanogel syntheses involving thermal, photochemical and redox free radical initiation was compared using standardized approaches. The majority of previous work with nanogels has been done with thermal polymerization methods involving peroxide or azo type thermal initiators at reaction temperatures of approximately 60-90° C.

Thermal Initiation.

Figure 6:
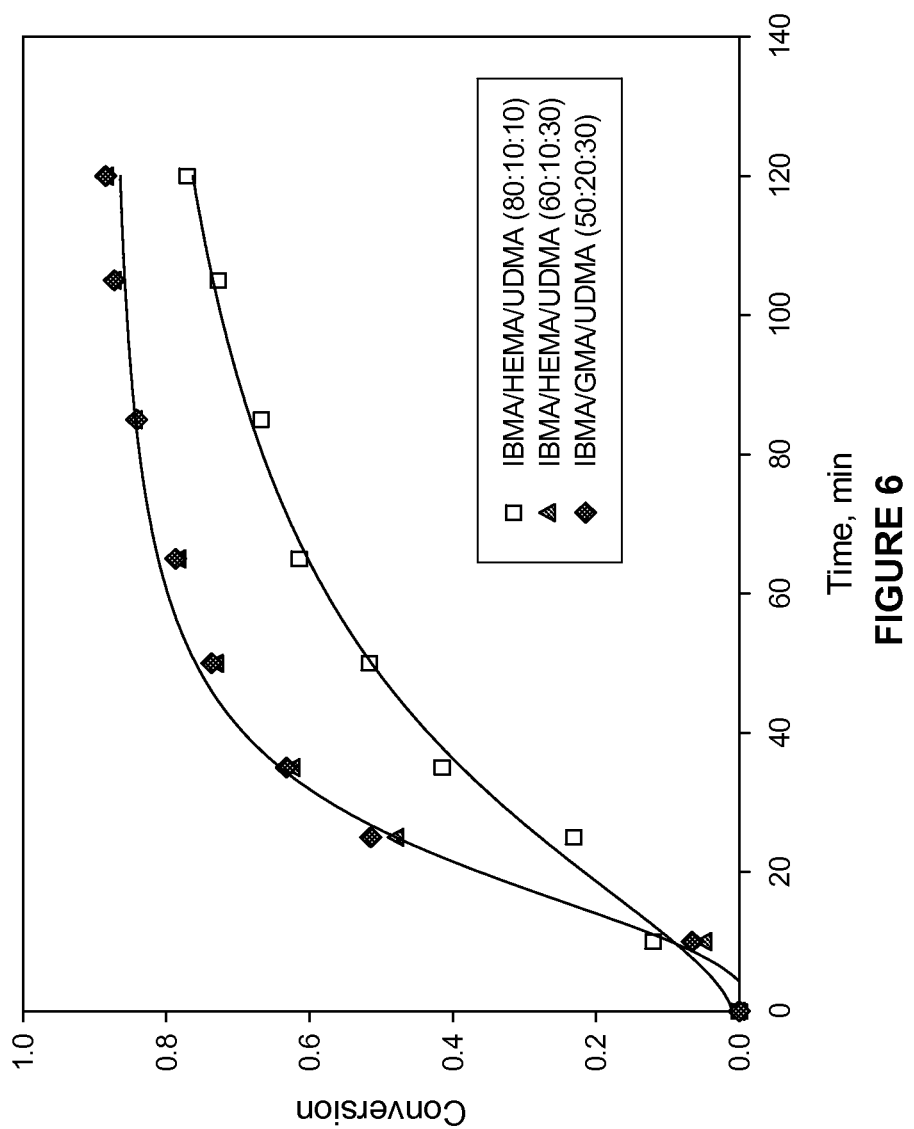
FIG. 6 shows percent conversion vs. time for thermal polymerization of nanogels based on IBMA/HEMA/UDMA with DDT in toluene with 1% AIBN thermal initiator at 70° C.

Thermal polymerization of nanogels formed from various molar ratios of two mono(meth)acrylates (isobornyl(meth)acrylate; IBMA and 2-hydroxyethyl(meth)acrylate; HEMA), and a di(meth)acrylate (urethane di(meth)acrylate; UDMA) with a chain transfer agent in toluene (dodecanethiol; DDT) and 1% AIBN thermal initiator, was performed in 80% methyl ethyl ketone as solvent at 75° C. Molar ratios of IBMA/HEMA/UDMA of 80:10:10; 60:10:30 and 50:20:30 were utilized. The reactions were monitored with near infrared spectroscopy. A graph of the conversion vs. time for polymerization of each nanogel is shown in FIG. 6. The rate of the nanogel formation was shown to be largely dependent on the divinyl content with greater divinyl concentrations resulting in faster polymerization. Under these thermal initiation conditions, the reaction takes at least one to two hours to approach completion, as shown in FIG. 6. An increased efficiency of polymerization was desired.

Redox Polymerization.

Redox polymerization of nanogels was investigated in hopes of increased polymerization efficiency. The monomers used were Bis-GMA as the divinyl and phenoxyethyl(meth) acrylate (POEMA) as the monovinyl. A combination of benzoyl peroxide (1 wt %) and dimethyl-p-toluidine (1.5 wt %) was employed as the redox initiator system. The resulting nanogel would be highly aromatic and of potential use in X-ray scattering studies when polymerized into a lower electron density, aliphatic secondary polymer matrix. The monomers were combined in toluene with the benzoyl peroxide present. The appropriate amount of amine was added and the mixture stirred at room temperature for 4 hours. However, the room temperature reaction progressed very slowly and conversion did not reach substantial levels. By raising the reaction temperature to 40° C., and by adding a second equivalent of the peroxide and amine redox initiators after 30 minutes, the reaction advanced much more efficiently, reaching 63% conversion at 30 minutes and 91% conversion at 50 minutes. Therefore the redox approach is still considered a viable option as an alternative mode of nanogel polymerization, but its practical application appears to require thermal assistance. While the temperature levels are reduced relative to the pure thermal polymerization mode, the full range of temperature options that would extend down to ambient conditions seems unlikely.

Photopolymerization.

Figure 7:
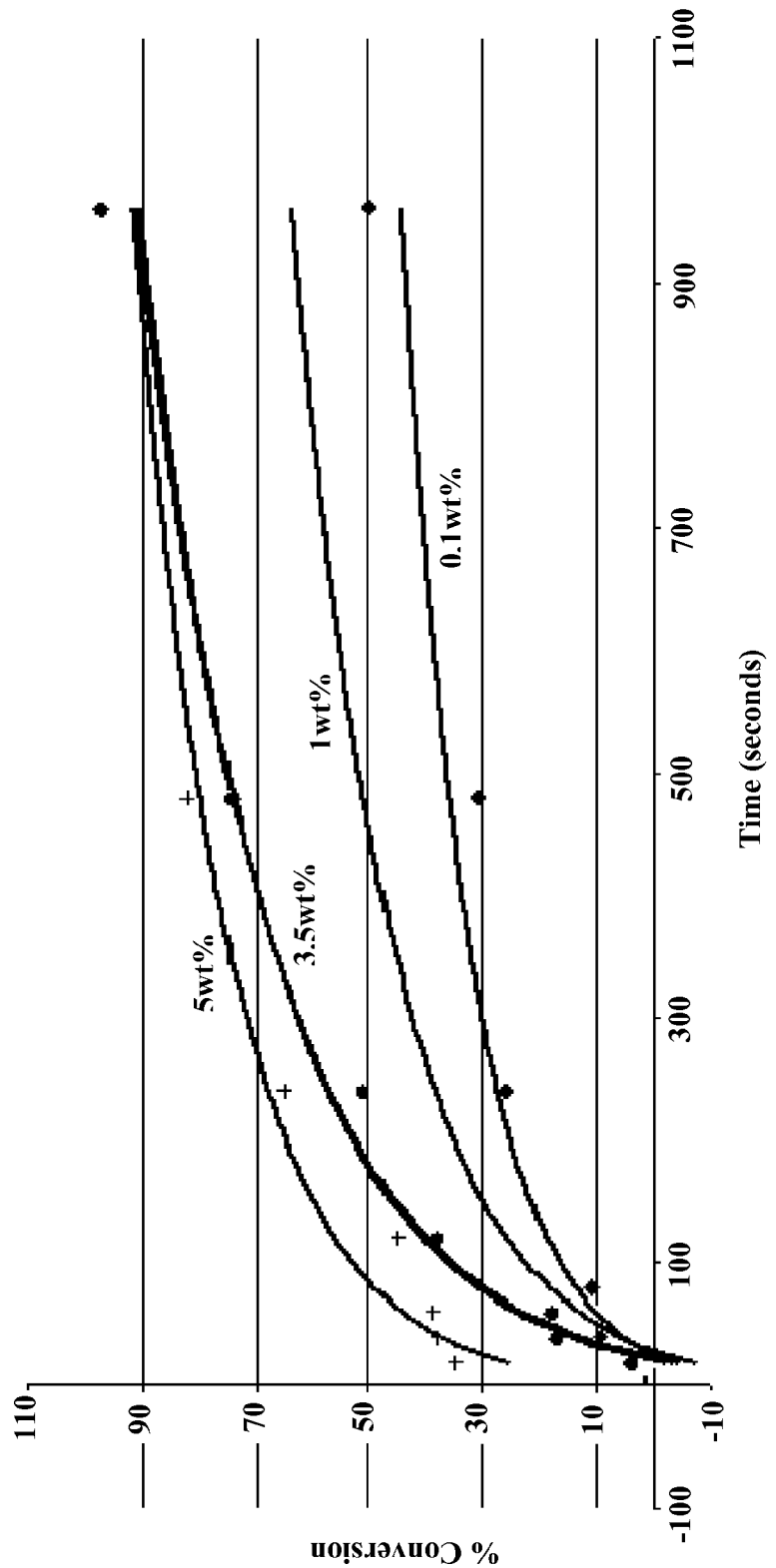
FIG. 7 shows percent conversion vs. time for photopolymerization of nanogels prepared from IBMA/UDMA (7:3 mol ratio) with dodecanethiol (15 mol %) in toluene with 0.1 to 5.0 wt % BAPO photoinitiator at room temperature.

Visible light photopolymerization of nanogels prepared from IBMA/UDMA (70:30 mol %) and dodecanethiol (15 mol %) in toluene (80%) with bisacylphosphine oxide (BAPO; Irgacure 819 from Ciba) as the visible light photoinitiator at concentrations of 0.1 to 5 wt % was performed at room temperature (about 23° C.). Each of the stirred reaction mixtures were irradiated with a dental curing light (SmartLite IQ2 at 700 mW/cm$^2$). Conversion was monitored by mid-IR on aliquots removed at the different exposure intervals. Results are shown in FIG. 7.

The photopolymerization method proved to be by far the most efficient nanogel synthetic method with significantly higher limiting conversion and much shorter reaction times achieved compared with the other techniques. The choice and concentration of the free radical initiator, as well as the irradiance level used in photocuring, provides a wide variety of reaction rates and final conversion values (FIG. 7) during nanogel synthesis. For example, with use of either 3.5 wt % or 5.0 wt % BAPO photoinitiator, the conversion was about 90% at about 15 minutes at room temperature under these conditions. The use of photopolymerization saves considerable time and energy compared with the thermal polymerization process. Photocuring also allows the nanogel polymerization process to be conducted over a wide range of temperatures, including ambient or even sub-ambient temperatures. This is important since if a chain transfer agent is used, such as a thiol, the efficiency of the chain transfer reaction that effectively suppresses macrogelation, increases relative to the chain growth propagation process as the reaction temperature is reduced. Therefore, the option to vary the reaction temperature independent of the reaction rate, provides a useful means of to manipulate the structure and properties of nanogels in a way that can not readily be accomplished with thermal polymerization or thermally-assisted redox polymerization modes.

Comparison of Nanogels Prepared by Thermal Initiation, Photoinitiation and Thermally-Assisted Photinitiation.

A conventional thermal polymerization route to nanogels using azobisisobutyronitrile (AIBN) thermal initiator was compared to the analogous synthesis using photopolymerization at room temperature or at elevated reaction temperatures with BAPO as the photoinitiator. A standardized nanogel composition consisting of isobornyl(meth)acrylate (IBMA) and urethane di(meth)acrylate (UDMA) in 70:30 mole ratio was used with 15 mol % dodecanethiol (DDT) chain transfer agent. For the thermal polymerization, AIBN, which has a one hour half-life temperature of 82° C., was used with a polymerization temperature controlled between 70 to 75° C., which corresponds to half-life times of approximately 2-4 hours, to achieve reasonable reaction rates. The photopolymerization was accomplished with BAPO (Irgacure 819). Photopolymerizations were initially conducted with a 600 mW/cm$^2$ high pressure mercury arc lamp filtered to give 320-500 nm output. All these stirred solution polymerizations were run in 80% toluene. The reaction temperatures were adjusted to either room temperature (23° C.), 45° C., or 70° C. The use of photopolymerization permits ambient temperature polymerization as well as independent control of elevated temperature, which is not the case with thermal polymerizations. The progress of the polymerization was followed in real time by transmission near-infrared spectroscopy based on the disappearance of the vinyl absorption at 6165 cm$^{-1}$. The reaction was continued until the rate of polymerization dropped to near zero based on either consumption of the monomer or the initiator. In initial studies of the photopolymerization reaction at room temperature, irradiation intervals of 7.5, 13.5 and 18.5 minutes were used to get monomer conversion values of 69, 87 and 96%, respectively. The results for the various nanogel formulations are summarized in Table 11. The photopolymerization route to nanogels is both faster and provides much higher conversion than the thermal polymerization technique. The higher limiting conversions possible with photopolymerization, particularly the high conversion achieved with room temperature photocuring, is an unexpected and practically important result. While the use of elevated temperature along with photocuring does allow even more rapid photo-processing, the main advantage of this approach is that it gives a simple method to adjust the relative rates of chain transfer and propagation, which in turn offers an additional parameter in controlling the structure of the nanogel and ultimately, its properties. In several of these batches, the nanogels were isolated by the dropwise addition of the final nanogel solution into a larger volume of hexane, which resulted in precipitation of the polymeric materials. The supernatant solution was decanted and the filtered nanogel dried to give a white powdery polymer. The product yields varied between 38 and 51% with most reactions providing approximately 45% isolated yields of the nanogel.

TABLE 11

Nanogel synthesis by thermal or photopolymerization.

| Condition, initiator | Reaction temperature, ° C. | Reaction time, min | Limiting conversion, % |
| --- | --- | --- | --- |
| Thermal, AIBN | 70 | 180 | 60 ± 12 |
| Photo, BAPO | 23 | 18.5 | 96 ± 2 |
| Photo-thermal, BAPO | 45 | 18.5 | 97 ± 1 |

TABLE 11-continued

Nanogel synthesis by thermal or photopolymerization.

| Condition, initiator | Reaction temperature, °C. | Reaction time, min | Limiting conversion, % |
|---|---|---|---|
| Photo-thermal, BAPO | 70 | 13 | 97 ± 1 |

Nanogel: 70 mol % IBMA, 30 mol % UDMA with 15 mol % DDT in 80% toluene solution.
Reaction conditions: solvent - toluene (80 vol/wt); light - 320-500 nm at 600 mW/cm².

Figure 8:
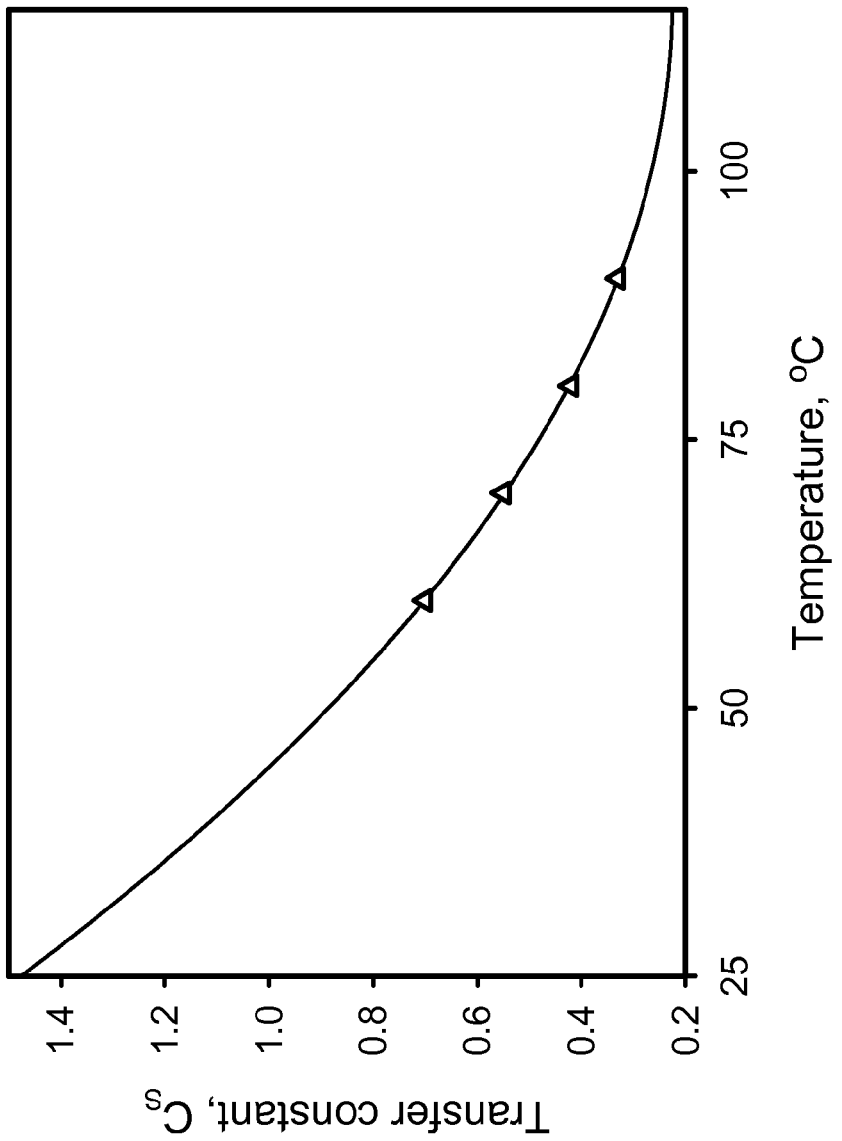
FIG. 8 shows variation of chain transfer constant (Cs) as a function of polymerization temperature for methyl(meth)acrylate with dodecanethiol.

The differences in the nanogels obtained under these conditions have not yet been verified, but data in FIG. 8 shows a chain transfer constant of near unity for dodecanethiol in (meth)acrylate polymerizations at approximately 45° C. FIG. 8 shows variation of chain transfer constant ($C_S$) as a function of polymerization temperature for methyl(meth)acrylate and dodecanthiol, where $C_S = R_{CT}/R_P$ ($R_{CT}$ is the rate of chain transfer and $R_P$ is the rate of polymer propagation). Therefore, in polymerizations at 70° C., the relative concentration of thiol to monomer rises continuously with conversion resulting in progressively shorter polymer chain lengths forming as the nanogel develops. At 45° C., where $C_S=1$, the chain transfer agent and monomer should be consumed at equal rates which means nanogel chain lengths should remain constant throughout the process.

Example 15

Nanogel Surface Modification

Nanogel surface modification can be performed at the end stage of a thermal nanogel synthesis. Nanogel surfaces can be modified by the addition of a different monomer composition at the end stage of a thermal nanogel synthesis. For example, a hydrophobic nanogel, obtained from ethyl(meth)acrylate and ethoxylated bisphenol A di(meth)acrylate, that could not be mixed with water was converted to a readily water dispersible material by adding approximately 10% (based on the initial monomer used) of PEG600 di(meth)acrylate/PEG mono(meth)acrylate and additional chain transfer agent along with an additional quantity of AIBN at the end of the polymerization. While this approach works to modify the nanogel surface, it is not ideal since the simultaneous presence of monomer and initiator in solution can lead to the continued creation of new nanogels based on the late stage monomer composition. The pendant groups on the primary nanogels can capture either monomer or oligomers/polymer/secondary nanogel from solution with the result that the nanogel surface is non-uniform. It is preferable to restrict the active radicals to the nanogel surface such that only monomer, rather than any higher order structures, could be added to the nanogel surface. The use of an iniferter in the initiator system can accomplish this goal.

Example 16

Iniferter-Based Formation of Nanogels

The iniferter, tetraethylthiuram disulfide (TED), when used in combination with 2,2-dimethoxy-2-phenylacetophenone (DMPA) photoinitiator in UV-activated photopolymerization yield what is effectively a "living" nanogel structure that can continue to grow through surface-only radical initiation. A nanogel was formed using isobornyl(meth)acrylate (IBMA)/urethane di(meth)acrylate (UDMA) in 70:30 mole ratio with mercaptoethanol at 15 mol % as the chain transfer agent. The initiator system was 1 wt % DMPA with an equimolar amount of TED. The solution photopolymerization in toluene, irradiated with 2200 mW/cm² light from 320 to 500 nm (mercury arc lamp), was conducted for 140 min to produce a stable conversion of 89%, as measured by real-time near-IR spectroscopy (Table 12). At this point, a second, third and fourth batch of monomer (IBMA/UDMA 70:30) diluted in toluene (2:1 monomer to solvent volume ratio) was added and the irradiation was continued. No thiol chain transfer or additional initiator/iniferter was included with the subsequent monomer batches. With each addition of monomer, the prior stable conversion was restarted. With the fourth batch, the clear solution became cloudy and then opaque; however, there was no indication of macrogelation. It appears that the change in optical properties results from the particle size increasing to the point of interacting with visible light. This is the first example of a nanogel synthesis that produces particles in the 200-500 nm dimension without leading to macrogelation. If the mercaptoethanol is eliminated from the initial batch polymerization, the nanogel formation is less efficient; since irradiation for 255 min to achieve a stable conversion of only 66%. A second batch of monomer was added, again with no thiol or initiator, but there was no continuation of conversion. Therefore, the thiol is important for continued "living" polymerization behavior. The controlled surface-mediated polymerization of nanogels is likely to provide more monodisperse nanogel molecular weight and particle size. This technique thus opens new materials applications.

TABLE 12

Iniferter-based living nanogel synthesis.

| Generation number | Monomer mass, g | Exposure time, min | Limiting conversion, % |
|---|---|---|---|
| 1 | 4.76 | 140 | 89 |
| 2 | 1.32 | 55 | 86 |
| 3 | 2.55 | 100 | 88 |
| 4 | 3.86 | ~15 | * |

*The conversion could not be determined by the near-IR measurement once the solution became opaque.

Example 17

Thiol-Free Nanogel Formation by Photopolymerization

In an unexpected result, it was discovered that nanogels based on an IBMA/UDMA (70:30 mole ratio) composition could be successfully prepared by photopolymerization in toluene (80 v/w %) using BAPO as the photoinitiator (2.5 wt %) without any added chain transfer agent. The result has been replicated several times and soluble nanogels were obtained in 97 to 99% conversion after approximately 30 min irradiation with 320-500 nm light from the mercury arc lamp at 2500 mW/cm².

The ability to make nanogels without any thiol or other chain transfer agent may be specific to this comonomer composition, since several examples of unsuccessful nanogel synthesis attempts were made with other comonomer mixtures, even when thiol chain transfer agent was included. It is a potentially very important finding that will lead to simpler materials with higher molecular weights and particle size compared with the nanogels prepared with chain transfer agent. In additional experiments designed to examine the solvent role in nanogel formation, the same 70:30 mole ratio IBMA/UDMA comonomer composition without thiol was utilized with reduced solvent concentration of either 60 or 70 v/w % toluene. Unlike the soluble, high conversion nanogels obtained with 80 v/w % toluene in the solution polymerization, the reduced solvent concentration lead to undesired macrogel formation within 10 min of the start of irradiation in both cases. Therefore, the 80% solvent concentration with toluene is near the critical limit when no chain transfer agent is present. Lower solvent amounts may be possible with different solvent choices, such as the substitution of acetone or methyl ethyl ketone for toluene. The ability to controllably prepare high conversion, thiol-free nanogels particles is a significant discovery.

Example 18

Characterization of Nanogel Particle Size by Atomic Force Microscopy

One method to visualize and discriminate between the structural differences associated with the different nanogels is atomic force microscopy which can be used to study individual nanogel particles. Nanogel particles of sufficient size such as the "living" nanogel particles formed by the sequential addition of monomer using the iniferter approach, and the nanogels formed in thiol-free systems can be visualized by atomic force microscopy.

Figure 9:
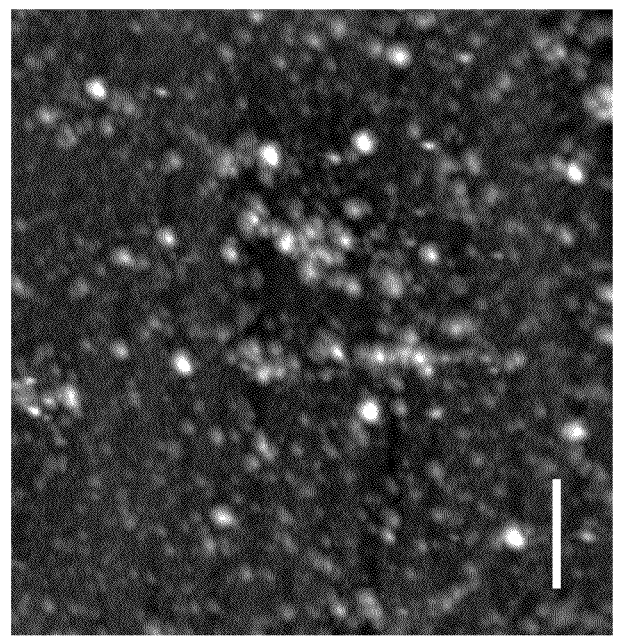
FIG. 9 shows an atomic force microscopy image of nanogel particles made from the solution photopolymerization of IBMA/UDMA (7:3 mol ratio) without chain transfer agent. The scale bar is 500 nm.

Nanogel samples were diluted with toluene to provide a nanogel concentration of 0.05 wt % and sonicated for 5 min for the analysis. The solution was coated on a silicon wafer, the solvent was evaporated, and the topography of the nanogels was evaluated with an AFM (SPI300; Seiko Instruments Inc., Chiba, Japan) using tapping mode with a spring constant of 15 N/m. As example, the AFM image of the nanogel prepared with isobornyl(meth)acrylate (IBMA)/urethane di(meth)acrylate (UDMA; (70:30 mol %) with no chain transfer agent is shown in FIG. 9. The nanogel dimensions are approximately 25-100 nm in the x/y direction and only about 5-10 nm in the z direction. It is assumed that the shape of the nanogel in a dispersed solution of solvent or monomer is essentially spherical with dimensions intermediate between those measured here. It is also expected that the choice of solvent or monomer will affect the degree of swelling but this type of evaluations will need to be conducted with dynamic light scattering in different matrices. The AFM can also be used to provide an estimate of the modulus of the nanogel. The spreading behavior of the particles, based on the difference between the x/y and the z dimensions can also be useful in characterizing structural and property differences among the nanogels.

Example 19

Nanogel Structural Modification by Choice of Comonomer and Chain Transfer Agent

The nanogel structures can be readily modified by selection of the starting comonomers as well as choice of the chain transfer agent. Syntheses were performed where either the mono(meth)acrylate or the thiol chain transfer agent was varied. The nanogels were prepared using the solution photopolymerization technique. To provide nanogels with relatively high modulus, isobornyl(meth)acrylate (IBMA) was copolymerized with urethane di(meth)acrylate (UDMA) in a 70:30 mole ratio. Alternatively, the combination of n-butyl (meth)acrylate (BMA) with UDMA in the same 70:30 mole ratio was used to obtain lower modulus nanogels. Either mercaptoethanol (ME) or dodecanethiol (DDT) were utilized as the chain transfer agent at 15 mol %. The photoinitiator BAPO was used at 5 wt % with a visible light source at 320-500 nm at 2500 mW/cm$^2$. The results of the series of nanogel syntheses are shown in Table 13.

TABLE 13

Compositional variation in nanogels.

| Comonomers (70:30 mole ratio) | Thiol 15 mol % | Nanogel conversion, % | |
|---|---|---|---|
| | | 10 min exposure | 20 min exposure |
| IBMA/UDMA | ME | 82 | 99 |
| | DDT | 95 | — |
| BMA/UDMA | ME | 73 | 96 |
| | DDT | 94 | — |

The various nanogels described above were isolated by precipitation of the clear toluene reaction mixtures from an excess of hexane. The physical appearance of the nanogels differs depending on their specific composition with a more solid powder being formed with the IBMA-based compositions.

Use of ME as the chain transfer agent somewhat reduces the rate of the nanogel photopolymerization process; however, it does not restrict the ultimate conversion possible by slightly extending the irradiation exposure interval. High conversion in the nanogel production process is readily achieved whether the higher modulus IBMA or lower modulus BMA is used. Conversion values are much higher in the solution polymerization process than in bulk polymerization despite the di(meth)acrylate-derived internal branching and crosslinking within the particles. The more rigid IBMA monomer is incorporated slightly more efficiently into the nanogel structure compared with the more flexible BMA monomer.

The choice of DDT or ME as the chain transfer agent alters the nanogel structure. In the case of ME, hydroxyl functionalized chain ends are present to allow reintroduction of polymerizable groups if the nanogel is to be converted to a reactive macromoner. With DDT, a $C_{12}$ aliphatic chain will affect the properties of the nanogel when present in relatively high chain transfer agent concentrations. Nuclear magnetic resonance (NMR) spectroscopy can be used to characterize the composition of nanogels, and measure incorporation of the chain transfer agent to the nanogel. For thermally-initiated polymerization, NMR analyses showed the DDT chain transfer agent was incorporated at levels of approximately 50 to 70% of that used in the feed composition. In nanogels prepared by ambient temperature photopolymerization techniques, the chain transfer agent can be incorporated into the nanogel at higher concentrations relative to an analogous thermal polymerization where the efficiency of chain transfer is reduced compared with propagation.

Example 20

Nanogel as Additives in Secondary Monomers-Photopolymer Mechanical Properties

The nanogels from Example 19 were utilized as inert prepolymeric additives in polymerization with triethylene glycol di(meth)acrylate (TEGDMA) as a secondary monomer. The TEGDMA control sample and the nanogel-modified TEGDMA compositions were photocured with the high pressure mercury arc lamp (Novacure, 320-500 nm at 2500 mW/cm²). The different nanogel compositions exhibited significantly different compatibilities with secondary monomers. The nanogels based on IBMA/UDMA proved to be more compatible and dispersed more readily in TEGDMA. The nanogels prepared with BMA/UDMA could not be dispersed in TEGDMA unless they were made with ME as the chain transfer agent. With DDT as the thiol and BMA as the mono(meth)acrylate, there is a very high content of non-polar, alkyl chains that do not permit even a homogeneous 10 wt % nanogel mixture in TEGDMA. In contrast, with ME as the thiol, nanogels with either IBMA or BMA could be dispersed uniformly in TEGDMA to at least 40 wt %. While the control photopolymerization gave TEGDMA conversion of approximately 84%, the addition of 10 wt % nanogel, regardless of the nanogel composition, gave significantly increased levels of conversion, which reached 96-99%. The mechanical properties of the nanogel-modified TEGDMA photopolymer were evaluated (Table 14).

TABLE 14

Mechanical properties of nanogel/TEGDMA photopolymers.

| Nanogel composition | Nanogel content, wt % | Flexural strength, MPa (std dev) | Flexural modulus, GPa (std dev) |
|---|---|---|---|
| None (TEGDMA control) | 0 | 105.3 (10.6) | 1.84 (0.23) |
| IBMA/UDMA/DDT | 10 | 95.9 (8.6) | 1.66 (0.13) |
| " | 20 | 64.9 (10.8) | 1.24 (0.21) |
| IBMA/UDMA/ME | 10 | 90.4 (8.5) | 1.60 (0.25) |
| " | 20 | 84.7 (13.4) | 1.72 (0.20) |
| " | 30 | 47.8 (18.7) | 1.89 (0.31) |
| " | 40 | 47.5 (20.9) | 1.95 (0.28) |
| BMA/UDMA/ME | 10 | 81.8 (5.2) | 1.43 (0.12) |
| " | 20 | 74.5 (10.0) | 1.36 (0.09) |
| " | 30 | 32.9 (7.1) | 1.30 (0.12) |
| " | 40 | 27.7 (7.5) | 1.78 (0.32) |

These are non-reactive nanogels which are incorporated into the TEGDMA network strictly through physical chain entanglements. The mechanical property data demonstrate that while the flexural strength drops as the nanogel concentration is increased as expected, the modulus remains essentially unaffected, particularly for the more rigid IBMA nanogel as the additive. The benefit to adding significant amounts of nano-scale prepolymerized material to a monomer is that the final clear polymer obtained will have proportionally reduced levels of shrinkage and stress. It was unexpectedly discovered that the addition of nanogels promoted the significant increase to near quantitative conversion. It is also evident that nanogels can be useful to alter a variety of properties in the secondary polymer such as refractive index and radioopacity (if a appropriate monomers containing bromine, iodine or metal salts are used in the nanogel synthesis).

Figure 10:
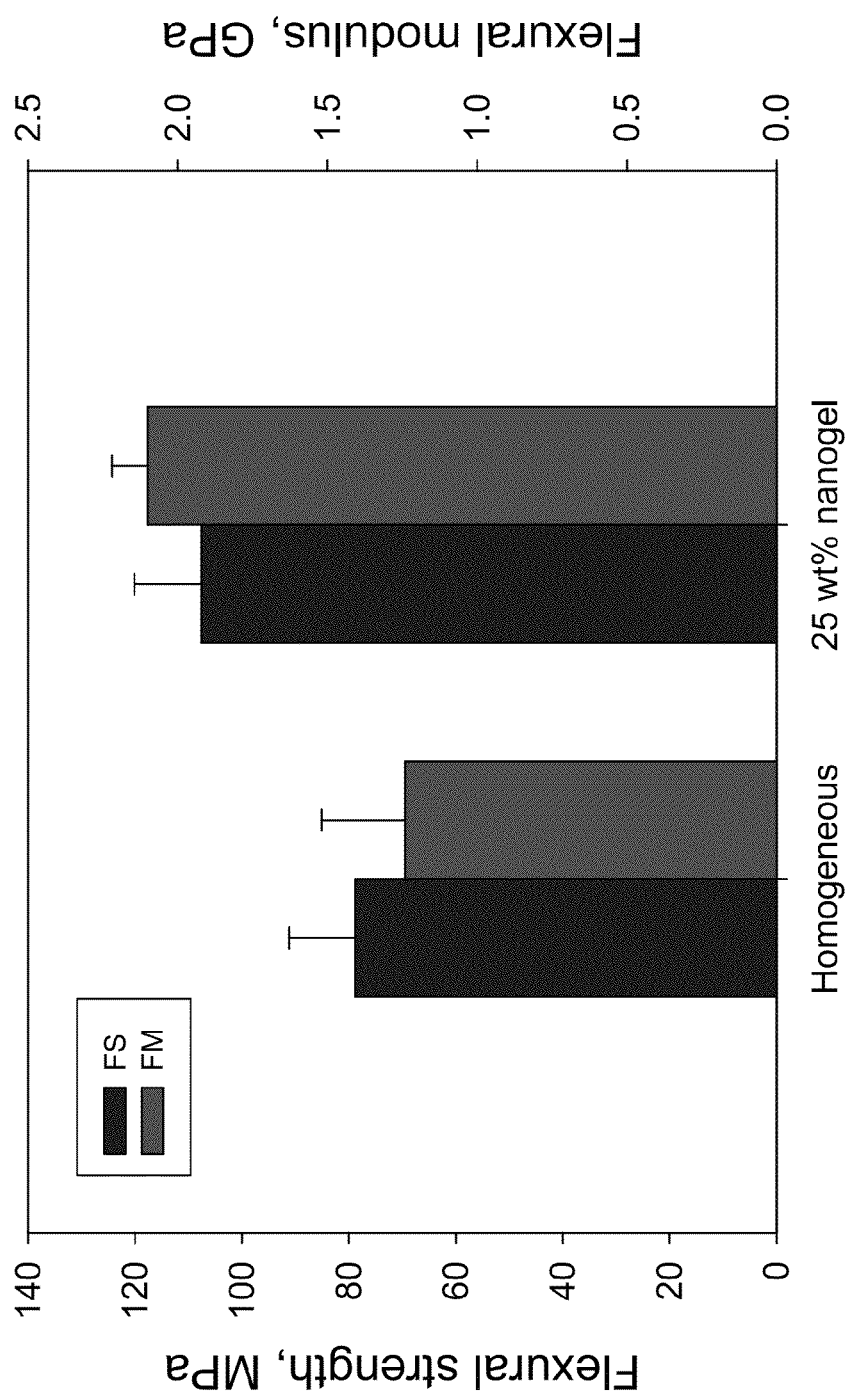
FIG. 10 shows three-point bending strength properties of flexural strength (MPa) and flexural modulus (GPa) of TEGMA with and without 25 wt % nanogel POEMA/Bis-GMA (85:15 mol ratio).

An aromatic nanogel was prepared by photopolymerization of phenoxyethyl(meth)acrylate (POEMA) and Bis-GMA (85:15 molar ratio) as an alternative to nanogels based on aliphatic comonomers. In this case, the addition of 25 wt % of the aromatic nanogel to TEGDMA resulted in an increase in both flexural strength and modulus compared with the unmodified TEGDMA homopolymers as shown in FIG. 10.

Example 21

Effect of Nanogels on Optical Properties of Secondary Monomers

Figure 11:
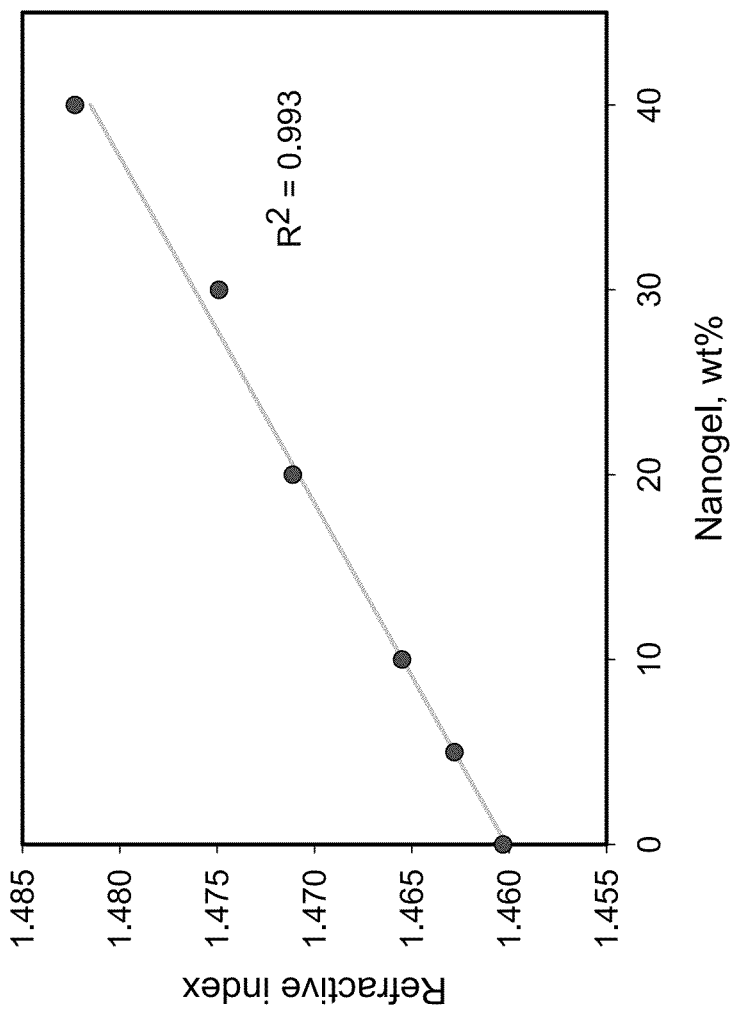
FIG. 11 shows refractive index at 21.8° C. of TEGMA with various wt % nanogel-modified TEGMA solutions. The nanogel was composed of IBMA/UDMA (7:3 mole ratio) and dodecanethiol.

The addition of nanogel can also be used to alter the refractive index of the secondary monomer as well as its polymer. A nanogel was prepared from IBMA/UDMA comonomers in a 70:30 mole ratio with dodecanethiol. It was added in varying amounts to triethylene glycol di(meth)acrylate (TEGDMA) with a significant effect on the measured refractive index as shown in FIG. 11. FIG. 11 shows room temperature refractive index measured by refractometer for TEGDMA and the series of nanogel-modified TEGDMA solutions. During the nanogel polymerization, the refractive index rises significantly and so the optical effect on the secondary monomer is magnified compared with the monomeric state of the nanogel components. By extrapolation of the plot in FIG. 11, we can estimate the refractive index of the pure nanogel to be approximately 1.51.

This approach can be exploited to tune the refractive index of a monomer to that of a filler used in a composite application. This ability to match the refractive indices of the resin and filler without having to reformulate the basic resin composition provides a means to optimize the optical clarity of the composite which could be of benefit during photopolymerization of thick specimens as well as simply to obtain a specific degree of transparency or translucency.

Nanogels were prepared from phenoxyethyl(meth)acrylate (POEMA) and Bis-GMA where both these aromatic monomers contribute relatively high refractive index values. The combination of PEOMA and Bis-GMA comonomers (70:30) has a refractive index of 1.521 whereas the analogous value for the mixture of IBMA/UDMA is only 1.481.

Comonomers can be selected so as to lower refractive index dramatically, for example, by selecting fluorinated monomers, RI~1.34. Alternatively, comonomers can be selected so as to raise refractive index, for example, by selecting monomers with napthyl or tribromophenyl types of substituents; RI>1.6.

The choice of the thiol chain transfer agent also has a significant effect on the nanogel optical properties since dodecanethiol (DDT) has a refractive index of 1.459 while mercaptoethanol (ME) has a value of 1.500. Therefore, for the same amount of nanogel additive in TEGDMA, the POEMA/Bis-GMA/nanogel would provide a much greater positive effect on refractive index compared with the IBMA/UDMA nanogel example.

The effect of nanogel content on the optical clarity of the nanogel-modified secondary monomer was evaluated. In Table 5, the transmitted near-IR signal intensity was used as a probe of optical density of TEGDMA monomer containing various proportions of the IBMA/UDMA nanogel in either its inert or reactive form. From this, the reactive nanogel appears to induce a slightly greater optical effect; however, in either case, the reduction in NIR transmissivity with nanogel content decreases at the higher loading levels.

TABLE 15

Changes in Translucency for the Nanogel-modified TEGMA monomer/polymer as compared to unloaded TEGMA.

| Amount of added nanogel | Reduction in translucency, %* | |
|---|---|---|
| (wt %) | Non-reactive | Reactive |
| 5 | 5.3 | 7.0 |
| 10 | 12.5 | 10.9 |
| 20 | 14.7 | 18.8 |
| 30 | 15.8 | 22.7 |
| 40 | 22.6 | 24.9 |

Example 22

Polymer-Induced Phase Separation of Nanogels

Polymerization-induced phase separation (PIPS) involves use of marginally compatible comonomers that produce heterogeneous copolymers. In one aspect, certain nanogels can be dispersed into monomers to yield phase separation at the interface between the nanogel and the matrix polymer during the secondary polymerization process. Phase separated polymer structures can be utilized to increase toughness as well as reduce shrinkage and stress compared with their homogeneous polymer counterparts. Marginally compatible monomers are used for nanogel synthesis in this aspect. For example, Bis-GMA/lauryl(meth)acrylate (LMA) and Bis-GMA/isostearyl(meth)acrylate (ISMA) can be used as marginally compatible comonomers for nanogel synthesis. Bis-GMA is a widely used aromatic di(meth)acrylate monomer that has strong hydrogen bond donor/acceptor behavior. In contrast, lauryl(meth)acrylate (LMA) and isostearyl(meth)acrylate (ISMA) are mono(meth)acrylates with extended aliphatic structures that give amorphous polymers with no hydrogen bond donor potential. The very different molecular structures lead to phase separation between the Bis-GMA/LMA and Bis-GMA/ISMA comonomer pairs for certain compositions at room temperature.

Since the nanogel synthesis is conducted in solution, the solvent used can act as a compatibilizer such that any comonomer composition can be considered for nanogel synthesis. The chain transfer agent, e.g. dodecanethiol (DDT), can also serve as a compatibilizer for these monomer pairs. As either the LMA or ISMA content is increased in the nanogel, the potential compatibility of the nanogel with conventional monomers decreases along with the modulus, glass transition temperature and hydrophilicity. The goal is to be able to modify the degree of secondary monomer infusion into the nanogel and create the possibility of interfacial phase separation during polymerization of the matrix monomer around the nanogel particles. The nanogel composition and its degree of compatibility with the surrounding monomer are expected to provide significant control over the heterogeneous polymer structure and properties.

The nanogels useful for PIPS were prepared by photopolymerization in either 80 v/w % toluene or acetone, where the comonomers were 20% by mass compared with the solvent volume. The molar ratios of the comonomers were 10:90, 20:80 or 50:50 for the divinyl (Bis-GMA) to monovinyl (LMA or ISMA). In addition, 15 mol % (based on monomer) of dodecanethiol was used as a chain transfer agent to limit macrogelation. A visible light photoinitiator (BAPO, Irgacure 819) was used at 5 wt % along with exposure to a 2500 mW/cm$^2$ high pressure mercury arc lamp filtered to give 320-500 nm output. The reaction mixture was vigorously stirred at room temperature during irradiation. The progress of the polymerization was followed in real time by transmission near-infrared spectroscopy based on the disappearance of the vinyl absorption at 6165 cm$^{-1}$. The reaction was continued until the rate of polymerization dropped to near zero based on either consumption of the monomer or the initiator. The results for the various nanogel formulations are summarized in Table 16.

TABLE 16

Nanogels with limited compatibility in conventional monomers.

| Monomers | Ratio (mol %) | Polymerization in toluene | | Polymerization in acetone | |
|---|---|---|---|---|---|
| | | Rxn time, min | Conversion, % | Rxn time, min | Conversion, % |
| Bis-GMA/LMA | 10:90 | 24 | 90 | 29 | 70 |
| " | 20:80 | gelled | — | 24 | 70 |
| " | 50:50 | gelled | — | 29 | 70 |
| Bis-GMA/ISMA | 10:90 | 24 | 91 | 30 | 74 |
| " | 20:80 | gelled | — | 24 | 71 |
| " | 50:50 | gelled | — | 29 | 76 |

With toluene as the solvent, only the lowest divinyl content compositions gave successful dispersed nanogel particles. At 20 or 50 mol % Bis-GMA in toluene, the entire reaction mixture gelled at relatively low polymer conversion. In contrast, the use of acetone as solvent allowed the highly branched nanogels to form up to a limiting conversion of approximately 70%. This level of conversion is lower than that obtained with toluene as the solvent. It is notable that the 50:50 divinyl/monovinyl compositions both produced some localized polymer gel on the side of the reaction flask adjacent to the light source, but this did not extend to any gel formation in solution. A lower light intensity with even more vigorous stirring may avoid the localized gelation in these cases. The 50 mol % divinyl contents in these examples are at the very high end of degree of nanogel branching that have been observed in these studies and are significantly higher than those typically encountered in the literature.

Triethylene glycol di(meth)acrylate (TEGDMA) was investigated as the matrix monomer for these nanogels. The TEGDMA containing 10 wt % of the Bis-GMA/ISMA 20:80 nanogel formed an opaque polymer upon photopolymerization due to polymerization-induced phase separation (PIPS). The 10:90 materials with Bis-GMA/LMA and Bis-GMA/ISMA did not form homogeneous mixtures, where the 20:80 materials did give uniform monomer/nanogel solutions. The choice of the secondary monomer is critical as is the reaction kinetics involved with the secondary polymerization process in controlling PIPS with nanogels. There would be practical utility in the use of nanogel-modified comonomer systems where one of the monomers is relatively incompatible with the nanogel additive while the other monomer serves as a compatibilizer. The benefit is that the overall degree of compatibility of the whole system can then be effectively controlled by variation in the comonomer composition.

Example 23

Nanogel Effects on Filled and Unfilled Composites

Inert (non-reactive) and reactive nanogels were prepared and analyzed for effects on viscosity and polymerization shrinkage, as well as effect on loading of inorganic filler to composites. Inert nanogels were prepared from photopolymerization of IBMA/UDMA with mercaptoethanol as chain transfer agent. The same batch of nanogel was converted to reactive macromer by dispersing the nanogel into dichloromethane and adding isocyanatoethyl(meth)acrylate (IEM) in excess to form covalent urethane linkages between the hydroxyl groups on the nanogel, from the mercaptoethanol chain transfer agent, and the polymerizable (meth)acrylate groups, from the IEM. The reactive nanogel was isolated as previously mentioned by precipitation from hexane, filtration and evaporation of any residual solvent. The macromer version of the nanogel was able to be dispersed into solvent or monomer.

Figure 12:
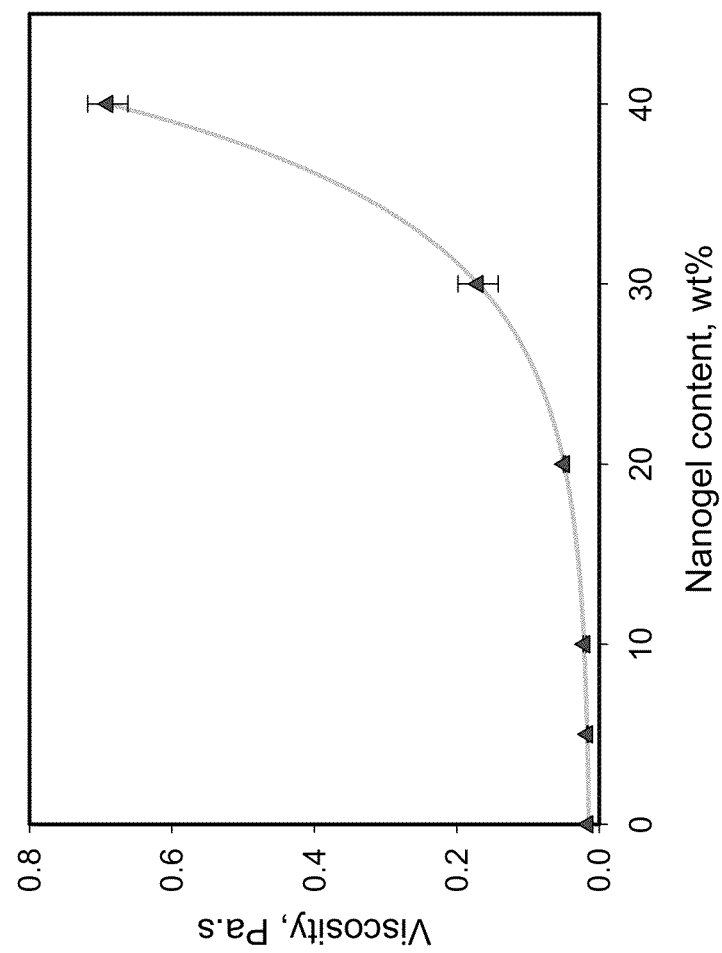
FIG. 12 shows viscosity measurement of various inert nanogel loading levels in TEGMA monomer.

To find the viscosity limits of nanogel wt % addition to the TEGDMA monomer, the room temperature viscosity of the TEGDMA control and a series of nanogel-modified solutions in TEGDMA with up to 40 wt % inert nanogel additive was determined. The results, shown in FIG. 12, indicate that at low to moderate nanogel contents, the effect on viscosity is minimal with this particular combination of nanogel and monomer. As the nanogel loading level is increased, at some point, the particle-particle interactions begin to dominate the particle-liquid interactions and the viscosity rises dramatically. In this particular combination of nanogel and monomer, the viscosity begins to rise rapidly with nanogel content at approximately the 25 wt % level. The viscosity behavior is expected to vary with the size and structure of the nanogel as well the compatibility between the nanogel and the monomer, which will alter the degree of nanogel swelling and affect the volume fraction of the liquid.

Figure 13:
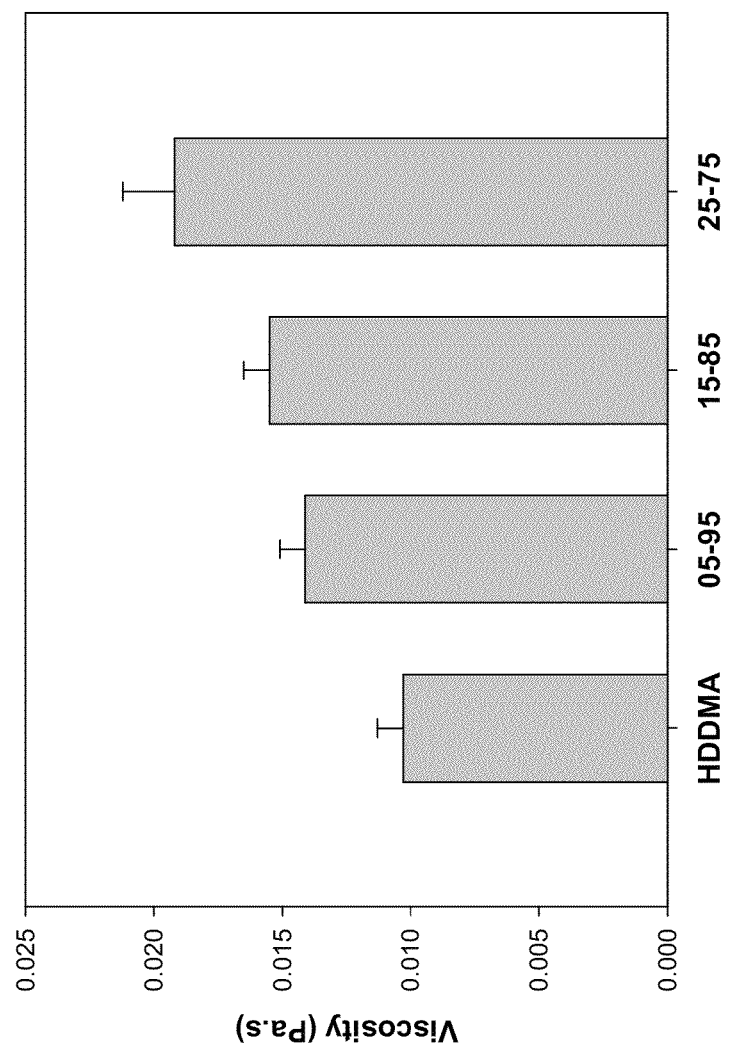
FIG. 13 shows effect of nanogel structure on 1,6-hexanediol di(meth)acrylate (HDDMA) viscosity with and without 10 wt % nanogel content. The nanogels were prepared from POEMA/Bis-GMA at various molar ratios as shown.

Different combinations of nanogel and monomer will produce different viscosity effects due to the nanogel additive. For example, 1,6-hexanediol di(meth)acrylate (HDDMA) was used as the secondary monomer with a fixed amount (10 wt %) of Bis-GMA/POEMA nanogel while varying the composition and structure of the nanogel at 5:95, 15:85 and 25:75 molar ratios. As the proportion of divinyl monomer used in the nanogel synthesis was increased, the effect of the nanogel additive on monomer viscosity also increased as shown in FIG. 13.

Figure 14A:
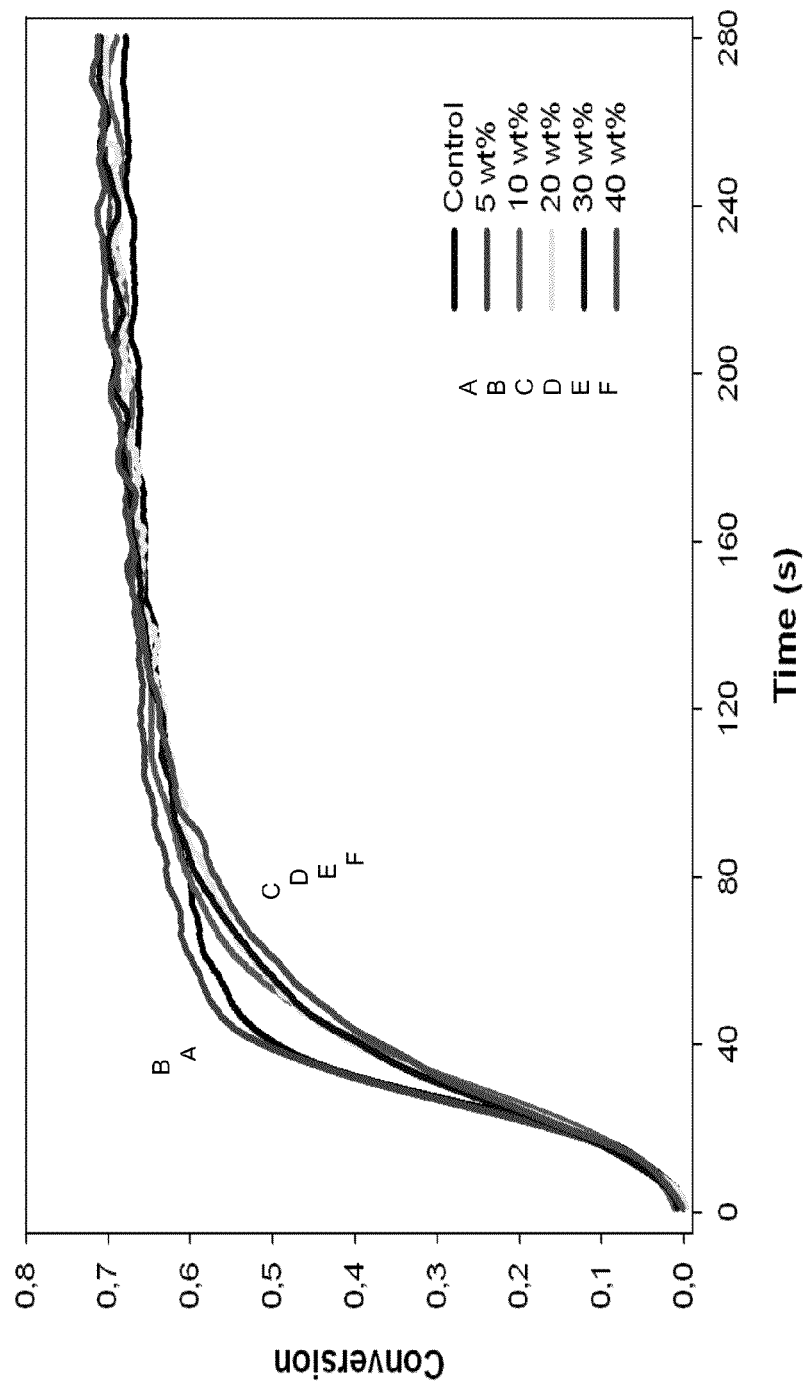
FIG. 14A shows conversion vs. time of photopolymerization of TEGMA monomer with varied levels of IBMA/UDMA nanogel additive. The graph shows the effect of a non-reactive inert nanogel.
Figure 14B:
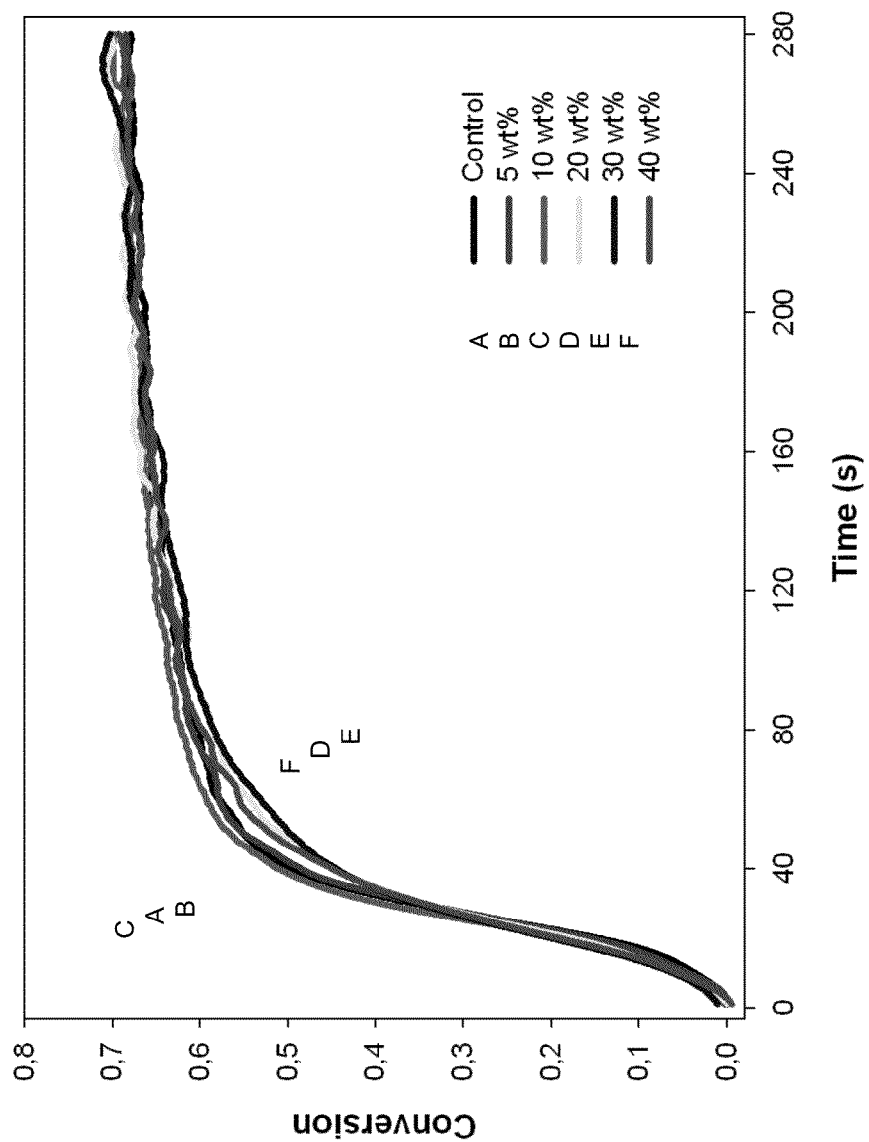
FIG. 14 B shows conversion vs. time of photopolymerization of TEGMA monomer with varied levels of IBMA/UDMA nanogel additive. The graph shows a reactive nanogel in which the mercaptoethanol chain transfer reagent of the polymer has been reacted with isocyanatoethyl(meth)acrylate.

The effect of nanogel content on the photopolymerization kinetics of TEGDMA was then evaluated. A nanogel loading range of 0 to 40 wt % was utilized with both the inert and reactive nanogel compositions prepared above in this example. The standardized visible light initiated photopolymerization of the TEGDMA was monitored by real-time near-IR spectroscopy at room temperature. The kinetic plots shown in FIG. 14 (A) indicate a slight reduction in reaction rate with the higher nanogel loadings for the inert, non-reactive nanogels as additives. The final conversion appears to be only marginally affected by the nanogel addition, in spite of the increased viscosities. The kinetic plots shown in FIG. 14 (B), show the affect of reactive nanogel content on the rate of polymerization is even less and the differences in final conversion are negligible (within the measurement error). Final conversion relative to the unmodified control monomer is dependent on the specific nanogel-monomer combinations evaluated, with either higher, modestly lower or unchanged final conversion relative to the unmodified control monomer exhibited when consistent photocuring conditions are used. In those cases where the nanogel additive results in a reduction in conversion of the secondary monomer, an extension of the irradiation time or an increase in the irradiance used in the photopolymerization process is sufficient to at least match the conversion value achieved with the control monomer.

Figure 15:
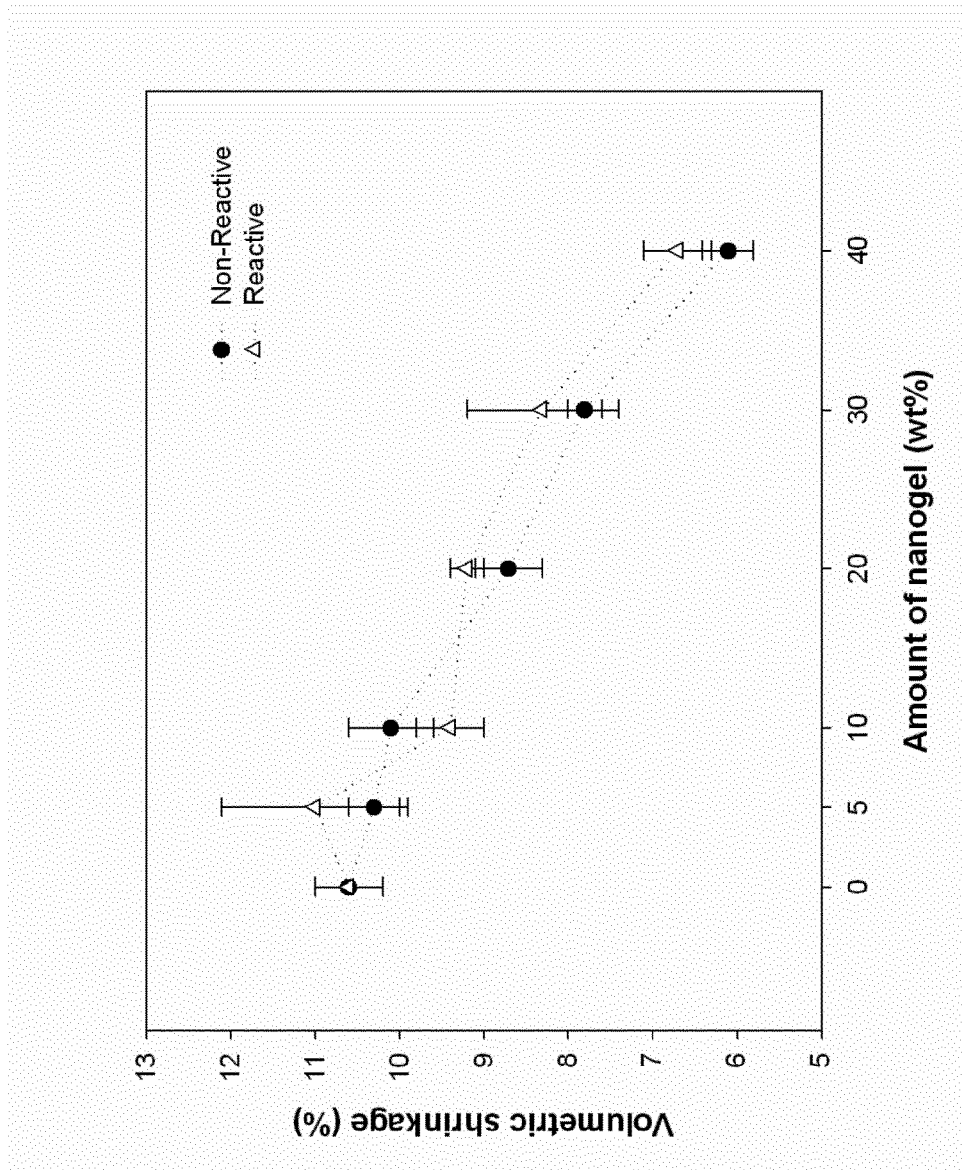
FIG. 15 shows volumetric polymerization shrinkage vs. the nanogel content in unfilled TEGMA.

One of the primary objectives for the use of nanogels to modify secondary monomers is to provide a means to reduce the polymerization shrinkage of that secondary monomer. FIG. 15 shows the relationship between polymerization shrinkage and the inert or reactive nanogel content in unfilled TEGDMA. The inert and reactive nanogels were prepared as in Example 23, paragraph 1. The linear correlation coefficients for the non-reactive and reactive nanogel modified TEGDMA shrinkage data are $R^2$=0.976 and 0.921, respectively. In principle, the reduction in shrinkage should scale with the volume fraction of the prepolymerized additive. This relationship could be altered by the extent of monomer diffusion into the nanogel, the differential in moduli between the separate domains as well as the type of interface between the nanogel and the surrounding polymer matrix. Since the polymerized nanogels are higher in density than the TEGDMA monomer, the volume fraction of added nanogel would be expected to be less than its corresponding weight fraction. However, the experimentally observed reduction in photopolymerization shrinkage, as measured by ACTA linometer, as a function of the weight percent of nanogel additive (FIG. 15) demonstrates a linear decrease in shrinkage that correlates well with the weight fraction of the nanogel.

Nanogel-Modified Composites with Filler

In many polymer applications, the use of filler is required to achieve adequate physical and mechanical properties. One example of this is a dental composite restorative where the use of silanized inorganic particulate filler is required for control of material properties such as hardness, modulus, ultimate strength, thermal expansion and wear as well as providing the optical translucency that mimics nature tooth. The addition of filler is also critical in reducing the exotherm associated with polymerization of the matrix resin and limiting the extent of polymerization shrinkage. Therefore, it is important that any proposed modification of the resin phase, such as the introduction of nanogels, does not interfere with the ability to load filler into the resin. It is also important for any resin additive to have minimal influence on the polymerization kinetics of the resin and composite materials.

Polymerization Shrinkage and Conversion of Nanogel-Modified Composites with Filler.

Use of nanogel modifiers for the resin phase of particulate-filled composites involved the introduction of inert and reactive IBMA/UDMA-based nanogels into TEGDMA. Inert and reactive nanogels are prepared as in Example 23, paragraph 1. For the 70 wt % barium glass-filled composite in TEGDMA containing 40 wt % IBMA/UDMA nanogel, the measured reduction in shrinkage is approximately half that of 70%-filled TEGDMA control without the nanogel additive; data=5.62±0.21 vol % shrinkage for the TEGDMA control composite versus 2.55±0.28 vol % shrinkage for the dual-filled TEGDMA composite with both glass and nanogel. Essentially equivalent conversion values obtained for both composite materials means the differences in shrinkage are based on physical not chemical differences. The reduction in polymerization shrinkage is expected to translate into concomitant reduced levels of stress development as has previously been demonstrated.

Filler Loading with Nanogel-Modified Composites.

Figure 16:
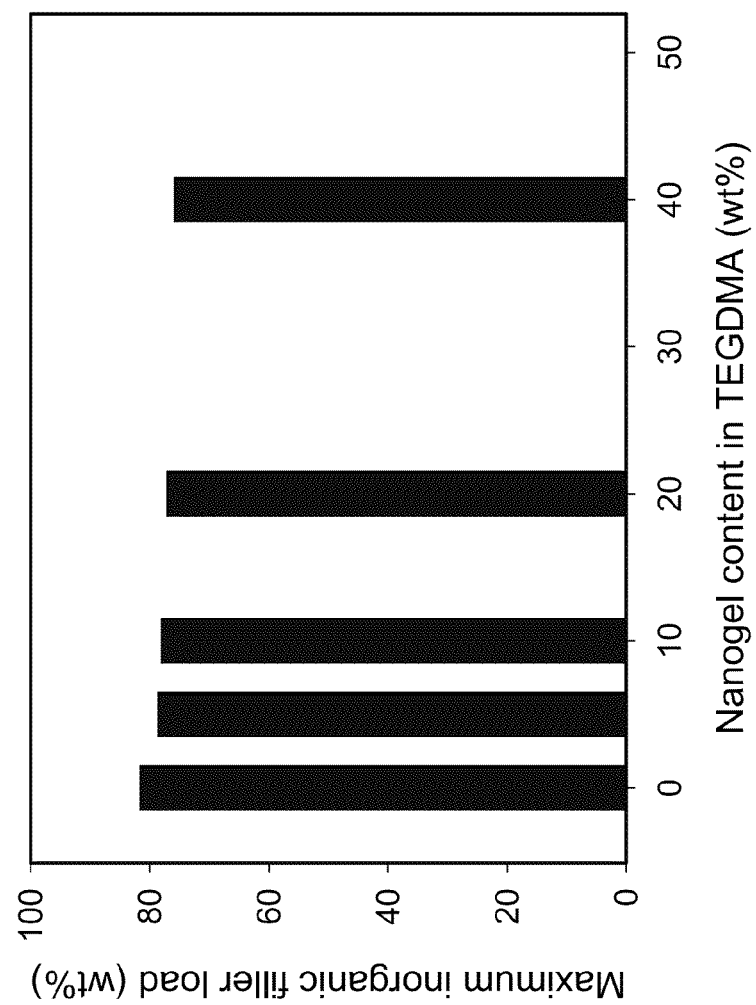
FIG. 16 shows maximum inorganic filler loading limits in TEGMA with 0, 5, 10, 20 and 40 wt % added nanogel (IBMA/UDMA 70:30 mol ratio with mercaptoethanol 15 mol %). The filler was silanized barium glass filler (0.4 μm).

The introduction of nanogel should not significantly reduce the potential to load inorganic particulate filler in composite applications. FIG. 16 shows maximum inorganic filler loading limits in TEGDMA with 0, 5, 10, 20, 40 wt % added nanogel (IBMA/UDMA 70:30 with mercaptoethanol 15 mol %. The silanized barium glass filler (0.4 μm) was added using a centrifugal mixer to reach the maximum attainable filler load. The use of up to 40 wt % nanogel still allowed 75-80 wt % of the barium glass filler (>60 vol %) to be added to the TEGDMA monomer regardless of nanogel loading level (FIG. 16). Therefore, even at high nanogel loading levels where there are significant direct nanogel particle-particle interactions, the ability to incorporate inorganic filler is not significantly compromised.

Comparison of nanogel-modified glass-filled composite was made to nanogel-modified composite without filler using 70 wt % uniform high level of barium glass filler (0.4 μm average). Various amounts of nanogel from photopolymerization of IBMA/UDMA (70:30 mole ratio) with mercaptoethanol (15 mol %) were utilized. Modulus was determined in three-point bending mode on 2×2×25 mm bars. Conversion was measured on the same bar specimens by near-infrared spectroscopy. Data is shown for conversion and modulus in Table 17.

The data in Table 17 reinforce previous results showing no reduction in conversion of the secondary monomer as a consequence of the nanogel presence at any level. This applies to both the nanogel-only and the dual nanogel/glass additives. For the nanogel-modified composite without filler, the flexural modulus remains essentially unchanged regardless of the amount of the unreactive nanogel used. In the barium glass-filled nanogel-modified composites, the modulus is significantly raised by the inorganic filler as would be expected in typical particulate-filled composites. Table 18 shows a similar comparison of the effect of nanogel additives, both inert and reactive, on the mechanical properties of experimental TEGDMA photopolymers, flexural strength drops with increasing inert nanogel content while the reactive macromer nanogel induces no decline in strength with increasing amounts of additive. The flexural modulus remains essentially constant regardless of the nanogel content or its reactive state.

TABLE 17

Comparison of nanogel effect on TEGDMA resin and composite modulus.

| Nanogel, | TEGDMA + Nanogel | | TEGDMA + Nanogel + Glass | |
|---|---|---|---|---|
| wt % | Conv, % | Modulus, GPa | Conv, % | Modulus, GPa |
| 0 | — | 1.84 | 80 | 6.55 |
| 5 | 77 | 1.36 | 86 | 5.30 |
| 10 | 85 | 1.60 | 86 | 6.77 |
| 20 | 83 | 1.56 | 84 | 6.12 |
| 40 | 86 | 1.59 | 82 | 5.72 |

TABLE 18

Mechanical properties of inert and reactive nanogel-modifed TEGDMA photopolymers.

| Nanogel, | Flexural strength, MPa | | Flexural modulus, GPa | |
|---|---|---|---|---|
| wt % | Non-reactive | Reactive | Non-reactive | Reactive |
| 5 | 118.4 (7.6) | 105.3 (10.8) | 2.01 (0.13) | 1.78 (0.18) |
| 10 | 116.5 (6.4) | 102.2 (9.7) | 1.94 (0.15) | 1.77 (0.12) |
| 20 | 81.0 (12.3) | 103.2 (9.2) | 2.03 (0.16) | 1.93 (0.12) |
| 30 | 60.6 (5.9) | 100.1 (5.0) | 2.26 (0.13) | 1.97 (0.06) |
| 40 | 36.4 (10.6) | 102.1 (3.5) | 1.96 (0.36) | 1.96 (0.09) |
| 0 | 108.9 (14.9) | | 1.94 (0.23) | |

Example 24

Preparation of Fluorescent Nanogels

Nanogels were prepared utilizing a fluorescent monomer. The initial nanogel synthesis utilized the IBMA/UDMA comonomer combination (70:30 mole ratio) in toluene (80%) but without addition of any chain transfer agent. The nanogels were prepared by photopolymerization using 2.5 wt % of BAPO as visible light initiator and the 320-500 nm output of a mercury arc lamp. While the control composition was successfully prepared as a soluble, high conversion nanogel, the addition of 0.4 wt % (relative to the monomer content) of methacryloxyethyl thiocarbamoyl rhodamine B resulted in macrogelation during the polymerization process.

The fluorescent nanogel was successfully obtained when the procedure was repeated but with the addition of 5 mol % mercaptoethanol as a chain transfer agent. The high conversion isolated powdery nanogel readily disperses into appropriate solvents to give a transparent but highly colored solution. Fluorescent nanogels of this type could be used to image the spatial distribution of these nanoparticles. For example, by attachment of cell binding proteins to the nanogel surface, the presence of the fluorescent probe would allow optical visualization of the localized interactions of the nanogels to cell surfaces or even the uptake of the nanoparticles into cells. The nanogels can carry small molecules (drugs, cell signaling factors, etc.) in covalently tethered or encapsulated modes. The nanogel itself and/or any tethers used can be made degradable. For the imaging of targeted delivery, the use of a fluorescent probe within the nanogel structure or potentially just on the nanogel surface, could be an important and useful experimental tool.

Example 25

Nanogel Additives to Dental Adhesives

An important aspect of successful function of a dental composite, cemented crown or inlay is the adhesive used to bond the dental material to the tooth. Particularly in cases of dentin bonding, the choice of the bonding resin is critical. A large portion of the adhesives used in the placement of dental composite restoratives rely on relatively hydrophilic monomers dissolved in a volatile solvent such as acetone or ethanol. The hydrophilicity is necessary so the monomers can effectively penetrate into the acid-demineralized collagen network of etched dentin. A common example of a bonding resin composition consists of Bis-GMA, which provides moderate hydrophilic character but also mechanical strength and crosslinking, while 2-hydroxyethyl(meth)acrylate (HEMA) is included to provide substantial hydrophilicity to the overall resin. The HEMA as well as the water compatible solvent, carry the Bis-GMA into the collagen network. The majority of the solvent is then removed assisted by a gentle stream of air to thin the adhesive layer and accelerate evaporation. The single or multiple coatings of the adhesive are then typically photopolymerized prior to placement of the dental composite. The oxygen inhibited (meth)acrylate groups that remain unreacted after photocuring the adhesive, can then interact with the (meth)acrylate monomers introduced by the composite. When the composite is subsequently photopolymerized, the adhesive layer, which is predominantly physically interlocked with the dentin, copolymerizes with the composite resin to provide a strong attachment between the composite restorative and the tooth. However, due to its hydrophilic nature, the adhesive picks up significant amounts of water. This significantly weakens the polymer and reduces the bond strength. The adhesive layers often fail with water channels opening along this interfacial zone. As a means to overcome the degree of water uptake in the bonding resin and more importantly, to improve the long term integrity and strength of dental adhesives, we have proposed the use of nanogel additives that are hydrophobic, high modulus and reactive. Since the nanogel particle size is well below that of the dimensions of the interconnected collagen pore structure, the expectation is that nanogels can infiltrate the dentin along with the solvent and comonomers. When copolymerized with the conventional hydrophilic adhesive monomers, the nanogels can reduce the potential for water uptake and reinforce the polymer mechanical strength of the network especially in terms of the wet strength.

Preliminary results with adhesive materials were obtained using nanogels prepared from either IBMA/UDMA (70:30 mol ratio) or IBMA/EBPDMA (70:30 mol ratio) each with 15 mol % mercaptoethanol as the chain transfer agent. As previously mentioned, the hydroxyl groups associated with the mercaptoethanol were used to reintroduce polymerizable groups through addition of isocyanatoethyl(meth)acrylate to form the urethane linkage. Bis-GMA/HEMA (60:40) was selected as a representative dental adhesive resin. Since these adhesives are applied to dentin in a solvated form, such as 40-70% ethanol, but then the majority of solvent is removed by evaporation prior to polymerization, 10 wt % ethanol was included in the adhesive resin as a means to simulate a practical clinical system in this study. This control composition was compared with the nanogel-modified versions where 25 wt % of the reactive nanogel macromer was added (based on mass of the Bis-GMA/HEMA comonomers). The introduction of the nanogel raised the viscosity of the partially solvated (10 wt % ethanol) adhesive resin from 0.12±0.01 Pa·s to 1.94±0.04 Pa·s. In this case, the order of magnitude increase in viscosity is not a concern since in practical use, the adhesive resin would contain at least 40-70 wt % ethanol as a diluent.

Figure 17:
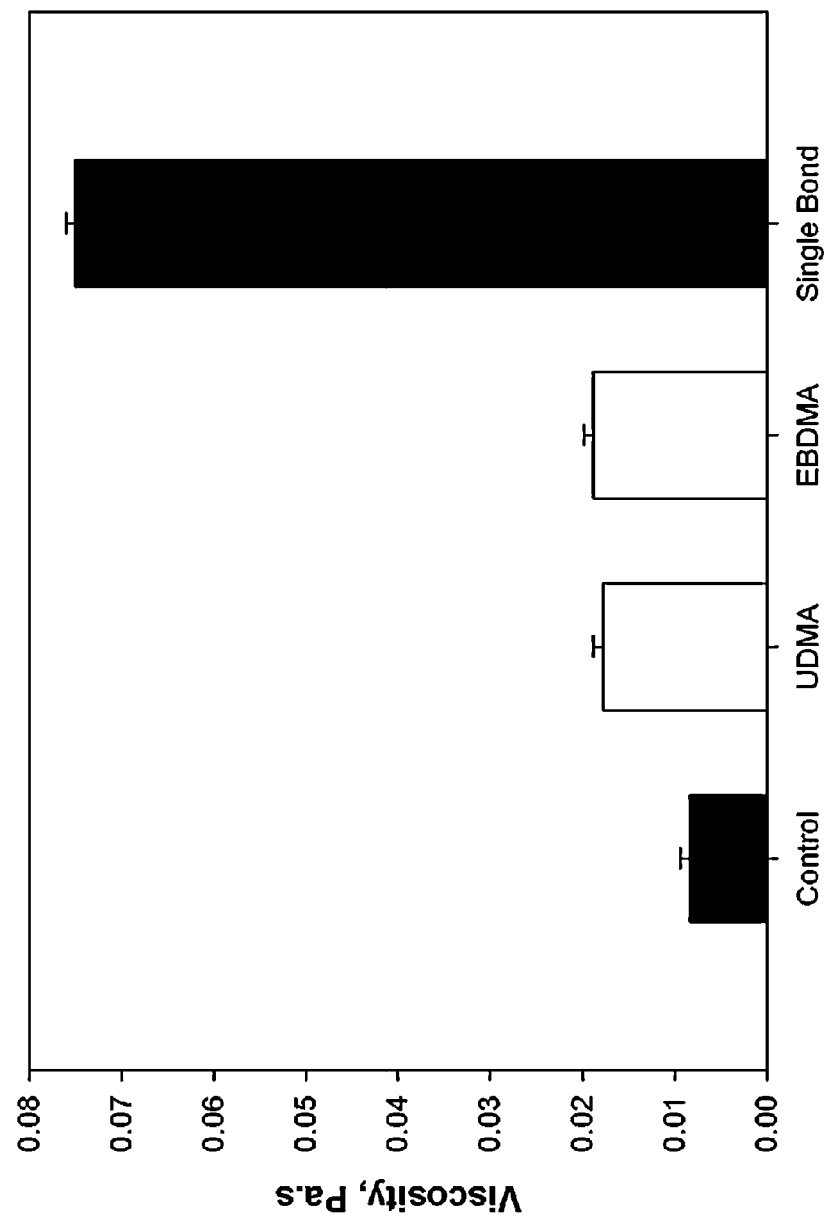
FIG. 17 shows room temperature viscosities of BisGMA/HEMA control, BisGMA/HEMA with 25 wt % nanogel prepared from IBMA/UDMA, BisGMA/HEMA with 25 wt % nanogel prepared from IBMA/EBPDMA, and commercially available bonding resin Single Bond (3M/ESPE). Each of the control, UDMA and EBDMA test samples was diluted in 50 wt % ethanol to mimic solvated bonding agents.

As a demonstration, the viscosities of the control resin Bis-GMA/HEMA and the nanogel-modified Bis-GMA/HEMA experimental materials with 25 wt % added nanogel, prepared from either IBMA/UDMA or IBMA/EBPMA, with 50 wt % added ethanol are shown in FIG. 17. In this solvated state, the nanogel additives contribute equivalent viscosity increases relative to the control but the difference is only a factor of two. For comparison, a commercial bonding resin, Single Bond (3M/ESPE), is shown to have a much higher viscosity than the experimental nanogel-modified solvated adhesives. This indicates that even greater amounts of nanogel could be incorporated into the adhesive if desired.

Figure 18:
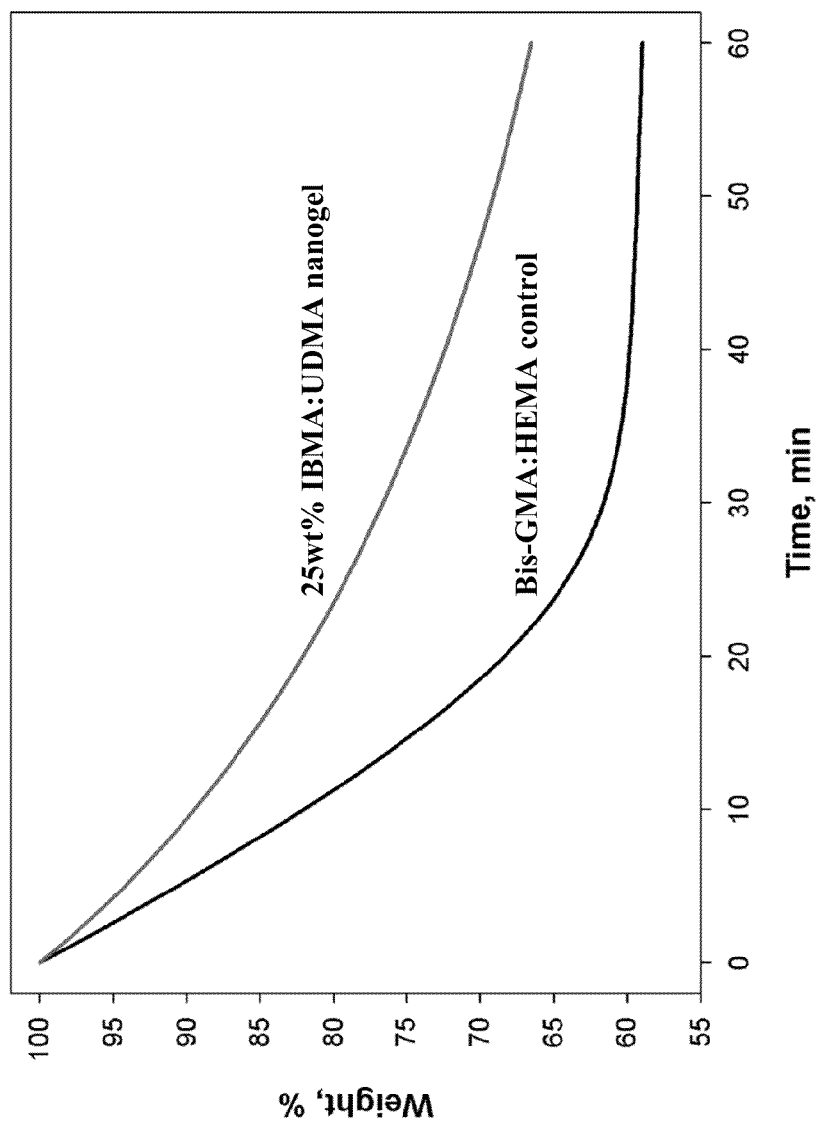
FIG. 18 shows mass change vs. time for room temperature evaporation rate of ethanol from the BisGMA/HEMA control resin and the control with 25 wt % of the IBMA/UDMA nanogel.

The presence of high molecular weight, highly crosslinked nanogel particles in the solvated resin could potentially restrict solvent evaporation. To test this, thin film samples of the monomeric control and the 25 wt % nanogel-modified resin, both solvated with 50 wt % of ethanol, were placed into a thermogravimetric analyzer (TGA) under a continuous airflow at room temperature. From the TGA mass loss data (FIG. 18), it is apparent that solvent evaporation from the control sample is more rapid and more complete than that achieved with the nanogel additive under these conditions (approximately 80% of solvent removed from the control versus 65% for the experimental material). This indicates that a more aggressive air thinning procedure, retesting at elevated temperature or use of a more volatile solvent, such as acetone, may be required for clinical use of nanogel-modified adhesives.

Comparison of the adhesive control with the nanogel-modified analogs based on IBMA/UDMA and IBMA/EBPDMA, in visible light-initiated photopolymerization showed conversion was 77.8, 78.5 and 81.5%, respectively, which represents no significant differences in final conversion. Real-time monitoring of conversion by near-infrared spectroscopy during the photopolymerization process also demonstrated negligible differences in reaction kinetics associated with the inclusion of the nanogel additives. The IBMA/UDMA nanogel-modified sample provided a slightly translucent polymerized material. The water solubility of the polymer specimens for this material was reduced by 23% relative to the control polymer. This reduction in the release of unreacted monomer would potentially benefit biocompatibility and stability of the dental adhesive. Importantly, the water sorption was also reduced by 18% through the use of the moderately hydrophobic nanogel particles into the adhesive resin.

Figure 19:
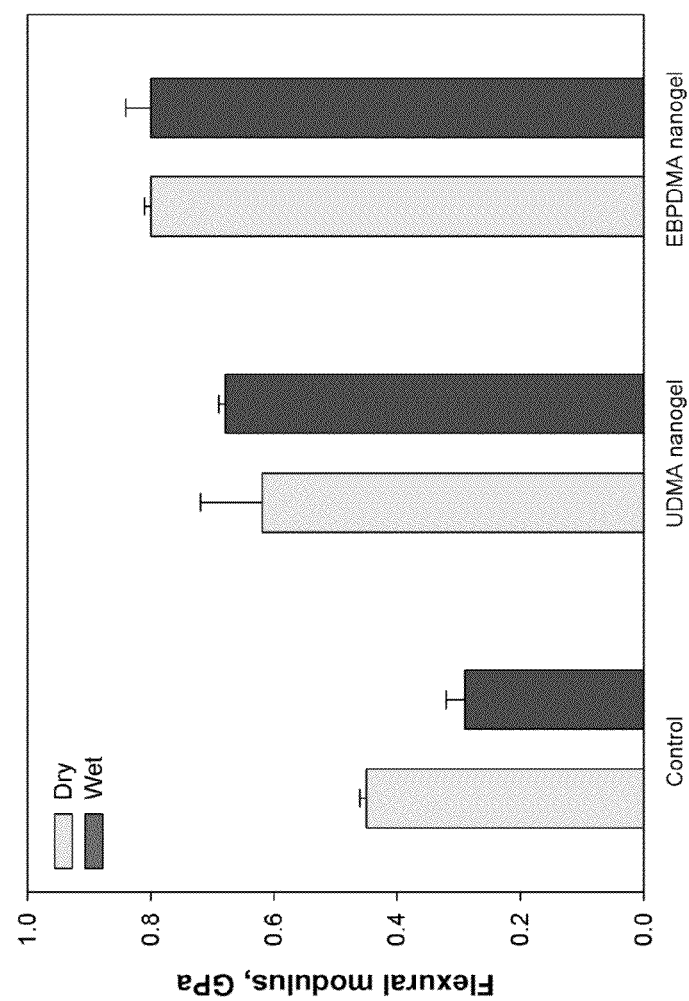
FIG. 19 shows the flexural modulus of 2×2×25 mm photopolymer specimens in a three-point bending mode after wet or dry storage (n=5) of photopolymer prepared from either BisGMA/HEMA as control, control with 25 wt % IBMA/UDMA reactive nanogel, or control with 25 wt % IBMA/EBPDMA reactive nanogel.
Figure 20:
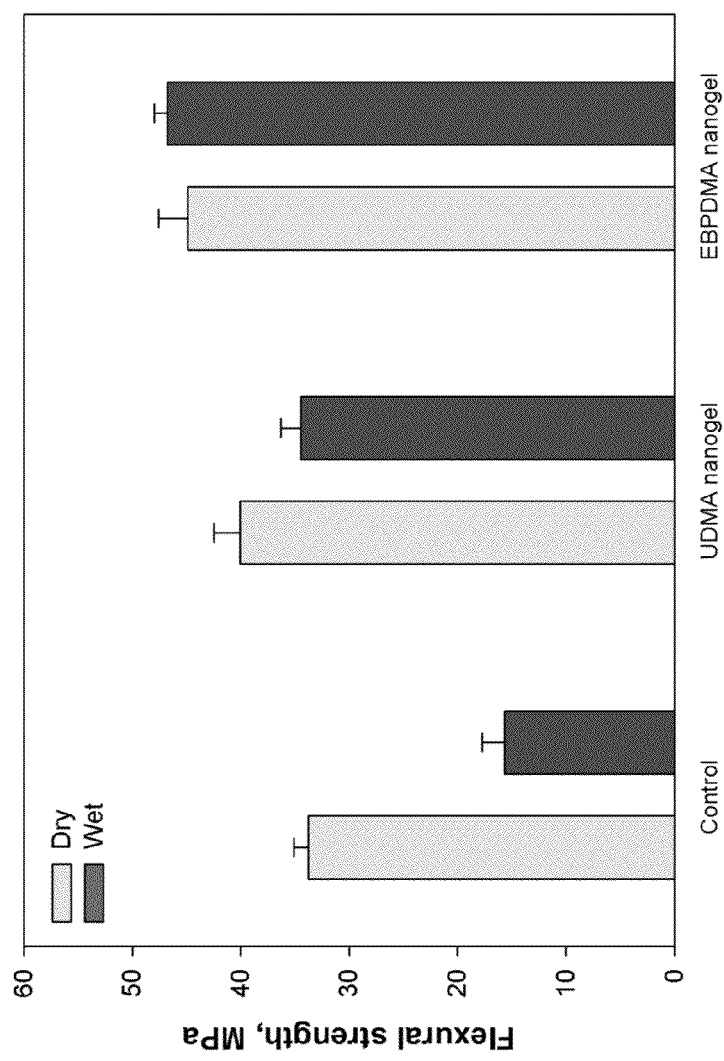
FIG. 20 shows the flexural strength of 2×2×25 mm photopolymer specimens in a three-point bending mode after wet or dry storage (n=5) of photopolymer prepared from either BisGMA/HEMA as control, control with 25 wt % IBMA/UDMA reactive nanogel, or control with 25 wt % IBMA/EBPDMA reactive nanogel.

The effects of reactive nanogel addition on mechanical properties of photopolymers were examined. The photopolymers were stored under dry conditions, or in water, for one week prior to testing. Samples were prepared from Bis-GMA/HEMA (60:40) with 10 wt % ethanol as control to mimic the composition of a clinically applied bonding resin at the time of photopolymerization. The nanogel-modified samples were obtained by dispersing 25 wt % of either IBMA/UDMA nanogel (moderately hydrophobic) or IBMA/UDMA nanogel (hydrophobic) into the control. The nanogels were prepared with mercaptoethanol (15 mol %) which was used to attach reactive (meth)acrylate groups to the particles through reaction with isocyanatoethyl(meth)acrylate. Therefore, the nanogels were both reactive nanogels with pendant (meth)acrylate groups. All specimens were stored for one week, either dry or in water, prior to testing. The flexural modulus is shown in FIG. 19 and the flexural strength is shown in FIG. 20 for 2×2×25 mm photopolymer specimens in three-point bending mode (n=5). The demonstration of higher dry strength is important, but the critical result is that the nanogel-modified adhesive resins suffer no loss in modulus or strength after one week storage in water. The results with the more hydrophobic nanogel appear to be even more favorable. When compared with the approximately 50% reduction in mechanical properties for the wet control material, this nanogel approach has a unique potential to dramatically improve the clinical performance of dental adhesives.

I claim:

1. A soluble polymer particulate derived from a monomer mixture comprising:
   at least one monovinyl monomer;
   at least one divinyl monomer at an amount of at least about 25 mol % of based on the total moles of the monomer mixture;
   a chain transfer agent; and
   a monomeric iniferter;
   wherein the soluble polymer particulate has a diameter of from about 1 nm to about 60 nm.

2. The soluble particle particulate of claim 1 wherein the chain transfer agent is selected from the group consisting of monofunctional thiols, difunctional thiols, trifunctional thiols, tetrafunctional thiols, pentafunctional thiols, hexafunctional thiols, octafunctional thiols, and bis(borondifluorodimethylglyoximate) cobaltate (II).

3. The soluble polymer particulate of claim 1 wherein said chain transfer agent is selected from the group consisting of propyl mercaptan, butyl mercaptan, hexyl mercaptan, octyl mercaptan, dodecanethiol, thioglycolic acid, methylbenzenethiol, dodecanethiol, mercaptopropionic acid, 2-ethyl hexyl thioglycolate, octylthioglycolate, mercaptoethanol, mercaptoundecanoic acid, thiolactic acid, thiobutyric acid, trimethylol propane tris(3-mercaptopropionate), pentaerythritol tetra(3-mercaptopropionate), pentaerythritol tetrathioglycolate, pentaerythritol tetrathiolactate, pentaerythritol tetrathiobutyrate; dipentaerythritol hexa(3-mercaptopropionate), dipentaerythritol hexathioglycolate; tripentaerythritol octa(3-mercaptopropionate), and tripentaerythritol octathioglycolate.

4. The soluble polymer particulate of claim 3 wherein said chain transfer agent is selected from 1-dodecanethiol and mercaptoethanol.

5. The soluble polymer particulate of claim 1 wherein the monomer mixture further comprises a thermal initiator.

6. The soluble polymer particulate of claim 1 wherein the monomer mixture further comprises a photoinitiator.

7. The soluble polymer particulate according to claim 1 wherein said monomer mixture contains at least about 50 mol % divinyl monomer based on the total moles of the monomer mixture.

8. The soluble polymer particulate according to claim 7 wherein said monomer mixture contains at least about 75 mol % divinyl monomer based on the total moles of the monomer mixture.

9. The soluble polymer particulate of claim 1 wherein said monovinyl monomer is a $C_1$-$C_{20}$ alkyl(meth)acrylate, aromatic (meth)acrylate, itaconic acid, (meth)acrylic acid, acrylic acid or other —COOH containing monovinyl monomer.

10. The soluble polymer particulate of claim 9 wherein said monovinyl monomer is the $C_1$-$C_{20}$ alkyl(meth)acrylate, and wherein the $C_1$-$C_{20}$ alkyl(meth)acrylate is ethyl(meth)acrylate or isobornyl(meth)acrylate.

11. The soluble polymer particulate of claim 9 wherein said monovinyl monomer is the aromatic (meth)acrylate, and wherein the aromatic (meth)acrylate is 2-phenoxyethyl (meth)acrylate, benzoyl(meth)acrylate, or phenyl(meth)acrylate.

12. The soluble polymer particulate of claim 1 wherein said divinyl monomer is selected from one or more of the following: ethylene glycol di(meth)acrylate, hexanediol di(meth)acrylate, tripropylene glycol di(meth)acrylate, butanediol di(meth)acrylate, neopentyl glycol di(meth)acrylate, diethylene glycol di(meth)acrylate, triethylene glycol di(meth)acrylate, dipropylene glycol di(meth)acrylate, allyl(meth)acrylate, urethane di(meth)acrylate, 2,2'-bis[4-(3-methacryloxy-2-hydroxy propoxy)-phenyl]propane (bis-GMA), ethoxylated bisphenol-A-di(meth)acrylate and divinyl benzene.

13. The soluble polymer particulate of claim 12 wherein said divinyl monomer is ethylene glycol di(meth)acrylate or urethane di(meth)acrylate.

14. The soluble polymer particulate of claim 1 wherein said iniferter is selected from a photoiniferter or a thermal iniferter.

15. The soluble polymer particulate of claim 14 wherein said iniferter is the photoiniferter, which is selected from the group consisting of diphenyldisulfide, benzyl N,N-diethyldithiocarbamate, tetraetylthiuram disulfide, phenyltriphenylazomethane, isopropylxanthic disulfide, p-xylylene bis-N,N-diethyldithiocarbamate, and benzyl dithiocarbamate.

16. The soluble polymer particulate of claim 14 wherein said iniferter is the thermal iniferter, which is selected from the group consisting of N-bromosuccinimide (NBS), diethyl-2,3-dicyano-2,3-di(p-tolypsuccinate (DCDTS), phenylazotriphenyl methane (APT), and diethyl 2,3-dicyano-2,3-di(p-N,N-diethyldithiocarbamylmethyl)phenyl-succinate (DDDCS).

17. A method of making a nanogel comprising:
(i) combining a monomer mixture comprising a monovinyl monomer, a divinyl monomer at an amount of at least about 25 mol % of based on the total moles of the monomer mixture, an initiator, a chain transfer agent, and an a monomeric iniferter; and
(ii) initiating polymerization of the monomer mixture;
wherein the nanogel has a diameter of from about 1 nm to about 60 nm.

18. The method of claim 17 further comprising dissolving said monomer mixture in a solvent.

19. The method of claim 18 further comprising recovering the nanogel polymer from the solvent after polymerization.

20. A method of preparing a surface-derivitized nanogel, the method comprising:
(i) combining a monomer mixture comprising a monovinyl monomer, a divinyl monomer at an amount of at least about 25 mol % of based on the total moles of the monomer mixture, an initiator, a chain transfer agent, and a monomeric iniferter;
(ii) initiating polymerization of the monomer mixture to form a living nanogel;
(iii) adding an additional monomer without additional initiator to the living nanogel to create a nanogel monomer mixture; and
(iv) polymerizing the nanogel monomer mixture to form a surface-derivitized nanogel;
wherein the surface-derivitized nanogel has a diameter of from about 1 nm to about 60 nm.

21. A reactive nanogel with pendant reactive surface groups produced by a process comprising:
(i) combining a monomer mixture comprising at least one functional monomer, at least one divinyl monomer at an amount of at least about 25 mol % of based on the total moles of the monomer mixture, and a chain transfer agent; wherein the functional monomer is an acrylate or methacrylate monomer having one or more additional reactive groups, wherein the additional reactive groups are selected from the group consisting of —COOH, hydroxyalkyl, oxirane, dialkyl aminoalkyl, and norbornyl;
(ii) initiating polymerization of the monomer mixture to form a living nanogel;
(iii) adding an additional monomer without additional initiator to the living nanogel to create a nanogel monomer mixture; and
(iv) polymerizing the nanogel monomer mixture to form a reactive nanogel with pendant reactive surface groups;
wherein the reactive nanogel with pendant reactive surface groups has a diameter of from about 1 nm to about 60 nm.

22. The reactive nanogel of claim 21 wherein the additional monomer is selected from a multi-vinyl monomer, a divinyl monomer, or a functional monomer.

23. The reactive monomer of claim 22 wherein the functional monomer is selected from hydroxy alkylacrylates, hydroxy alkyl(meth)acrylates, oxirane(meth)acrylates, dialkyl amino alkyl(meth)acrylates, and norbornyl(meth)acrylate.

24. The reactive nanogel of claim 21 wherein the monomer mixture further comprises an iniferter.

25. The reactive nanogel of claim 21 wherein the monomer mixture further comprises an initiator.

26. A reactive nanogel with pendant olefinic groups produced by a process comprising:
(i) combining a monomer mixture comprising at least one functional monomer, at least one divinyl monomer at an amount of at least about 25 mol % of based on the total moles of the monomer mixture, a difunctional chain transfer agent, and an initiator agent; wherein the functional monomer is an acrylate or methacrylate monomer having one or more additional reactive groups, wherein the additional reactive groups are selected from the group consisting of —COOH, hydroxyalkyl, oxirane, dialkyl aminoalkyl, and norbornyl;
(ii) polymerizing said mixture to form a functionalized nanogel; and
(iii) reacting the functionalized nanogel with a reactive olefinic compound to form a reactive nanogel with pendant olefinic groups;
wherein the reactive nanogel with pendant olefinic surface groups has a diameter of from about 1 nm to about 60 nm.

27. The reactive nanogel of claim 26 wherein the pendant olefinic groups are selected from styryl, allyl, vinyl ether, and (meth)acrylate groups.

28. The reactive nanogel of claim 26 wherein the reactive olefinic compound is selected from (meth)acryloyl chloride, (meth)acrylic anhydride, (meth)acrylic acid, isocyanatoalkyl (meth)acrylate, isocyanatoethyl(meth)acrylate vinylbenzene chloride, chloroethyl vinyl ether, allyl chloride and isocyanatomethyl(meth)acrylate.

29. The reactive nanogel of claim 26 wherein the difunctional chain transfer agent is selected from mercaptoethanol, mercaptopropanol, 3-mercapto-2-butanol, 2-mercapto-3-butanol, 3-mercapto-2-methyl-butan-1-ol, 3-mercapto-3-methyl-hexan-1-ol and 3-mercaptohexanol.

30. A soluble polymer particulate derived from a monomer mixture comprising the monovinyl monomer isobornyl (meth)acrylate (IBMA), the divinyl monomer urethane di(meth)acrylate (UDMA), photoinitiator bis-acylphosphine oxide (BAPO), and greater than 70% v/w solvent; wherein the monomer mixture does not comprise a chain transfer reagent and wherein the molar ratio of IBMA to UDMA in the monomer mixture is 70:30 mol %.

31. The soluble particle particulate of claim 1 having a hydrodynamic radius of from about 3.7 nm to about 7.8 nanometers.

* * * * *